US012714622B2

(12) United States Patent
Khair et al.

(10) Patent No.: US 12,714,622 B2
(45) Date of Patent: Aug. 25, 2026

(54) METHODS AND SYSTEMS FOR DETECTING PATIENT CHARACTERISTICS IN AN INFANT CARE STATION

(71) Applicant: GE Precision Healthcare LLC, Wauwatosa, WI (US)

(72) Inventors: Mohammad Khair, Whitefish Bay, WI (US); Kalaivani Manickam, Solihull (GB); Steven M. Falk, Baltimore, MD (US); Nagapriya Kavoori Sethumadhavan, Bangalore (IN); Rajendra Naik, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 972 days.

(21) Appl. No.: 17/957,370

(22) Filed: Sep. 30, 2022

(65) Prior Publication Data

US 2024/0108524 A1 Apr. 4, 2024

(51) Int. Cl.

| | |
|---|---|
| ***A61G 11/00*** | (2006.01) |
| ***A61B 5/00*** | (2006.01) |
| ***A61B 5/01*** | (2006.01) |
| ***A61B 5/0205*** | (2006.01) |
| ***A61B 5/024*** | (2006.01) |
| ***A61B 5/0245*** | (2006.01) |

(Continued)

(52) U.S. Cl.

CPC ............ *A61G 11/00* (2013.01); *A61B 5/0245* (2013.01); *A61B 5/1116* (2013.01); *A61B 5/4094* (2013.01); *A61B 5/4815* (2013.01); *A61B 5/4824* (2013.01); *A61M 21/02* (2013.01); *G06T 7/73* (2017.01); *G06T 17/20* (2013.01);

(Continued)

(58) Field of Classification Search

CPC ..... A61G 11/00; A61B 5/0245; A61B 5/1116; A61B 5/4094; A61B 5/4815; A61B 5/4824; A61B 5/02433; A61B 5/14552; A61B 5/4806; A61B 5/7267; A61B 5/1118; A61B 2503/045; A61B 5/02055; A61B 5/01; A61B 5/14542; A61B 5/746; A61B 2503/04; A61M 21/02; A61M 2021/0022; A61M 2021/0027; A61M 2021/005; G06T 7/73; G06T 17/20; G06T 2207/10016; G06T 2207/10028; G06T 2207/20081; G06T 2207/20084; G06T 2207/30201; G06V 10/82; G06V 40/168; G06V 40/174

See application file for complete search history.

(56) References Cited

U.S. PATENT DOCUMENTS

| | | | |
|---|---|---|---|
| 6,679,830 | B2 | 1/2004 | Kolarovic |
| 7,725,146 | B2 | 5/2010 | Li |

(Continued)

OTHER PUBLICATIONS

EP application 23198189.5 filed Sep. 19, 2023—extended Search Report issued Feb. 16, 2024; 10 pages.

*Primary Examiner* — Carrie R Dorna
*Assistant Examiner* — Joshua Daryl D Lannu

(57) ABSTRACT

In one example, an infant care station can include a camera for capturing video data and a processor configured to execute instructions that can obtain the video data from the camera for a patient. The processor can also generate a point cloud based on the video data and train, using the point cloud as input, a first set of artificial intelligence instructions to detect one or more patient characteristics. Additionally, the processor can generate an output representing the one or more patient characteristics based on the first set of artificial intelligence instructions.

20 Claims, 32 Drawing Sheets

(51) Int. Cl.

| | |
|---|---|
| ***A61B 5/11*** | (2006.01) |
| ***A61B 5/1455*** | (2006.01) |
| ***A61M 21/00*** | (2006.01) |
| ***A61M 21/02*** | (2006.01) |
| ***G06T 7/73*** | (2017.01) |
| ***G06T 17/20*** | (2006.01) |
| ***G06V 10/82*** | (2022.01) |
| ***G06V 40/16*** | (2022.01) |

(52) U.S. Cl.

CPC ............ *G06V 10/82* (2022.01); *G06V 40/168* (2022.01); *G06V 40/174* (2022.01); *A61M 2021/0022* (2013.01); *A61M 2021/0027* (2013.01); *A61M 2021/005* (2013.01); *G06T 2207/10016* (2013.01); *G06T 2207/10028* (2013.01); *G06T 2207/20081* (2013.01); *G06T 2207/20084* (2013.01); *G06T 2207/30201* (2013.01)

(56) References Cited

U.S. PATENT DOCUMENTS

| | | | |
|---|---|---|---|
| 10,342,464 | B2 | 7/2019 | Niemeyer |
| 10,398,353 | B2 | 9/2019 | Addison |
| 10,413,226 | B2 | 9/2019 | Tao |
| 10,506,960 | B2 | 12/2019 | Kaestle |
| 10,736,579 | B2 | 8/2020 | Van Berkel-Wijnen |
| 10,825,314 | B2 | 11/2020 | White |
| 10,925,496 | B2 | 2/2021 | Misharin |
| 11,138,856 | B1 | 10/2021 | Bharati |
| 11,446,466 | B1 * | 9/2022 | Shvartzman ......... A61B 5/4809 |
| 2008/0082018 | A1 | 4/2008 | Sackner |
| 2011/0046498 | A1 | 2/2011 | Klap |
| 2012/0197142 | A1 | 8/2012 | Lovejoy |
| 2014/0148663 | A1 | 5/2014 | Bresch |
| 2017/0014087 | A1 | 1/2017 | Verkruijsse |
| 2017/0055877 | A1 | 3/2017 | Niemeyer |
| 2017/0127988 | A1 | 5/2017 | Tao |
| 2017/0238805 | A1 | 8/2017 | Addison |
| 2017/0319114 | A1 | 11/2017 | Kaestle |
| 2019/0159739 | A1 | 5/2019 | Shah |
| 2019/0320974 | A1 | 10/2019 | Alzamzmi |
| 2020/0384239 | A1 | 12/2020 | Fornell |
| 2021/0030354 | A1 | 2/2021 | Alzamzmi |
| 2021/0137396 | A1 | 5/2021 | Misharin |
| 2021/0219855 | A1 | 7/2021 | Misharin |
| 2022/0415002 | A1 * | 12/2022 | Sauer ...................... G06T 17/20 |

* cited by examiner

200

300

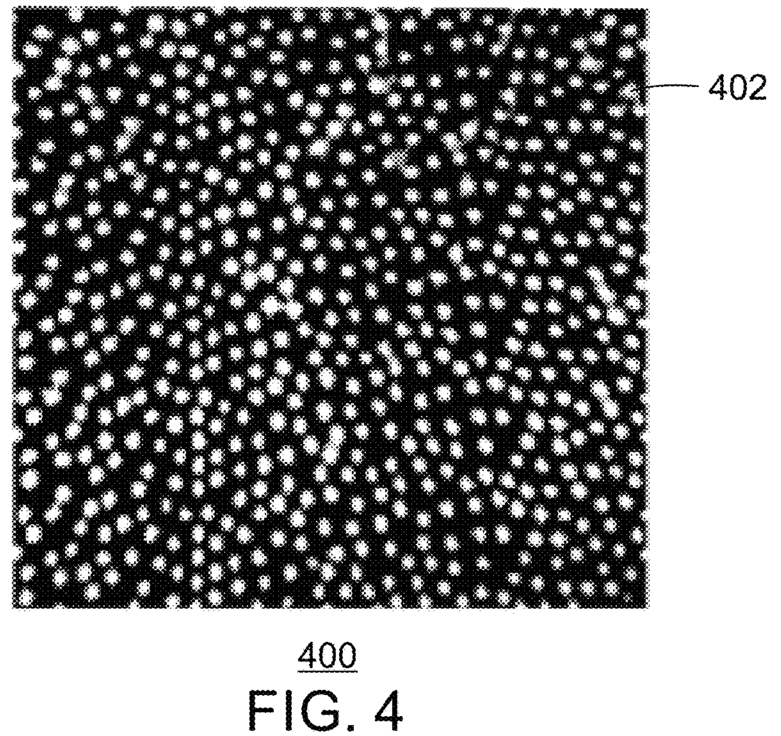
400
FIG. 4
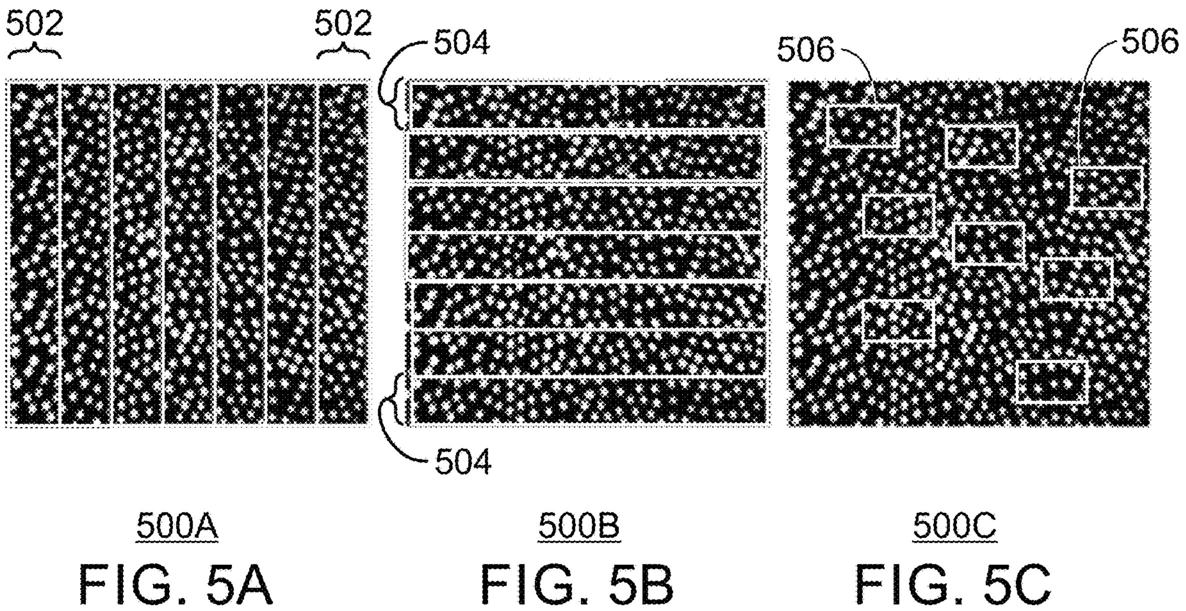
500A
FIG. 5A
500B
FIG. 5B
500C
FIG. 5C

1100

1200

1300

1400

1500

1700

1800

1900

2000

2100

2300

2400

2500

2600

2900

Raw Data
3210

Learning
Network
3220

Image
3230

3200

METHODS AND SYSTEMS FOR DETECTING PATIENT CHARACTERISTICS IN AN INFANT CARE STATION

BACKGROUND

The present disclosure generally relates to infant care stations, and more specifically to detecting patient characteristics for a neonatal patient in an enclosure of an infant care station.

Some neonates are not physiologically well enough developed to be able to survive without special medical attention. A frequently used medical aid for such infants is the incubator. The primary objective of the incubator is to provide an environment which will maintain the neonate at a minimum metabolic state thereby permitting as rapid physiological development as possible. Neonatal incubators create a microenvironment that is thermally neutral where a neonate can develop. These incubators typically include a humidifier and a heater and associated control system that controls the humidity and temperature in the neonatal microenvironment. The humidifier comprises a device that evaporates an evaporant, such as distilled water, to increase relative humidity of air within the neonatal microenvironment. The humidifier is typically controllable such that the amount of water, or water vapor, added to the microenvironment is adjustable in order to control the humidity to a desired value. The heater may be, for example, an air heater controllable to maintain the microenvironment area to a certain temperature. Radiant warmers may be used instead of incubators for some neonates where less environmental control is required. In still other embodiments, hybrid incubator/radiant warming systems may be utilized.

Since the microenvironment is accurately controlled in a neonatal care system, the care system includes an enclosure that is sealed as best possible to help maintain the controlled microenvironment. Such an enclosure will typically include four sidewalls or side panels and a top hood that surround an infant support platform. Typically, one or more of the side panels can include access points, such as porthole doors, and a removable top, among others, that enable clinicians to access neonates in the microenvironment. In some examples, detecting a patient's oxygen saturation level, heart rate, respiratory rate, and the like, may involve accessing the patient through an access point.

SUMMARY

This summary is provided to introduce a selection of concepts that are further described below in the Detailed Description. This Summary is not intended to identify key or essential features of the claimed subject matter, nor is it intended to be used as an aid in limiting the scope of the claimed subject matter.

An infant care station can include a camera and a processor to obtain the video data from the camera for a patient, generate a point cloud based on the video data, train, using the point cloud as input, a first set of artificial intelligence instructions to detect one or more neonatal patient characteristics, and generate an output representing the one or more patient characteristics based on the first set of artificial intelligence instructions.

In some examples, the infant care station can include a processor to obtain an infrared camera image, extract one or more movement indicators from the infrared camera image, use wavelet decomposition to determine at least two data streams from the one or movement indicators, process the two data streams from the wavelet decomposition to determine any number of peaks that indicate a heart rate, respiratory rate, or a motion of a patient, provide the processed output to a user interface.

In some examples, the infant care station can include a processor to create a first Red plethysmograph waveform from a red image, create a second IR plethysmograph waveform from an infrared (IR) image, process the first Red plethysmograph waveform using wavelet decomposition to obtain a first pulse plethysmograph waveform, process said first pulse plethysmograph waveform for peak to peak interval indicating first HR value, process the second plethysmograph waveform using wavelet decomposition to obtain a second pulse plethysmograph waveform, process said second pulse plethysmograph waveform for peak to peak interval indicating second HR value, calculate an oxygen absorption value using the first pulse plethysmograph waveform and the second pulse plethysmograph waveform, and determine the oxygen saturation value for the patient using a reference calibration curve and the absorption value.

Various other features, objects, and advantages of the invention will be made apparent from the following description taken together with the drawings.

BRIEF DESCRIPTION OF THE DRAWINGS

The drawings illustrate the best mode presently contemplated of carrying out the disclosure. In the drawings:

FIG. 4 is an infrared image of a patient in an infant care station;

FIGS. 5A, 5B, and 5C are example infrared images;

FIGS. 22A-22D are example images of patients in an infant care station with different levels of light, with or without blankets, and the like;

Figure 1:
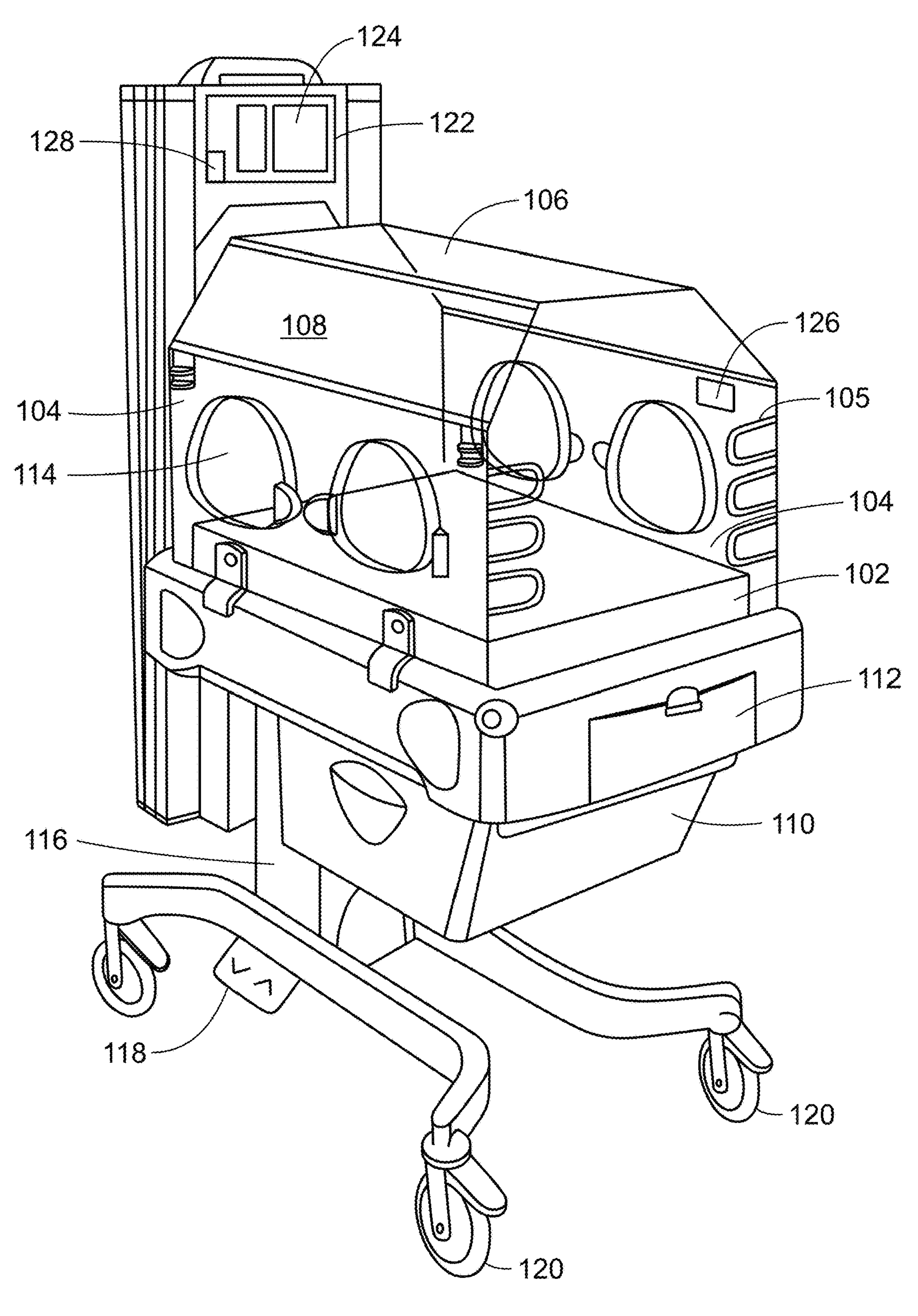
FIG. 1 is a perspective view of an example infant care station in accordance with one example.

The drawings illustrate specific aspects of the described components, systems and methods for providing a neonatal incubator system. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems and methods.

DETAILED DESCRIPTION

Embodiments of the present disclosure will now be described, by way of example, with reference to FIGS. 1-35. Infant care stations can provide microenvironments for infant patients receiving medical care. Infant care stations, as referred to herein, can include incubators, warmers, or devices that support one or more features of incubators and warmers. In some examples described herein, patient characteristics can be automatically detected, obtained, or otherwise received from the infant care station by monitoring a neonatal patient in the infant care station with one or more cameras. The cameras can capture or obtain red, green, and blue video data streams, left and right imagers infrared video data streams, red, green, and blue data streams with depth information, or the like.

In some examples, red images from a camera and infrared images from a camera can be obtained and used to create a plethysmograph waveform. Techniques described herein can separate the plethysmograph waveform into two or more plethysmograph waveforms that represent a heart rate, respiratory rate, and motion of a patient in an infant care station.

In some examples, techniques described herein can separate the plethysmograph waveform into a pulse plethysmograph waveform. Additionally, the techniques can determine the oxygen saturation value for a patient using a reference calibration curve and an absorption value based on the pulse plethysmograph waveform.

In some examples, the infant care stations can enable clinicians to access the patient by opening one or more access points. An access point, as referred to herein, includes porthole doors that reside within one or more walls of the infant care stations, removable canopies of infant care stations, and the like. For example, a clinician may disengage any suitable latch coupled to the porthole doors to open the porthole doors and access a patient residing within an infant care station. However, porthole doors can be accidentally left open, which can result in unexpected conditions within the microenvironment of the infant care station. Techniques herein can detect open access point, anomalies in air curtains due to malfunctioning fans, and the like.

Techniques described herein enable an infant care station to detect any number of patient characteristics when a patient is in the infant care station. In some examples, an infant care station can include one or more cameras that can capture or obtain any number of images, videos, or the like, of a patient in the infant care station. The images or videos can be used detect, measure, or otherwise determine any number of patient characteristics such as a sleeping position, facial gestures, an oxygen saturation level, a heart rate, a respiratory rate, and the like.

An advantage that may be realized by the patient characteristic detection feature in the practice of some examples of the described systems and techniques is an additional safety mechanism to ensure timely treatment of a patient. The techniques herein can automatically monitor and detect oxygen saturation levels, patient characteristics that indicate a patient is in pain or is having a seizure, patient characteristics indicating a heart rate or respiratory rate, or the like. Accordingly, techniques herein can identify changes for a patient within the microenvironment of an infant care station. Techniques for detecting patient characteristics are described in greater detail below in relation to FIGS. 1-35.

FIG. 1 is a perspective view of an example infant care station in accordance with one example. In the example of FIG. 1, an infant care station is depicted in which the infant care station is an incubator 100. The incubator 100 includes a horizontal surface 102 that is configured to support an infant patient (not depicted). It is to be understood that the incubator 100 may have the ability or control to move, rotate, or incline the horizontal surface 102; however, it will be understood that the horizontal surface 102 will generally remain horizontal such as to minimize movement of the infant patient within the incubator 100 due to gravity.

One or more walls 104 extend generally vertically from the horizontal surface 102. In the embodiment depicted in FIG. 1 of the incubator 100, four walls extend vertically from the horizontal surface 102 to define the rectangular shape of the incubator 100. However, it will be understood that in alternative examples, various numbers of walls 104 may be used to define the incubator into various geometric shapes which may include, but are not limited to, circles or hexagons. The incubator 100 can further include a canopy 106 that extends over the horizontal surface 102. In some examples, the canopy 106 can include multiple components or surfaces, or the canopy may be curved or domed in shape.

While the incubator of FIG. 1 is depicted with the horizontal surface 102, walls 104, and canopy 106 being connected, it will be understood that in alternative examples, including those described in greater detail herein, the horizontal surface 102, walls 104, and canopy 106 may be individual components that also may be moveable with respect to each other. For example, the canopy 106 can transition from a closed position to an open position in which any suitable portion of the canopy 106 is raised away from the walls 104 to allow the microenvironment to be exposed to the surrounding environment of the incubator 100.

The horizontal surface 102, walls 104, and canopy 106 can define a microenvironment 108 contained within these structures. In some examples, the incubator 100 is configured such that the microenvironment 108 surrounds the infant patient (not depicted) such that the infant patient is only exposed to a controlled combination of environmental characteristics or conditions (temperature, humidity, $O_2$ concentration, etc.) selected by a clinician to promote the health and wellbeing of the infant patient. In some examples, the walls 104 further include arm portholes 114 that permit a clinician access into the microenvironment 108.

In some examples, the incubator 100 includes a base 110 that houses a convective heater 112. The convective heater 112 is operated such that air is drawn into the incubator 100, at which point the air may be filtered or sterilized in another manner, including the use of UV light before being passed by heating coils (not depicted) to heat the air to a target or set point temperature. The sterilized and heated air is blown into the microenvironment 108 through vents (not depicted) which are arranged along the walls 104. As is also known, the air may be entrained with supplemental gasses such as oxygen or may have added humidity such as to control these conditions within the microenvironment 108.

Examples of the incubator 100 further include a pedestal 116 connected to the base 110. The pedestal 116 includes mechanical components (not depicted), which may include, but are not limited to, servo motors, rack and pinion systems, or screw gear mechanisms that are operable by foot pedals 118 to raise or lower the base 110, effectively raising or lowering the position of the infant patient (not depicted) in relation to the clinician. The incubator 100 may be moveable by wheels or casters 120 connected to the pedestal 116.

The example of the incubator 100 depicted in FIG. 1 includes a graphical display 122 that is mounted to a wall, the base 110, or the canopy 106 of the incubator 100 at a position external to the microenvironment 108. The graphical display 122 is operated by a processor to present a graphical user interface (GUI) 124. In the example illustrated, the graphical display 122 is a touch-sensitive graphical display and the GUI 124 is configured to specifically respond to inputs made by a clinician received through the touch-sensitive graphical display. During normal operation, the touch-sensitive graphical display 122 and touch-sensitive configured GUI 124 are used to control various functions of the incubator 100. The GUI 124 presents a variety of information, such as the air temperature and alarm indications. In some examples, the alarm indications can provide a message indicating an access point is unsealed or open, a change in environment characteristics, or a warning that a heater is still operational after the canopy 106 has been closed, among others.

In some examples, the walls 104 of the incubator 100 can be opened or closed to enable a clinician to access a patient residing in the incubator 100. For example, the walls 104 can serve as doors that open and close to either remove a patient from the incubator 100 or to place a patient into the incubator 100. The walls 104 can include any number of access points, such as portholes 114 covered by porthole doors, that enable access to a patient residing in a microenvironment of the incubator 100. In some examples, the canopy 106 can also be removed to access a patient within the incubator 100.

In some examples, the incubator 100 can include any number of cameras 126. In some examples, the cameras 126 are connected to a host device 128 that controls the GUI 124. The cameras 126 can transmit image data to the host device 128 and the host device 128 can determine patient characteristics and if any access points, such as the canopy 106 or portholes 114, of the incubator 100 are unsealed or open. In some examples, the cameras 126 can transmit image data indicating patient characteristics using any suitable wired or wireless transmission protocol. The host device 128 can determine patient characteristics as discussed in greater detail below in relation to FIG. 24.

In some examples, one or more cameras 126 can be mounted or affixed to the infant care station 100 so that the one or more cameras 126 can capture or obtain at least one video data stream of a neonatal patient. The video data streams can include depth data, infrared data, color data, black and white data, or any other suitable data streams of a neonatal patient, an enclosure of the infant care station 100, or a combination thereof. In some examples, the video data stream can be analyzed or processed to detect one or more movement indicators for a neonatal patient. The movement indicators can represent a movement of a patient within an area monitored by a camera 126. The movement indicators can measure intensity pixel values indicating a movement within a pixel or a group of pixels. The intensity pixel values can be processed or analyzed to determine a movement corresponding to a respiratory rate, a heart rate, or movement of a neonatal patient as discussed in greater detail below in relation to FIGS. 2-35.

In some examples, the cameras 126 of the infant care station 100 can obtain a red-green-blue image as well as an infrared camera image. The cameras 126 can transmit or otherwise provide the images to a host device 128 that can extract one or more movement indicators from the infrared camera image and use wavelet decomposition to determine at least two data streams from the one or movement indicators. The host device 128 can also process the two data streams from the wavelet decomposition to determine any number of peaks that indicate a heart rate, respiratory rate, or a motion of a patient, and provide the processed output to a user interface or GUI 124.

In some examples, the host device 128 can also obtain the video data from the camera 126 for a patient and generate a point cloud based on the video data. The host device 128 can also train, using the video datapoint cloud as input, a first set of artificial intelligence instructions to detect one or more neonatal patient characteristics. The host device 128 can also generate an output representing the one or more patient characteristics based on the first set of artificial intelligence instructions.

The output can indicate, for example, a sleeping position of a neonatal patient, a pose of a neonatal patient, a growth pattern, a grimace, or the like. In some examples, the output can also indicate an oxygen saturation level, heart rate, respiratory rate, temperature, or other physiologic measurements, for a patient. The infant care station 100 can generate alerts and transmit the alerts to remote devices or provide the alerts to display devices coupled to the infant care station 100. The alerts can indicate that a heart rate, respiratory rate, or oxygen saturation level are above a first predetermined threshold or below a second predetermined threshold. The alerts can also indicate if a patient may be experiencing a seizure, pain, stress, or other conditions based on facial features, body position, and the like.

Figure 2:
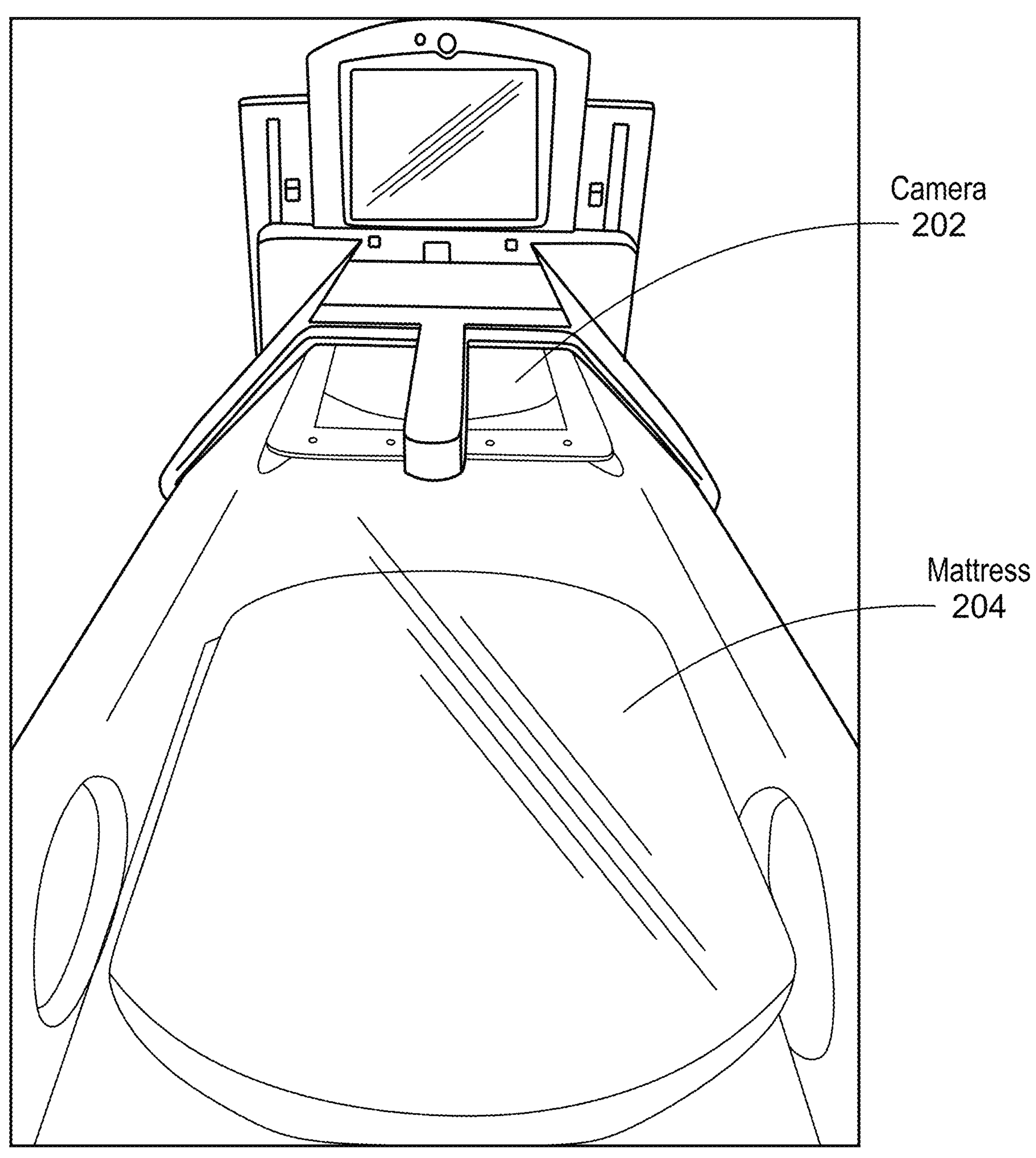
FIG. 2 is a top view of an example infant care station.

FIG. 2 is a top view of an example infant care station. In some examples, the infant care station 200 can include a camera 202 mounted above a mattress 204 of the infant care station 200. The camera 202 can capture or obtain pictures of a patient (not depicted) residing on the mattress 204 in a microenvironment of the infant care station 200. In some examples, the camera 202 can be located in any suitable location in the infant care station 200 such as a canopy, wall, or the like. The camera 202 can capture red-green-blue (RGB) images, infrared images, depth data, and the like. In some examples, any number of cameras 202 can be included in the infant care station 200 to obtain RGB images, infrared images, or depth data of a patient, among others.

It is to be understood that the block diagram of FIG. 2 is not intended to indicate that the infant care station 200 is to include all of the components shown in FIG. 2. Rather, the infant care station 200 can include fewer or additional components not illustrated in FIG. 2 (e.g., additional memory components, embedded controllers, additional modules, additional network interfaces, additional sensor devices, etc.).

Figure 3:
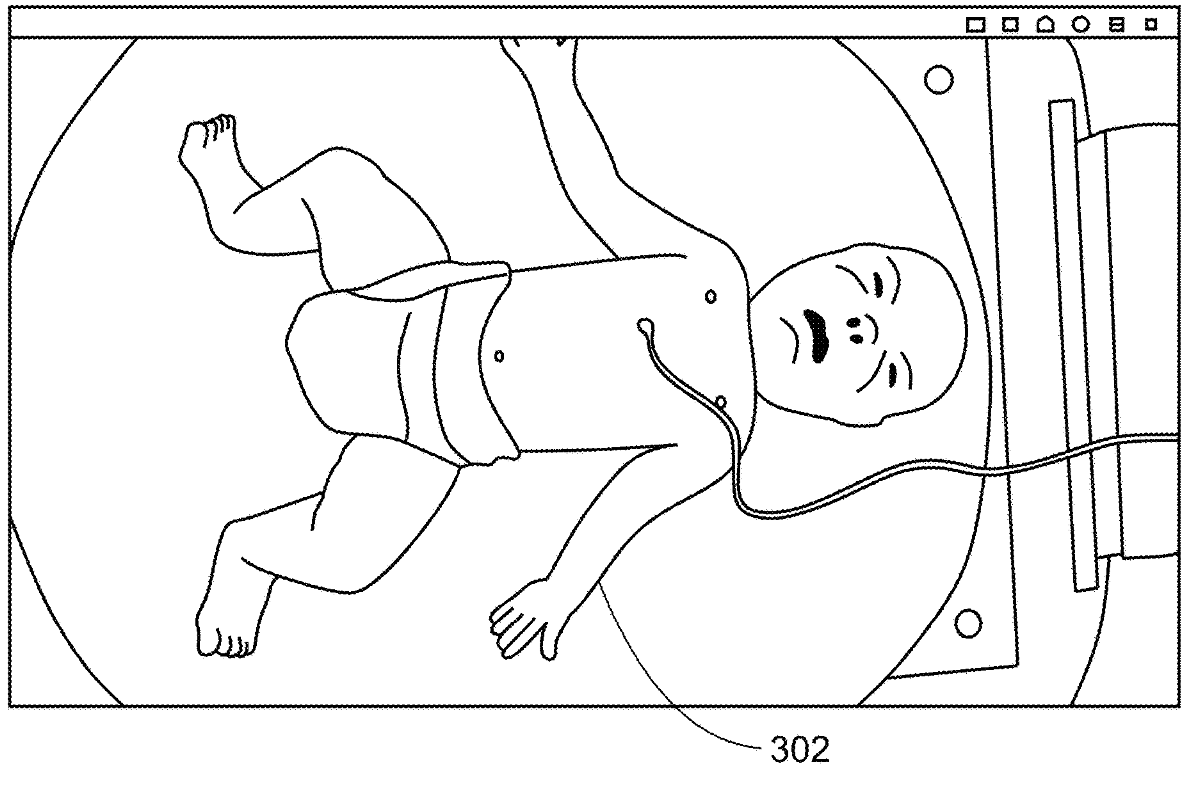
FIG. 3 is a block diagram of a camera view of a patient residing in an infant care station.

FIG. 3 is a block diagram of a camera view of a patient residing in an infant care station. In some examples, the camera view 300 is captured, obtained, or otherwise received by a camera 202 of an infant care station 200 of FIG. 2. In some examples, the camera view 300 can be from above a patient 302, to the side of a patient 302, or any other location proximate to the patient 302. In some examples, multiple different camera views can be combined from different locations proximate to the patient 302. For example, an infant care station 200 can combine camera views 300 from above a patient 302 and to the side of a patient 302 to create a three dimensional image of the patient 302. One or more cameras 202 can also capture or obtain images or video in a red-green-blue format, an infrared image format, or the like. The one or more cameras 202 can also use any suitable depth camera technique to identify or detect three dimensional data for a patient 302 in an infant care station. In some examples, the camera view 300 can also be captured with infant care station 100 of FIG. 1 using camera 126.

FIG. 4 is an infrared image of a patient in an infant care station. In some examples, the infrared image 400 can be captured, obtained, or otherwise received by a camera 202 of an infant care station 200 of FIG. 2 or camera 126 of infant care station 100 of FIG. 1. The infrared image 400 can include any number of intensity values representing a change in position or movement of the patient.

In some examples, an infrared image 400 can be processed to obtain an input signal such as a plethysmograph signal that represents blood pulsation, respiration, and movements of a patient. The heart rate and respiratory rate of a patient can be separated from the input signal using a number of different techniques. In some examples, the pulse plethysmograph waveform or time series and respiratory rate plethysmograph waveform or time series can be distinct and determined or derived from a function that aggregates the light intensities from the infrared light intensity values or spots 402 by summing their pixel values (which relates to pixel intensity levels) from any suitable segment of the infrared image 400. In some examples, the segment of the infrared image 400 to be analyzed can be along the midline of the chest area in the upper half of the body, or from the upper half of the body, or from the body view of a patient. The aggregate sum of spot pixel data from a number of infrared images 400 or frames of video across time represents the values of the time series that are analyzed for heart rate and respiratory rate.

In some examples, the infrared images 400 or video frames can be analyzed for infrared spots 402 that are separated from the remainder of the image background by the infrared spots' 402 intensity level using image preprocessing steps. The infrared image 400 can be used to calculate a sum of the intensity values of the infrared spots 402 in horizontal directions, vertical directions, or a combination thereof from the selected image segment for an aggregate total intensity value. In some examples, one or more segments per infrared image 400 or frame can be selected. For example, an intensity function, a mean function, or a median function, among others, can be used to determine an amount of movement in a segment of an infrared image. In some examples, the intensity function can calculate a spot intensity value for a frame segment that is equal to a total sum of pixels in the rows (X direction) and columns (Y direction) of the selected segment of the infrared image. In some examples, a frame mean value can be equal to the mean of spot intensity values for the segments in an infrared image. The frame median value can be equal to the median value based on the spot intensity values for segments in an infrared image.

FIGS. 5A, 5B, and 5C are example infrared images with spots representing artificial light structure due to IR light, which helps in sensing depth distance from the camera. In some examples, segments or portions of infrared images 500A, 500B, and 500C can be selected using any number of techniques. For example, the segments within the images 500A, 500B, and 500C can be selected as vertical slice image segments, horizontal slice image segments, or both, or multiple square or rectangular segments selected in scattered locations on the image frame, among others.

In FIG. 5A, vertical segments 502 are selected from infrared image 500A. In some examples, the infrared image 500A can be separated into any number of vertical segments 502 with a fixed width, a variable width, or the like. In some examples, the infrared image 500A can be completely divided into vertical segments 502, partially divided into vertical segments 502, or the like. For example, portions of the infrared image 500A between adjacent vertical segments 502 may not be analyzed or otherwise processed.

In FIG. 5B, horizontal segments 504 are selected from infrared image 500B. In some examples, the infrared image 500B can be separated into any number of horizontal segments 504 with a fixed width, a variable width, or the like. In some examples, the infrared image 500B can be completely divided into horizontal segments 504, partially divided into horizontal segments 504, or the like. For example, portions of the infrared image 500B between adjacent horizontal segments 504 may not be analyzed or otherwise processed.

In FIG. 5C, rectangular segments 506 are selected in scattered locations in infrared image 500C. In some examples, the infrared image 500C can be separated into any number of rectangular segments 506 with a fixed width, a variable width, or the like. In some examples, the infrared image 500C can be completely divided into rectangular segments 506, partially divided into rectangular segments 506, or the like. For example, portions of the infrared image 500C between adjacent rectangular segments 506 may not be analyzed or otherwise processed.

Figure 6:
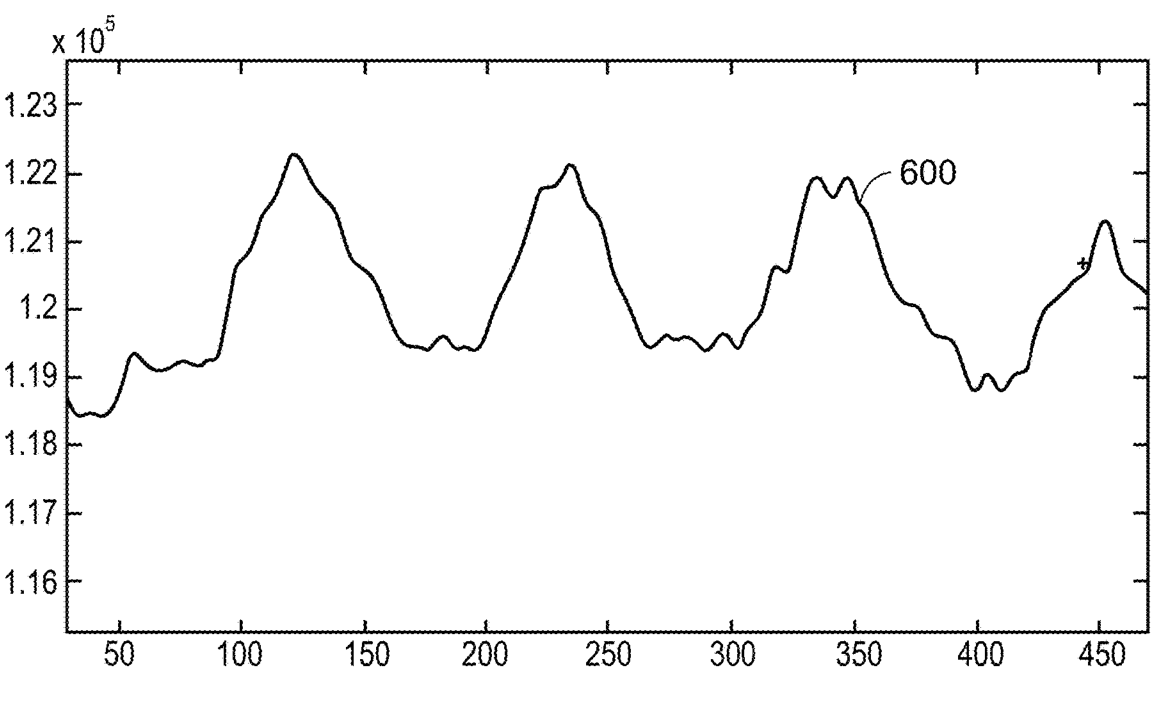
FIG. 6 is an example intensity function depicting time series with combined breathing and heart rate pulsations.

FIG. 6 is an example intensity function depicting a plethysmograph waveform or time series with combined breathing and heart rate pulsations. In some examples, the intensity function is based on pixel values from infrared images, such as infrared image 400 of FIG. 4, among others.

Figure 7:
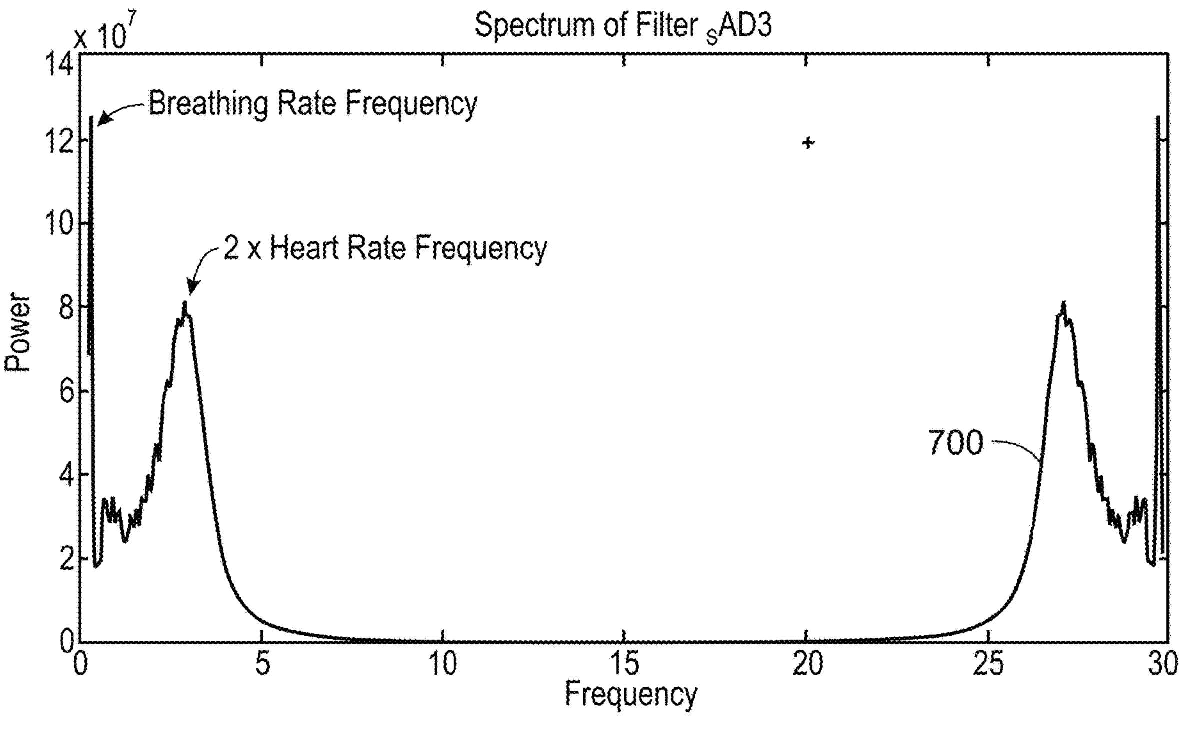
FIG. 7 is an example frequency domain for motion artifacts detected in an input signal.

In some examples, the plethysmograph waveform 600 represents the dynamics of aggregate infrared spot intensity variation based on mechanical movements of a patient within an infrared video stream or infrared images. The mechanical movements of a patient can include the heart pulsations, respiration breaths, and motion artifacts, among others, which cause physical movements of the patient's chest, limbs, and the like. In some examples, a plethysmograph waveform 600 can be transformed to a frequency domain, as illustrated in FIG. 7, in order to obtain the spectrum of frequencies with peaks representing separated components with highest power content, such as heart rate and respiration rate, among others.

In some examples, the frequency for heart rate can be found at twice the expected heart rate frequency for a patient due to the presence of a dicrotic notch, which creates two pulses per heartbeat. In other examples, with less pronounced dicrotic notch, the frequency of the heart rate can be found at the expected heart rate frequency. In some examples, a derivative of the intensity function can be used to zero a baseline of the intensity function to eliminate baseline offsets and low frequency baseline variation, which can be an intermediary technique before the frequency domain transformation.

In some examples, the plethysmograph waveform 600 or times series of the spot intensity function can be developed from either the left or right infrared imager video streams of a patient. Alternatively, both the left and right infrared image streams can be used with an average of the two intensity functions computed to reduce signal motion artifacts.

In some examples, the component of the waveform representing the respiration activity as a time series can be processed for peak detection for evaluating the respiratory rate. Time series signal processing techniques of peak detection can help define breath-to-breath respiration interval and therefore the respiratory rate. Time series processing can enable detection of respiratory apnea using a camera derived respiratory signal plethysmograph by means of monitoring for extended respiratory pauses between periodic breathing cycles with an expected interval in between. The mean or median respiratory rate and its variability can be computed and presented to the user. Similarly, the component of the waveform representing the heart pulsations activity plethysmograph as a time series can be processed for peak detection for evaluating the heart rate from the peak to peak interval. The mean or median of the heart rate and its variability over time can be calculated and presented to the user.

FIG. 7 is an example frequency domain for motion artifacts detected in an input signal. The frequency domain 700 can be detected, calculated, or otherwise obtained using any suitable plethysmograph waveform or time series, such as the plethysmograph waveform 600 of FIG. 6, among others.

In some examples, a frequency domain 700 (Fast Fourier transform or FFT, among others) of a plethysmograph waveform 600 can represent breathing and heart pulsations activity of a patient. Due to increased sensitivity to a dicrotic notch using this technique of intensity measurement, each heartbeat is detected as two pulses instead of one, which results in a spectral peak detected at two times the actual heart rate frequency. In some examples, the Dicrotic notch may be less pronounced and the heartbeat is detected as a single pulse at the actual heart rate frequency. In some examples, a breathing frequency peak can be at a lower frequency band than the heart rate band. Evaluating the respiration rate and the heart rate using frequency domain spectral information using fast Fourier transform or high resolution wavelet analysis information, such as time-frequency wavelet scalogram, among others, can increase the reliability of the estimated respiration rate and heart rate despite background motion artifacts and noise effects.

Figure 8:
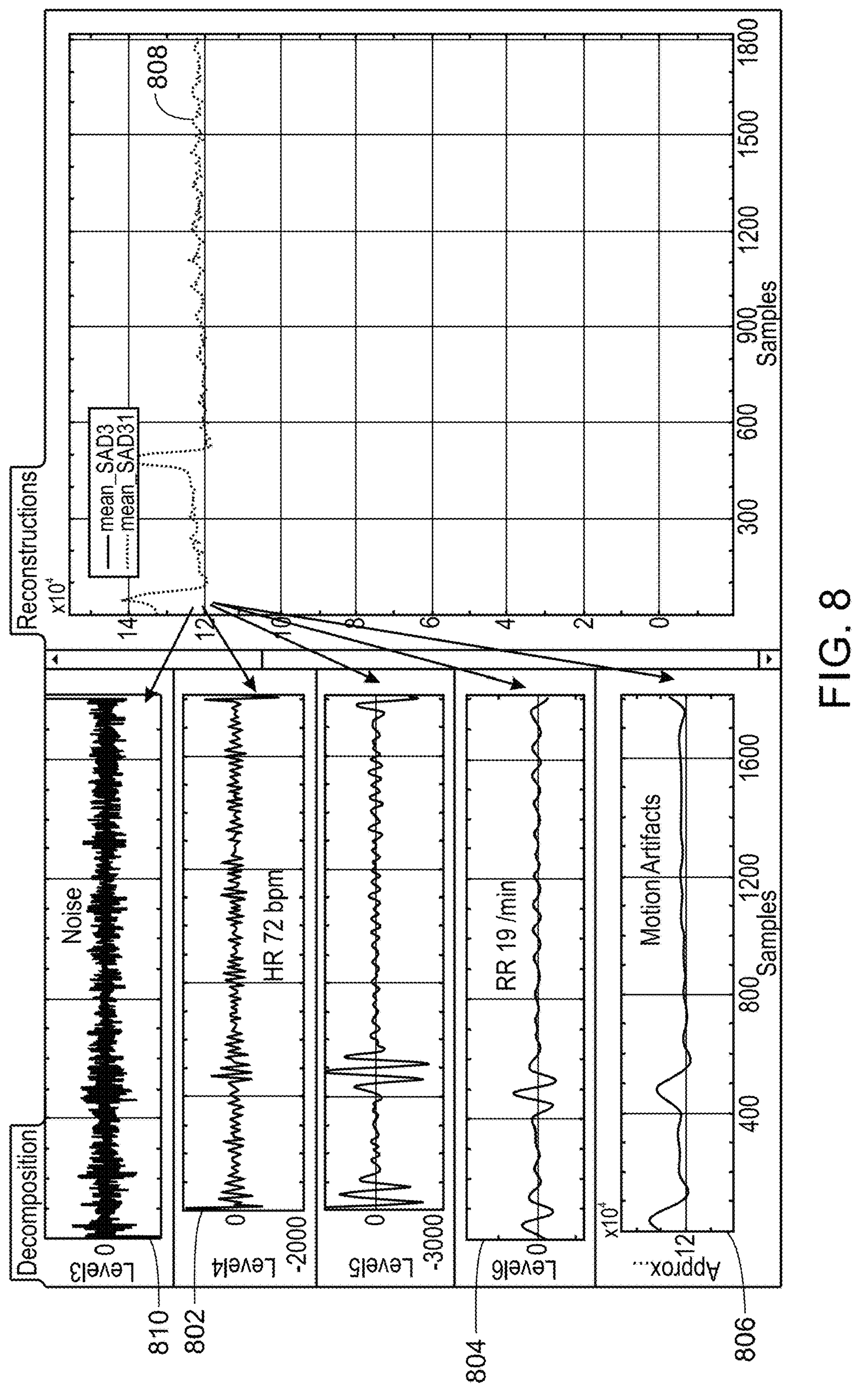
FIG. 8 is an example image of plethysmograph waveforms obtained from an input signal.

FIG. 8 is an example image of plethysmograph waveforms obtained from an input signal. In some examples, two or more plethysmograph waveforms 802, 804, and 806 can be obtained, processed, or otherwise determined based on an input signal 808. Each of the plethysmograph waveforms 802, 804, and 806 can represent a heart rate, a respiration rate, and motion of a patient in an infant care station, among others.

In some examples, any suitable technique can be used to remove noise artifacts from an input signal 808 and separate a heart rate signal 802, a respiration rate signal 804, a motion artifacts signal 806, and noise 810. For example, wavelet decomposition analysis can be used to separate the various signals 802, 804, 806, and 910 from an input signal 808.

In some examples, plethysmograph waveforms 802, 804, and 806 are mechanical in nature and can interfere with one another. Separation of plethysmograph waveforms 802, 804, and 806 from an input signal 808 using wavelet decomposition can enable evaluating an input signal 808 for a heart rate, a respiration rate, and motion artifacts. Wavelet decomposition enables high resolution localized detection and separation of signal components, such as plethysmograph waveforms 802, 804, and 806, that have different frequencies.

In some examples, pixel intensity analysis of the infrared spots in an infrared image can be analyzed within a field of view of a segment of interest, including a chest mid-line segment of a patient, among others, that is sensitive to both breathing and heart pulsations. This technique can also function when the body is covered by clothes or a blanket, among other obstructions, that are also affected by the breathing activity. When infrared is applied to exposed skin of a patient directly, part of the infrared energy is absorbed by the blood in the skin's vascular system, which may result in reduced sensitivity of the reflected infrared energy.

In some examples, a technique for detecting respiration and heart pulsations can include measuring a motion of the position of centroids of each of the light spots in a segment of interest. In this approach, each light spot centroid is measured for its pixel intensity value, and then the aggregate pixels intensities of each light spot centroid intensities can be evaluated from one image frame to the next image frame to form intensity time series that are evaluated for heart pulsations, respiration activity, or for patient motion activity. If video capture sampling frequency is above a predetermined threshold, such as 15 frames per second, or 30 frames per second, among others, techniques herein can capture a relative centroid intensity variation from infrared image at a first time to an infrared image at a second time. The technique can also include constructing a function of intensity change for each centroid, which expresses a function of local movement due to breathing and heart pulsations. In some examples, monitoring the centroid locations for intensity variation in infrared images can be more sensitive to motion artifacts than the intensity measurement approach for each of the infrared spot pixel values.

Figure 9:
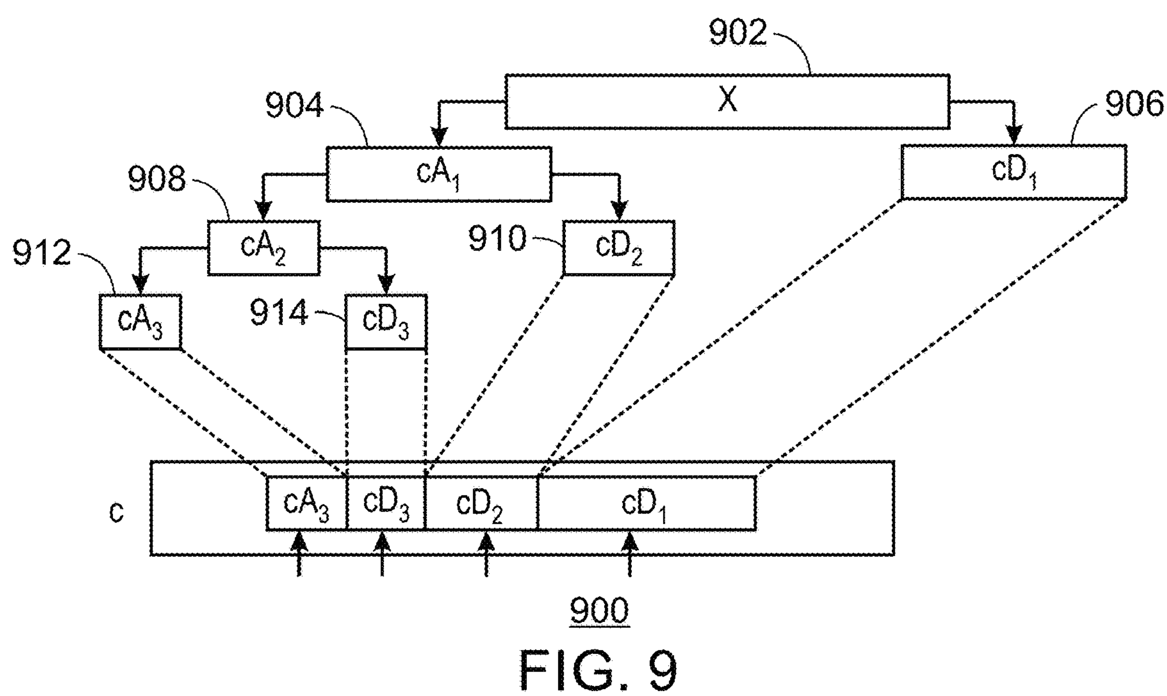
FIG. 9 is an example wavelet packet decomposition technique.

FIG. 9 is an example wavelet packet decomposition technique. In some examples, a wavelet packet decomposition technique can be applied which is illustrated in FIG. 9. In the example wavelet packet 900, there is a 3-level decomposition in which X is the input signal 902, cA1 904 and cD1 906 are the first level of wavelet packet decomposition, cA1 904 is decomposed into cA2 908 and cD2 910 for the second level of wavelet decomposition and cA2 908 is decomposed into cA3 912 and cD3 914 for the third level of wavelet decomposition. The sum of the three levels of wavelet decomposition can reconstruct the original input signal X 902.

In some examples, a detected signal X of length N, a wavelet packet decomposition technique or a discrete wavelet transform can include log 2 N iterations. Starting from X, the first iteration can produce two sets of coefficients: approximation coefficients cA1 904 and detail coefficients cD1 906. In some examples, convolving X with a lowpass filter LoD to produce signal F and a highpass filter HiD to produce signal G, followed by dyadic decimation (downsampling) of signals F and G, results in the approximation and detail coefficients respectively.

In some examples, the length of each filter is equal to 2n. If N=length(X), the signals F and G are of length N+2n−1 and the coefficients $cA_1$ and $cD_1$ are of length $floor_{(N-12)}+n$. The next iteration of the wavelet packet decomposition can split the approximation coefficients $cA_1$ 904 into two parts using the same technique, replacing X with $cA_1$ 904, and producing $cA_2$ 908 and $cD_2$ 910. The wavelet packet decomposition can continue with additional iterations using cA3 912, and any other approximation coefficients for any number of iterations.

In some examples, each level of wavelet decomposition can identify a different motion artifact of a patient such as a movement of the patient's body, a movement due to breathing or a respiration rate, or movement due to a heart rate. In some examples, any number of levels can be used in wavelet decomposition and can identify any number of different motion artifacts, physiological signals of a patient, or the like.

Example Techniques for Detecting Patient Characteristics

In some examples, cameras in an infant care station can obtain depth data, infrared data, RGB data, and the like. A combination of the various sets of data obtained by one or more cameras in an infant care station over a period of time can enable detecting various patient characteristics. For example, the data from cameras in an infant care station can enable identifying a physical size of a patient, a growth rate of a patient, a body position of a patient, emotional or physical responses to stimuli by the patient, and the like.

Figure 10:
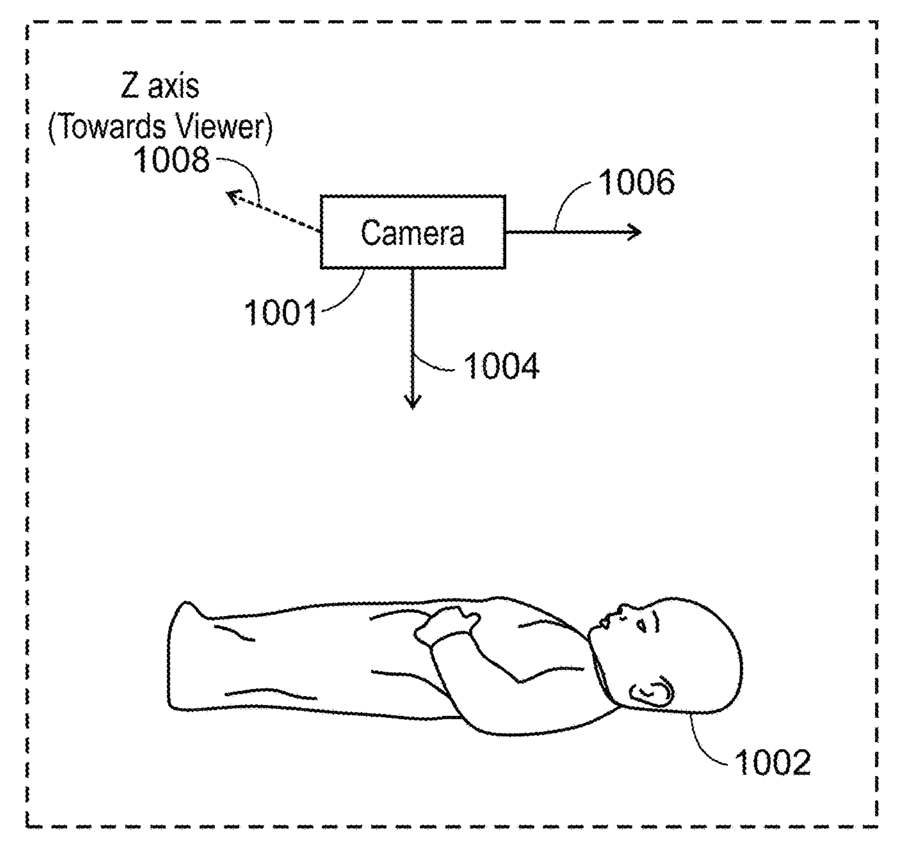
FIG. 10 is an example representation of how depth camera data is obtained from a patient residing in an infant care station.

FIG. 10 is an example representation of how depth camera data is obtained from a patient residing in an infant care station. In some examples, a microenvironment 1000 includes a depth camera 1001 that can capture depth camera data that includes three dimensional data for a patient 1002 in an x direction 1004, a y direction 1006, and a z direction 1008. In some examples, the depth camera data or images can be obtained, captured, or otherwise received from any number of depth cameras 1001 in an infant care station such as the infant care station 200 of FIG. 2.

In some examples, depth camera data collected or obtained from a patient 1002 in a microenvironment 1000 of an infant care station can enable the detection of a sleep wellness assessment of patients, including measurements of time periods of activity versus sleep, and a ratio of activity versus sleep, among others. The depth camera data can also indicate a sleep position balance evaluation on a right side versus a left side of the patient 1002. In some examples, the depth camera data can also indicate a body position or pose of a patient 1002 such as a supine position or a prone position. In some examples, neurological development of a patient 1002 can also be assessed by detecting or identifying facial features, such as whether eyes of a patient 1002 are open or closed during events and periods of time.

In some examples, the depth camera data can also indicate a pain assessment for a patient 1002 in an infant care station based at least in part on detected facial grimace features, mouth open or closed events, restlessness, and crying sounds, among others. The depth camera data can also indicate a detection and alert of seizure activity of a patient 1002 using both severe motion and heart rate elevation, among others.

In some examples, the position of the patient 1002 on a platform of an infant care station can be determined using depth camera data images 1000. The position of the patient 1002 can be used to alert against a patient rolling off an edge of the platform, which can prevent accidental falls or injuries to infant patients. In some examples, the z direction 1008 depth data from the camera's stereo infrared image stream can be used to threshold the known z direction 1008 depth data of a mattress of an infant care station and isolate the graphical vertices that map to the patient's 1002 body from background platform objects. The isolated vertices above a threshold z-level for the mattress, can then provide patient 1002 body location information in an x direction 1004, y direction 1006, and z direction 1008, which define the rectangular boundary of a patient's 1002 body in three dimensional space in relation to the mattress or platform of an infant care station.

Figure 11:
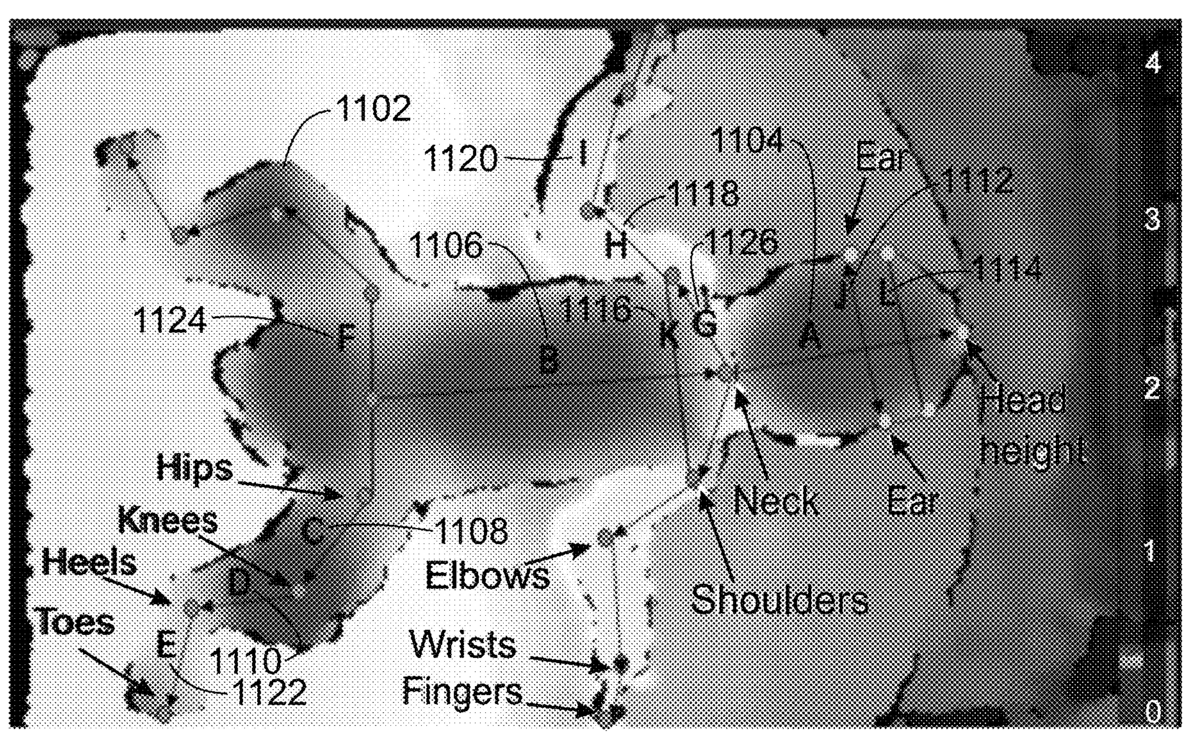
FIG. 11 represents an example image that includes segments of a patient residing in an infant care station.

FIG. 11 represents an example image that includes segments of a patient residing in an infant care station. In some examples, the segmented image 1100 can include any number of segments that represent or identify any number of regions of a patient 1102.

In some examples, a body length of a patient 1102 can be estimated using any suitable camera data, such as the three dimensional data described above in relation to FIG. 10. The body length of a patient 1102 can be estimated from the patient's 1102 body segments, which are defined in three dimensional space for orientation. In some examples, the length of each of the segment's three dimensional vectors can be combined for a total body length. In some examples, segmentation of a patient's 1102 body into vertices can identify peripheral arms, hands, legs, feet, head segment, and body torso, among others, in addition to objects in the view, background mattress, and platform.

In some examples, segmenting the body of a patient 1102 can include identifying or defining boundaries for each segment in three dimensional space. Segmenting a body of a patient 1102 can also include identifying a head orientation of a patient 1102 with point location of ears, a tip of a head, and neck points, among others. Segmenting a body of a patient 1102 can also include identifying points for segments defining shoulders, elbows, wrists, hands, fingers, hips, hip axis mid-point, knees, heels, toes for both right and left side of the body, among others.

In some examples, dynamic allocation of the joint points of a patient's 1102 body can be identified using any suitable artificial intelligence such as deep learning network models, among others. For example, a deep learning network or neural network can be trained using sample data with a user pre-defining the locations of the joints on a measured point cloud of the patient's 1102 body in three dimensional space, images from video frames in two dimensional space, or any combination thereof. User assigned labels to each joint can be defined such as right or left knee, heel, hip, neck, head, shoulder, elbow, hand, eyes, mouth, or nose, among others. In some examples, a deep learning network, such as PointNet or You-Only-Look-Once (YOLO) network type, is trained on the joint locations with user labels, and the trained model is used in real-time or near real-time to dynamically identify the locations of the joints for patients either in three dimensional space on a point cloud (PointNet) or in two dimensional images (YOLO). In some examples, labeled joint points that are identified by the deep learning model can be used to estimate the length of body segments or a total body length of a patient 1102.

As discussed in greater detail below in relation to FIGS. 28-35, in some examples, patient images can be scaled and calibrated to a point cloud dataset so that features in the images are registered with features in the point cloud. If training and classification is done using two dimensional images as input values to the deep learning models, then a two dimensional segment length can be computed, which is an approximation of a three dimensional segment length.

In some examples, segmenting a patient's 1102 body can include identifying a primary vector length for each body segment in 3D vector space. This can be performed using a length equation for two points in 3D vector space in a point cloud described in greater detail below in relation to FIGS. 15-18. In some examples, a point cloud includes point P1 (x1, y1, z1) and point P2 (x2, y2, z2), where a length between P1 and P2 is equal to a square root of ((x2−x1)^2+(y2−y1)^2+(z2−z1)^2). In two dimensional space images, a length between two points, such as Points R1 (x1, y1) and R2 (x2, y2), can be calculated as the square root of ((x2−x1)^2+(y2−y1)^2).

In some examples, summing the segment vector lengths can be used to calculate a patient's unfolded total body length from head to foot as total length of a patient's body. In some examples, adding segments A 1104, B 1106, C 1108, and D 1110 provides an approximation of a total body length of a patient 1102. In some examples, segment B 1106 represents a body length, segment C 1108 represents an upper leg length, and segment D 1110 represents a lower leg length. In some examples, a head length can be defined as segment A 1104, and a head width as segment J 1112. A depth of a patient's head can be estimated from the highest point along forehead line, segment L 1114, and a background platform or mattress. In some examples, segment L 1114 is between the two points defining the forehead where head curvature has a curvature angle that exceeds a predetermined threshold. A shoulder width is estimated as segment K 1116 vector length and an upper arm is estimated as segment H 1118, and lower arm as segment 11120.

In some examples, the corresponding left and right arm segments can be averaged to provide an average estimate, as well as individualized left-side and right-side estimate. Similarly, the corresponding left and right leg segments can be averaged to provide an average estimate, as well as individualized left-side and right-side estimate. Asymmetry between right and left side body part size can be used to indicate localized differences.

In some examples, hand length values can be estimated as a distance between a tip of a hand's fingers and a wrist point and feet length values can be estimated between a front tip of a patient's toes and a heel's surface or segment E 1122. Segment F 1124 can represent a width of a patient's 1102 hips and segment G 1126 can represent a size of a patient's 1102 neck. In some examples, any number of additional segments can be determined or calculated for a patient 1102.

Figure 12:
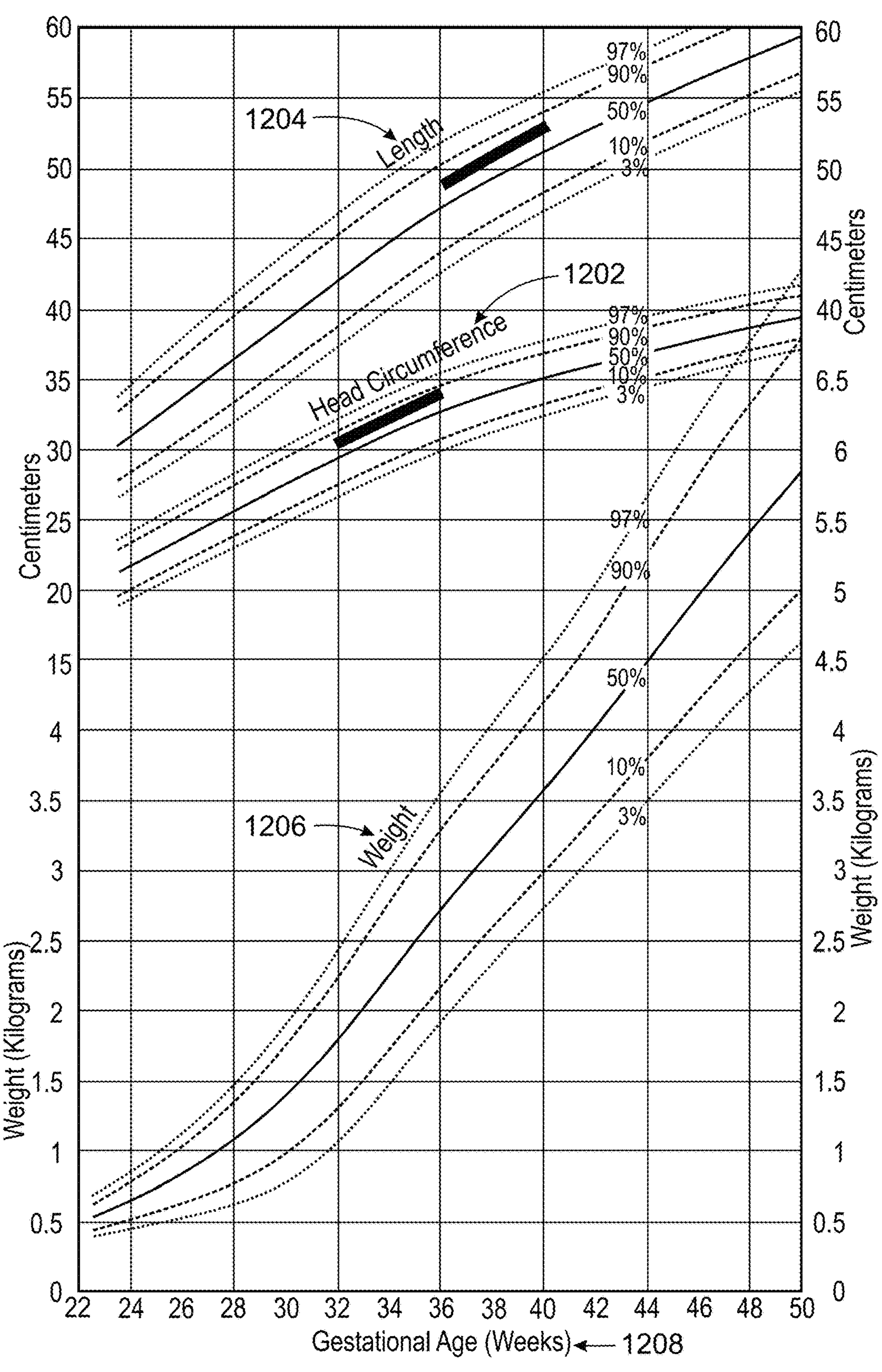
FIG. 12 is an example growth chart generated by measurements of a patient in an infant care station over time.

FIG. 12 is an example growth chart generated by measurements of a patient in an infant care station over time. In some examples, a growth chart 1200 can provide a representation of growth data for pre-term infants and term infants in order to provide a context for growth relative to a population distribution.

In some examples, growth development charts 1200 can be automatically created with measurements obtained from a camera. The measurements can include a head circumference 1202, body length 1204, or weight 1206, among others, measured based on gestational age 1208 of a patient. The distribution quarterly percentiles, mean, and standard deviation values can also be defined using accumulative data across groups of patients based on data obtained using camera systems. The data from a patient group can be collected across time and aggregated or compiled to form a population database for generating expected growth distributions. Rather than relying on a distribution based on a small sample size or patient in a single region, the growth data determined based on camera data can generate a growth chart based on a large sample size across multiple regions, geographic areas, and the like. In some examples, growth charts can also be generated for patients that share a trait such as a shared birth region, shared family traits, or the like for normalized growth chart to a particular shared characteristic among the patients, referred to as a group class. This enables increase specificity (or relevance), and enhanced growth sensitivity to the mapping of a patient's growth relative to the patient's group class. Furthermore, population growth charts can be developed for more specific body segments such as the arms, legs, shoulders, waist, among others, or total body volume or total body surface area.

Figure 13:
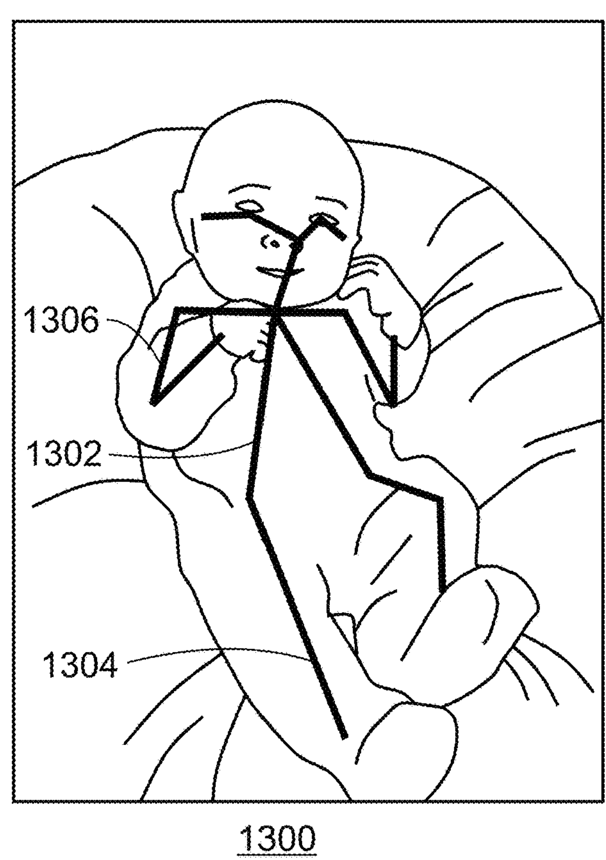
FIG. 13 is an example image of an infant patient with overlayed segments.

FIG. 13 is an example image of an infant patient with overlayed segments. In some examples, an image 1300 can be of any suitable patient in an infant care station, such as the infant care station 200 of FIG. 2. The image 1300 can also represent one or more patients in any suitable environment.

In some examples, any number of segments indicating a length between points in three dimensional space can be incorporated into the image 1300. For example, segments indicating a body length 1302, leg length 1304, arm length 1306, and the like can be added or otherwise overlaid on an image 1300 of a patient. In some examples, any of the segments described above in relation to FIG. 11 can be incorporated into image 1300, among other segments.

Figure 14:
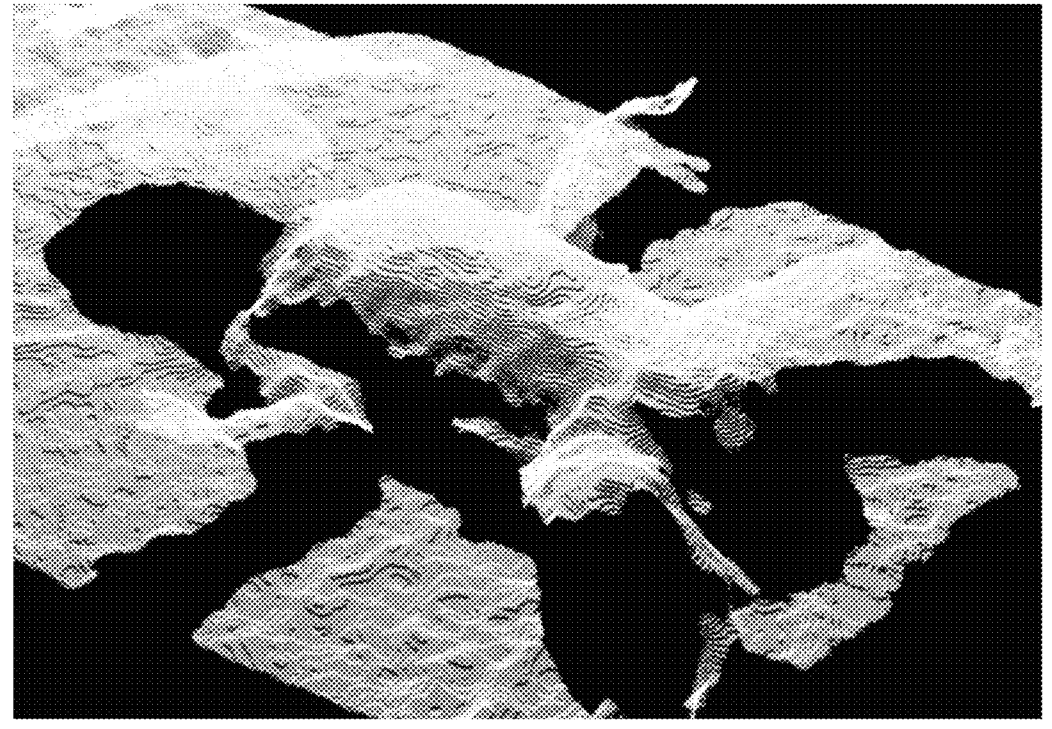
FIG. 14 is an example point cloud representing the body of a patient in an infant care station.

FIG. 14 is an example point cloud representing the body of a patient in an infant care station. In some examples, the point cloud 1400 can be used as a finite element model to estimate a patient's body volume and body surface area. In some examples, the patient's body volume and surface area can be monitored to develop projections or trends over time to indicate a patient's growth profile. In some examples, the estimated baby's body volume and externally measured body weight can be used to evaluate an average body's density. A weight of a patient can be estimated as equal to a volume multiplied by density, or estimated density can be equal to weight divided by volume. A measurement of density of a patient can be trended over time and used as an indicator of fluid retention or fluid dehydration, among others. Total body or body part's volume and surface area can be used to assessing inflammatory responses including allergic reactions.

Variable body poses of an infant can be mapped into a reference body shape that is defined per a skeletal model. This is generated by interpolation of movements across different body poses into the desired reference body shape.

This interpolation helps in mapping repeated iterative scans of the body from different perspectives, generating point cloud per each scan, and mapping these point clouds into the same skeletal model format in order to complete the model data representation. In some examples, a reference body shape can be used on repeated point cloud scans or point cloud 1400 to build a more complete model of the body of a patient using registered point cloud data sets that are dynamically obtained over time with a depth camera. The registration of multiple views can include the head and trunk of a patient since the head and trunk are generally more rigid areas of a body rather than arms and legs, which are flexible.

Registration of point clouds across time can correct for the rotation and translation effects using a standard transformation matrix for 3D objects. This transformation matrix can be computed by iterative optimization using a registration algorithm such as an iterative closest point (ICP) algorithm, or any other suitable technique.

Figure 15:
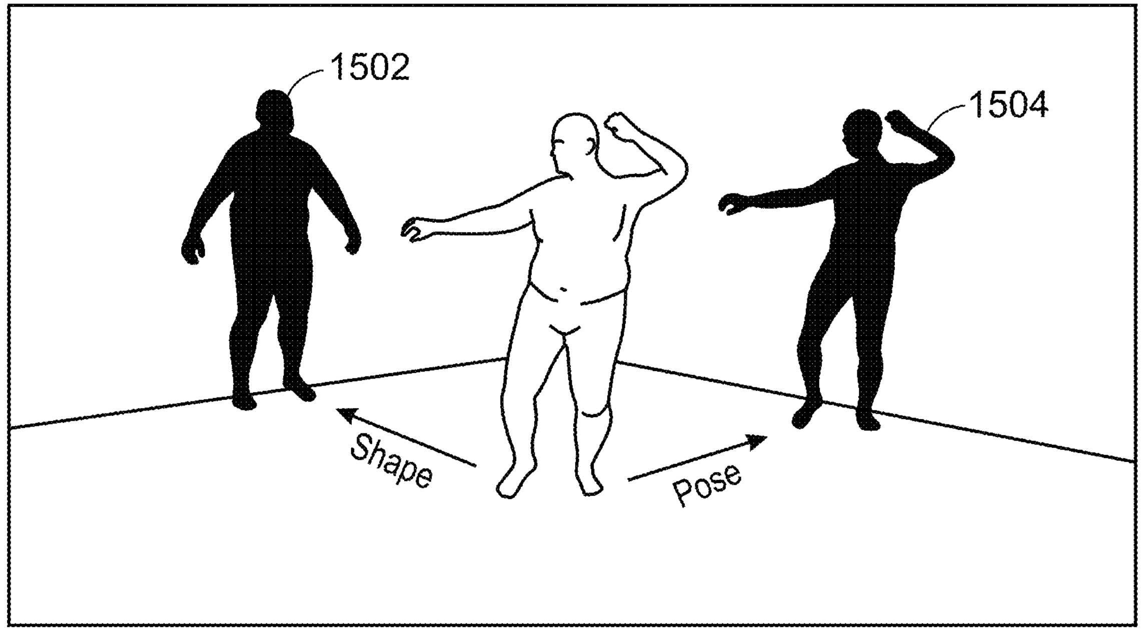
FIG. 15 is an example image of a body pose of a patient.

FIG. 15 is an example image of a body pose of a patient. In some examples, point cloud data can be aggregated to represent a body shape 1502 in a fixed reference shape that can be used further to fit a mesh surface through the point cloud using Delaunay surface triangulation or any other suitable technique.

In some examples, body segments between joints in two dimensional space or three dimensional space can be used to estimate the body pose 1504 of a patient in 2D or 3D. The pose 1504 can be constructed using a skeletal segment model which offers a current position of the body. In addition, a reference body shape 1502 can also be constructed from current body pose 1504 by linearly interpolating the body segments position onto the reference body shape, which provides a reference skeletal model.

Figure 16:
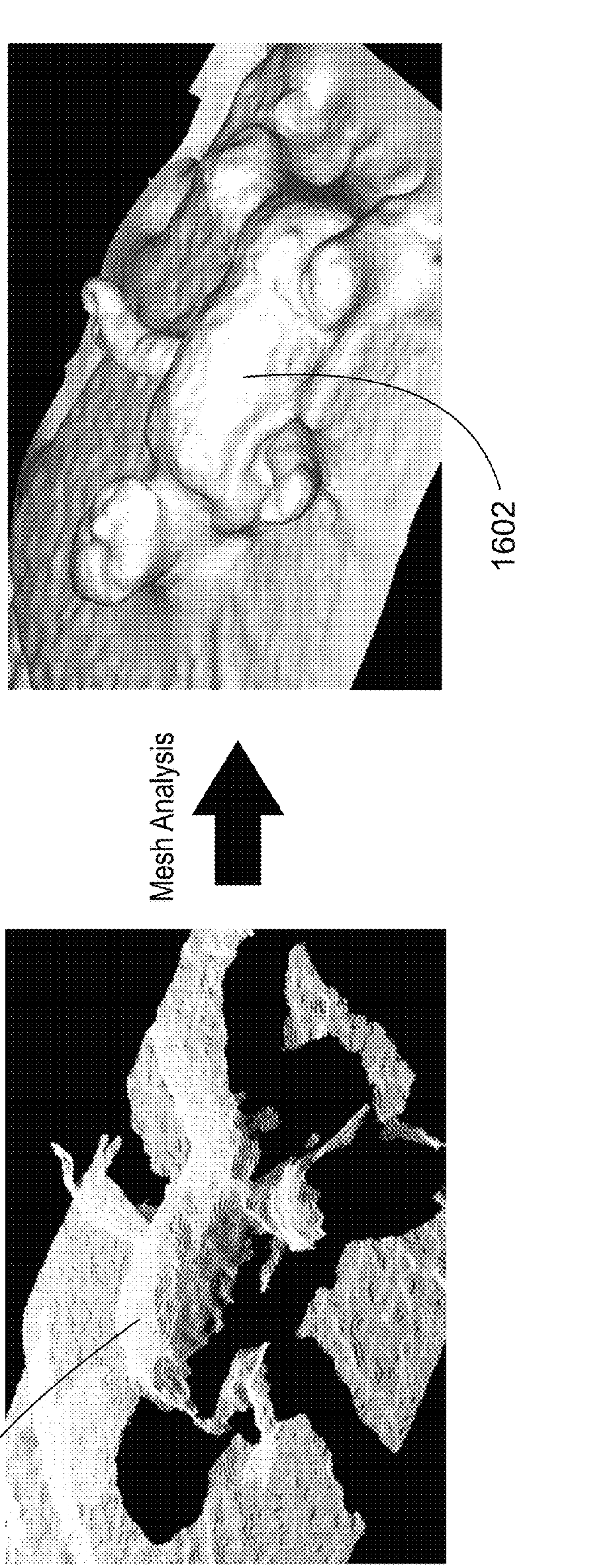
FIG. 16 is an example of a mesh point cloud surface.

FIG. 16 is an example of a mesh point cloud surface. In some examples, a point cloud 1600 can be processed to form a mesh point cloud surface 1602 by fitting a mesh surface through the point cloud using Delaunay surface triangulation, or any other suitable technique. The mesh point cloud surface 1602 can include a higher density of data values representing a three dimensional shape and size of a patient.

The point cloud 1600, as referred to herein, represents data values, such as XYZ vertices, obtained, received, or otherwise determined by a camera using one or more depth measurements. The mesh point cloud surface 1602 or mesh point cloud represents both vertices and a processed triangulated surface that is generated or calculated based at least in part on the point cloud 1600 to represent a solid surface.

Figure 17:
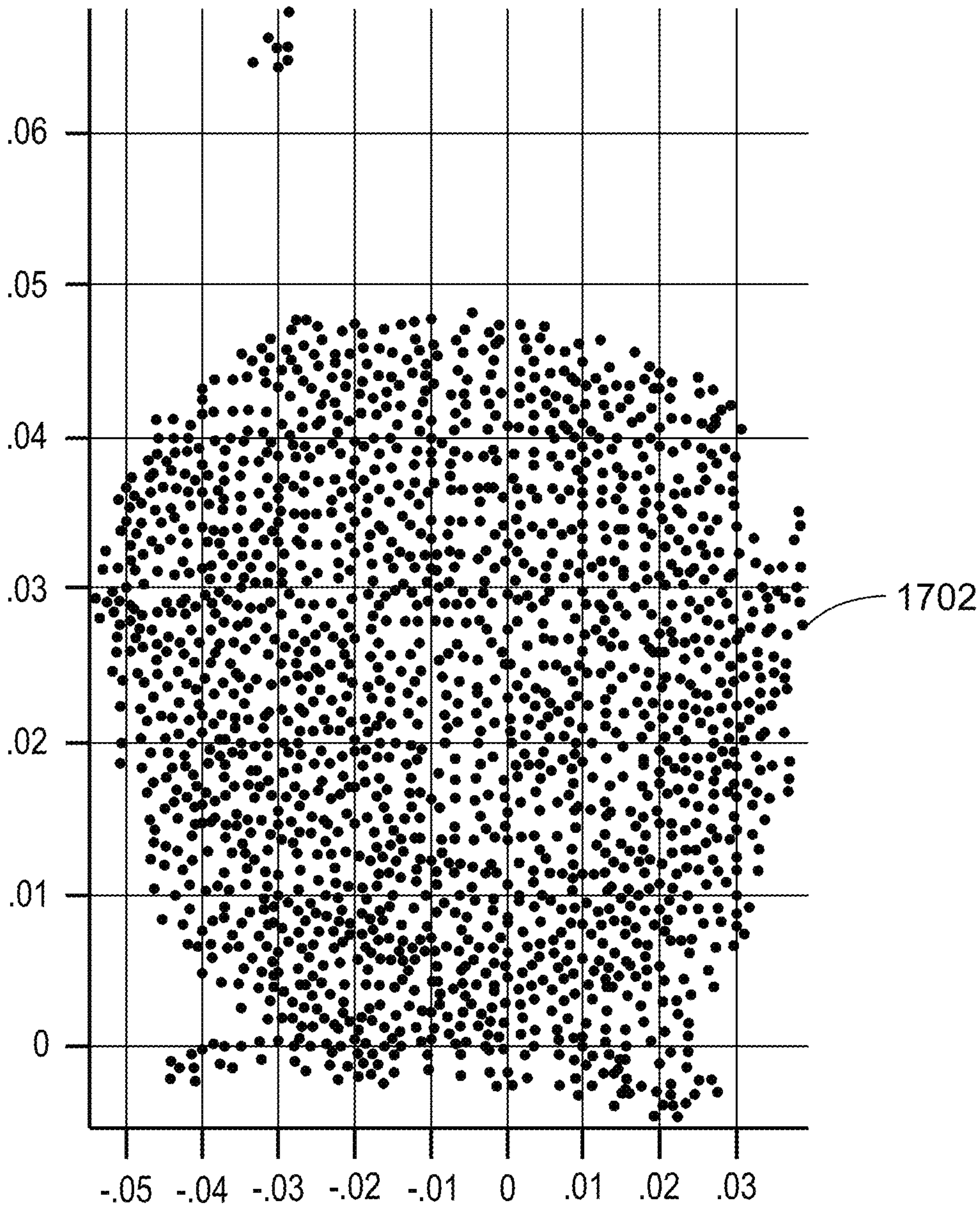
FIG. 17 is an example mesh point cloud of a head of a patient obtained while the patient is in an infant care station.

FIG. 17 is an example mesh point cloud of a head of a patient obtained while the patient is in an infant care station. The mesh point cloud 1700 illustrates a two dimensional distance between various data values 1702 representing the head of a patient. In some examples, the mesh point cloud 1700 can include any number of points 1702 obtained from a point cloud. The mesh point cloud 1700 can represent any portion of a patient in three dimensional space, such as a torso, limb, or the like. The mesh point cloud 1700 can provide a three dimensional distance between any number of points 1702 within a single portion of a patient or between multiple different portions of a patient, such as a distance from a head to a leg, or the like.

Figure 18:
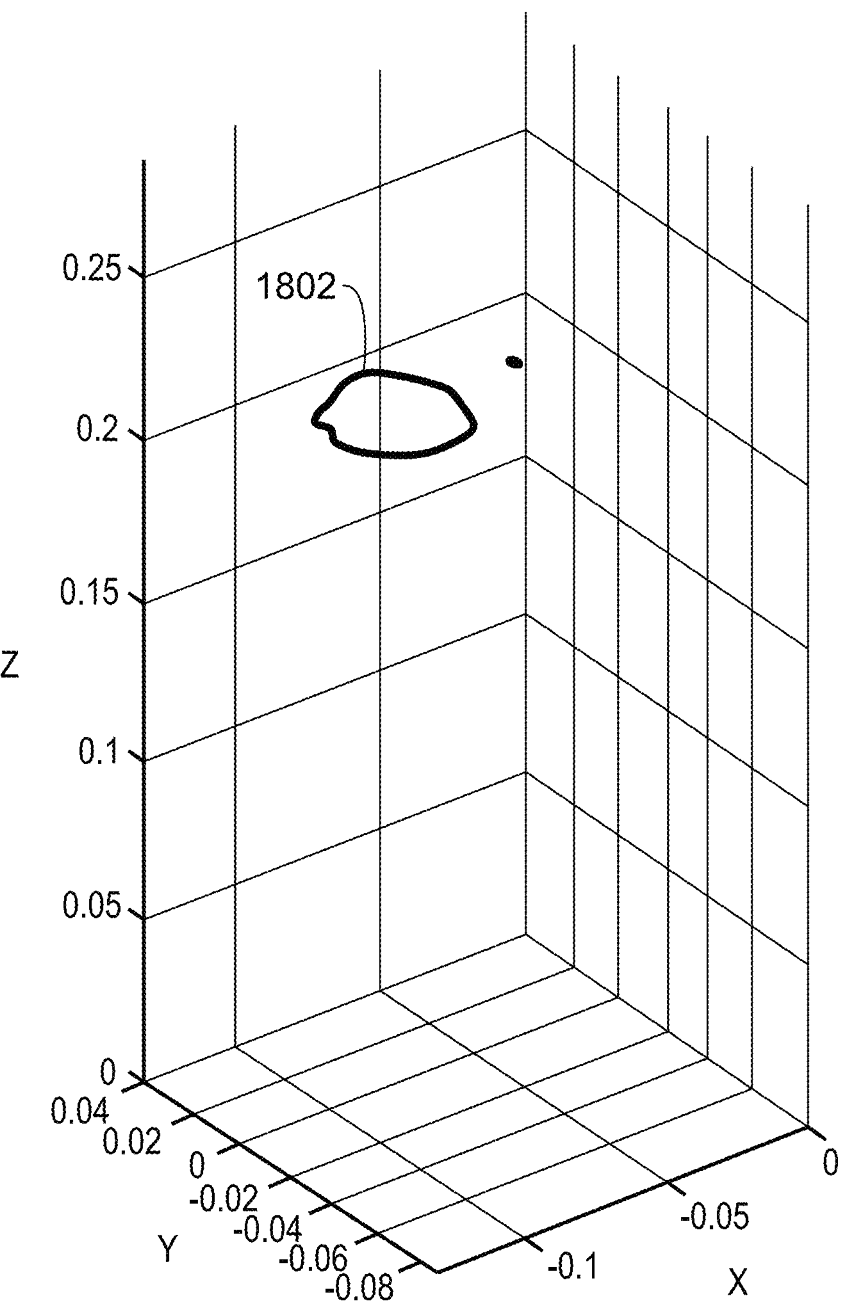
FIG. 18 is an example estimation of a segment of a patient in three dimensional space.

FIG. 18 is an example estimation of a segment of a patient in three dimensional space. In some examples, a head circumference 1802 can be measured and displayed using a three dimensional representation 1800 as a clinical indication of a patient's growth profile. The head circumference 1802 can be estimated from the point cloud data in three dimensional space using a cross-sectional view with a level plane measured across a head point cloud above the eyes of a patient. In some examples, the length of the resulting curved line representing the head circumference 1802 is calculated as an integral sum of the point-to-point segment lengths in 3D space for the points in the segment. In some examples, a point cloud or mesh point cloud surface can be used to determine or calculate any other suitable characteristics for a patient's growth profile such as an arm length, a leg length, a torso length, or the like.

Figure 19:
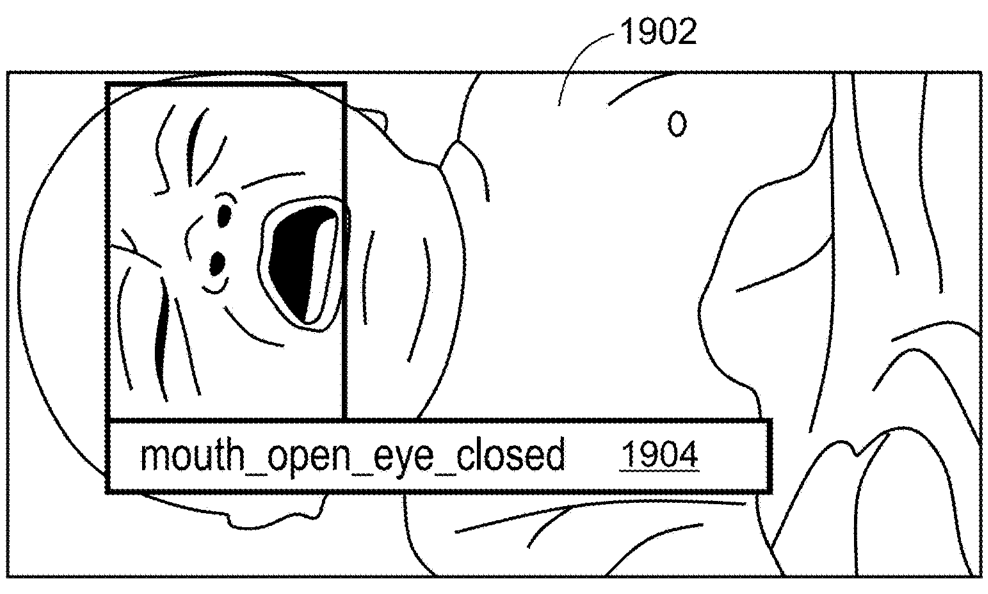
FIG. 19 is an example image of detected facial features.

FIG. 19 is an example image of detected facial features. The example image 1900 includes a portion of a patient's torso 1902 and a patient's facial features 1904. In some examples, the patient's facial features 104 can include eyes, a nose, mouth, or ears, among others.

The patient's facial features 1904 can be detected using either a red-green-blue image, an infrared image, depth vertices information, or a combination thereof. In some examples, the location of facial features 1904 can be used for detection of facial expressions such as whether eyes are open or closed, whether a mouth is open or closed, among others. The facial expressions can be used to determine a patient's active versus sleep periods. In some examples, the facial expressions can also be used to determine a pain response that results in a facial grimace.

The facial features 1904 can be detected using image series from red-green-blue images or infrared images from video streams by training a deep learning model, such as a You-Only-Look-Once (YOLO) type deep learning model, on the location of a face, mouth, and eyes within an image 1900. In some examples, localization of eyes and mouth within the boundary of the detected face region is enforced to ensure accuracy of localization eyes and mouth detection given variable interfering objects or noise in the view. As discussed in greater detail below in relation to FIGS. 28-35, a deep learning model to detect facial features in images can be developed using supervised training with labeled ground truth images for a variety of patient images, wherein the images are labeled for facial features including a face region, an eyes region, and a mouth region, among others. In some examples, a rectangular region of interest (ROI) can be applied for each facial feature 1904. The trained model can be tested with a separate image series for detection of a region that includes facial features such as eyes and a mouth.

Figure 20:
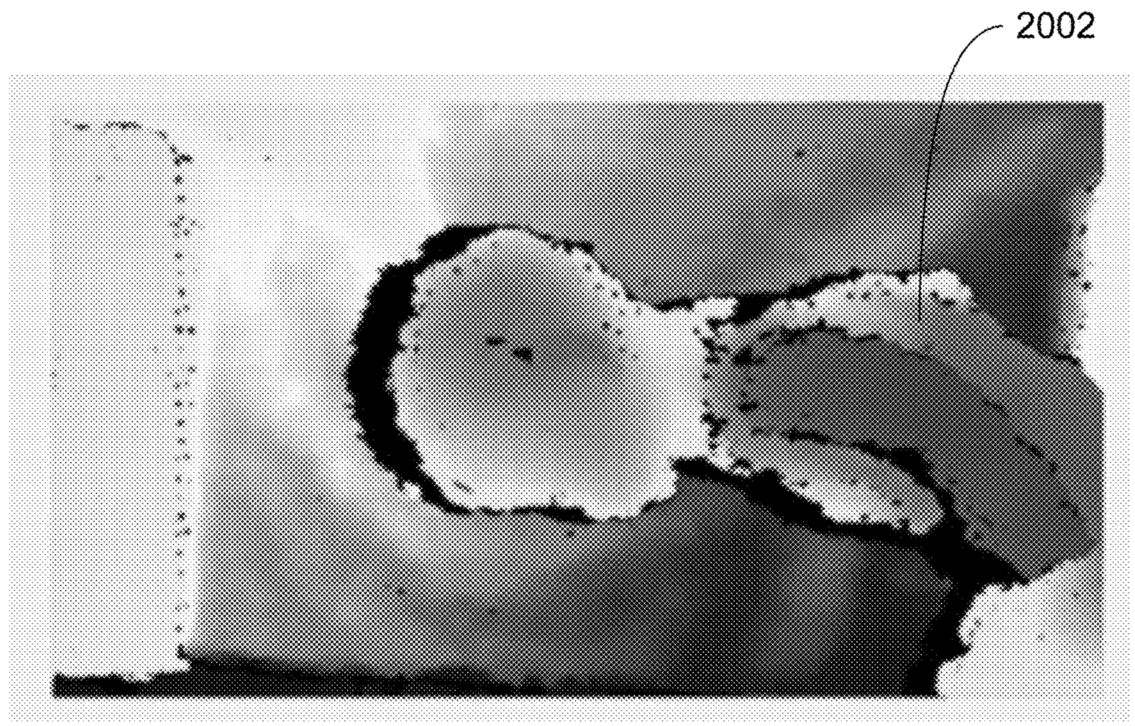
FIG. 20 is an example infrared image of a patient in an infant care station.

FIG. 20 is an example infrared image of a patient in an infant care station. Based on features of the head, torso, and limbs of the patient 2002, the infrared image 2000 can indicate that a patient 2002 is lying on the patient's right side.

In some examples, a patient's 2002 head horizontal vector may be at an angle relative to a horizontal vector of the patient's 2002 body in the body's plane. This can be due to placement of a pillow or tilt of the head relative to the body due to the neck segment. In some examples, facial features, as well as a location of arms and legs and body width, can be used to determine if a patient 2002 is sleeping supine, on a right-side, on a left-side, or in a prone position and for how long of a duration. This information can be trended and displayed to help the caregiver achieve a more balanced sleeping poses, to avoid skeletal shape deformations in neonates.

In some examples, techniques herein can label regions, such as a head, face, or the like, of a patient with bounding boxes. The bounding boxes can label any suitable region of a patient in three dimensional space. In some examples, the labels or bounding boxes are used to train a machine learning technique, such as a PointNet++ (PointSeg) deep learning model, to identify the desired head and joints from different poses of a patient. For example, the bounding boxes can label regions of a patient corresponding to requested body parts in a supine, prone, left, or right position, among others. In some examples, a location of joint labels of a patient can enable determining a baby length as a distance between the joints as calculated using 3D vector math. In some examples, labeling a head point cloud with a bounding box can enable registering the multiple pose views of the head of a patient to create a more complete head model for purposes of measuring the circumference of the head.

Figure 21:
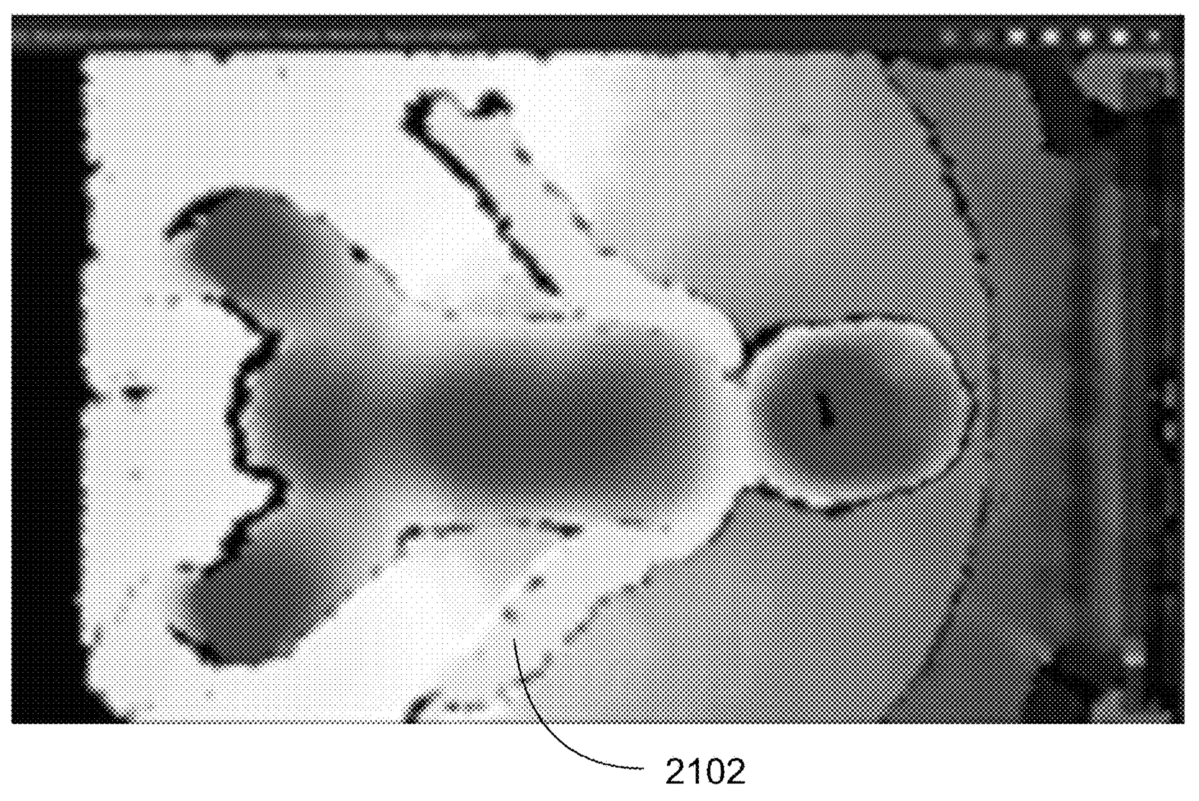
FIG. 21 is an example infrared image of a patient in an infant care station.

FIG. 21 is an example infrared image of a patient in an infant care station. Based on features of the head, torso, and limbs of the patient, the infrared image 2100 can indicate that a patient 2102 is lying on the patient's back in a supine position. As discussed above in relation to FIG. 20, the patient 2102 lying in a supine position can be determined based on a position of the patient's 2102 head in relation to the patient's 2102 body, a position of the patient's 2102 head in relation to the patient's 2102 torso or limbs, or the like.

FIGS. 22A-22D are example images of patients in an infant care station with different levels of light, with or without blankets, and the like.

Figures 22A, 22B, 22C, 22D:
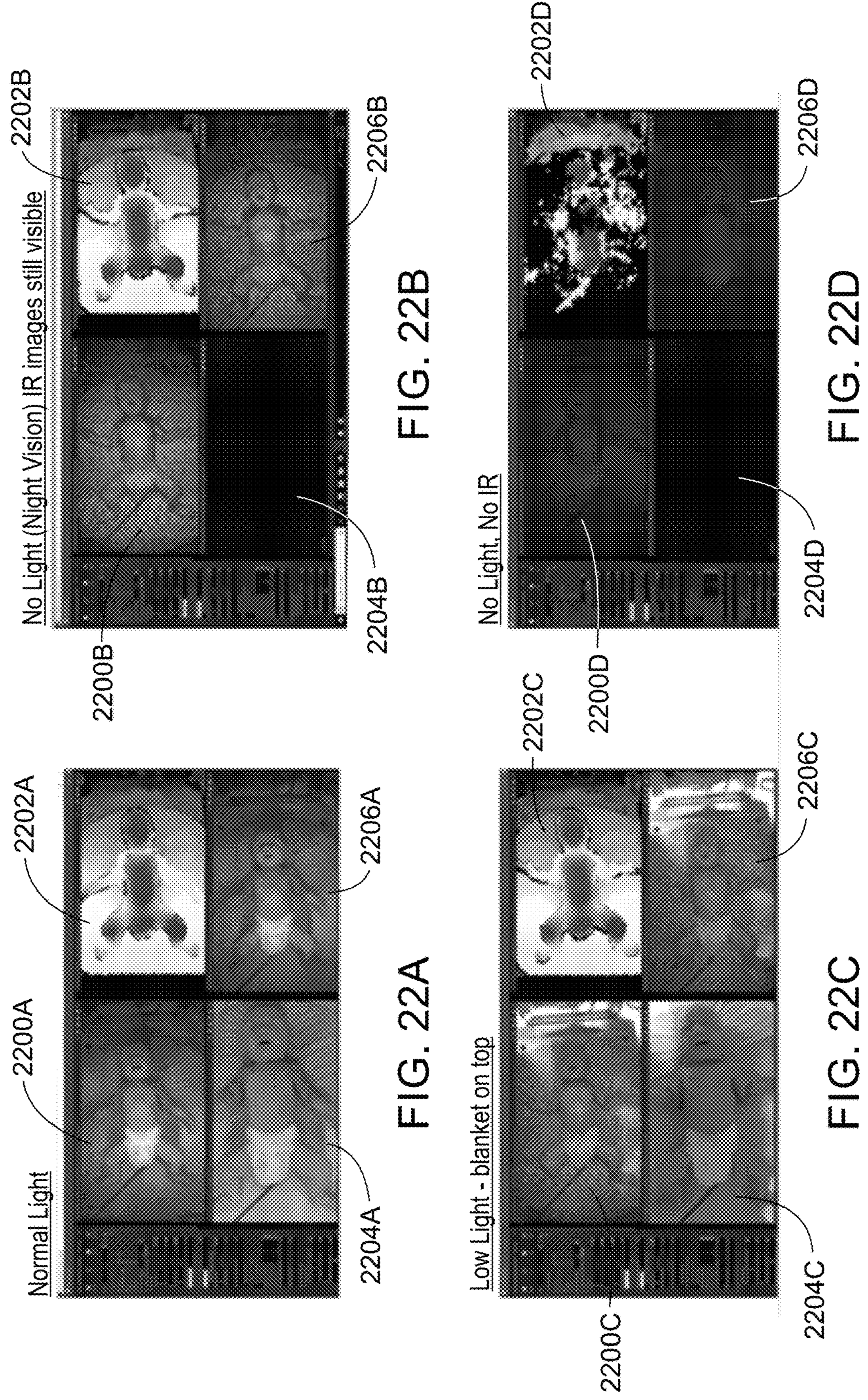

In FIG. 22A, the images 2200A, 2202A, 2204A, and 2206A of a patient are captured with an ambient light source at light levels within a predetermined expected luminosity range, as well as with an infrared light source. In some examples, the predetermined range can represent expected light conditions in a hospital setting or any suitable setting for an infant care station. The images 2200A and 2206A represent IR images which enable night vision, image 2204A represents an RGB image with ambient light, and image 2202A represents a depth heatmap image of the depth point cloud data.

In FIG. 22B, the images 2200B, 2202B, 2204B, and 2206B of a patient are captured with no ambient light and only using an infrared light source for night vision, which does not affect the ability to capture infrared images. The images 2200B and 2206B represent left and right IR images of a stereo depth imager, respectively, with night vision, image 2204B represents an RGB image with ambient light, and image 2202B represents a depth heatmap image of the depth point cloud data.

In FIG. 22C, the images 2200C, 2202C, 2204C, and 2206C are captured with a blanket on top of the infant care station, with an ambient light source, a typical practice in neonatal care setting, and an infrared light source present. The images 2200C and 2206C represent the left and right IR images of a stereo depth imager, respectively, with night vision, image 2204C represents an RGB image with ambient light, and image 2202C represents a depth heatmap image of the depth point cloud data.

In FIG. 22D, the images 2200D, 2202D, 2204D, and 2206D are captured with no ambient light source or infrared light source. The images 2200D and 2206D represent the left and right IR images of a stereo depth imager, respectively, with night vision, image 2204D represents an RGB image with ambient light, and image 2202D represents a depth heatmap image of the depth point cloud data.

In some examples, using infrared images for depth and motion analysis is advantageous because the infrared images enable night-vision video capture. RGB video stream imaging capability can be affected by ambient lighting conditions, while infrared imaging is generally controlled using the infrared LED light intensity. In neonatal care units (NICU), an infant care station may be covered with a blanket to promote better sleep, or the ambient light may be dimmed for the entire room. Having an infrared light source in the camera enables continuous image acquisition that is unaffected by ambient lighting conditions.

Figure 23:
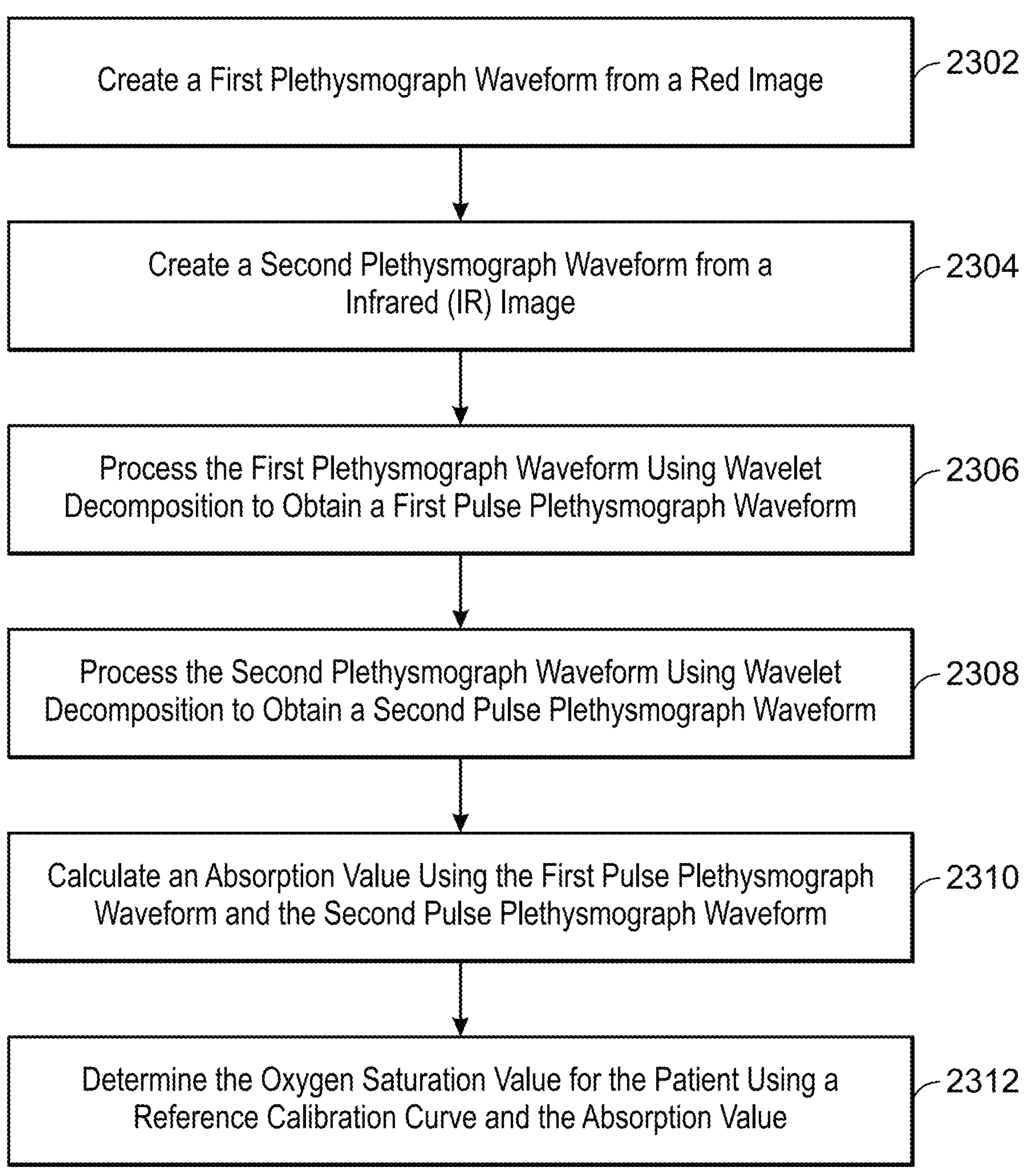
FIG. 23 depicts a process flow diagram for an example method for detecting an oxygen saturation level for a patient.

FIG. 23 depicts a process flow diagram for an example method for detecting an oxygen saturation level for a patient. In some examples, the method 2300 can be implemented with any suitable device, such as the infant care station 200 of FIG. 2, among others.

At block 2302, the method 2300 can include creating a first plethysmograph waveform or red plethysmograph waveform from a red image. The red image can be any suitable image of a patient with the blue and green color values removed. For example, the red image can be a red-green-blue image in which only the red color values are captured or stored for analysis. In some examples, the red image of the patient includes a portion of exposed skin from a forehead of the patient, an abdomen, or chest of the patient, among others. The red values of the exposed skin can be used to detect an oxygen saturation level for the patient as described in greater detail below in relation to blocks 2302-2312.

A plethysmograph waveform, as referred to herein, can include any suitable signal, time series of data values, or the like that represents one or more characteristics of a patient. The characteristics can include a heart rate, a respiratory rate, motion of the patient, or the like. The first plethysmograph waveform can be created from a red image segment that is focused on the exposed skin area to be analyzed, a region of interest (ROI), by summing the pixel intensity values in the ROI for a particular image frame for measures of sum total of pixel intensity value, average value, median value, or the like. That ROI is tracked across image time series frames and in each frame the intensity values of ROI is computed using measures of the sum total of pixel intensity values, mean values, median values, or the like within the ROI. These measures are trended over time across each of the available time frames in the image series of a video to form the first Plethysmograph pulse signal being analyzed for Pulse Oximetry.

At block 2304, the method 2300 can include creating a second plethysmograph waveform or infrared plethysmograph waveform from an infrared (IR) image. The second plethysmograph waveform can be calculated or determined by converting pixel values of an infrared image into a plethysmograph waveform. An infrared image segment that is focused on the exposed skin area to be analyzed, a region of interest (ROI), by summing the pixel intensity values in the ROI for a particular image frame for measures of sum total of pixel intensity value, average value, median value, or the like. That ROI is tracked across image time series frames and in each frame the intensity values of ROI is computed using measures of the sum total of pixel intensity values, mean values, median values, or the like within the ROI. These measures are trended over time across each of the available time frames in the image series of a video to form the second Plethysmograph pulse signal being analyzed for Pulse Oximetry.

At block 2306, the method 2300 can include processing the first plethysmograph waveform using wavelet decomposition to obtain a first pulse plethysmograph waveform. For example, the method 2300 can include separating the first plethysmograph waveform using wavelet decomposition techniques into two (or more) components, wherein the components include at least a pulse plethysmograph waveform, a respiration rate plethysmograph waveform, and a time series for motion artifacts or undesired noise.

At block 2308, the method 2300 can include processing the second plethysmograph waveform using wavelet decomposition to obtain a second pulse plethysmograph waveform. In some examples, wavelet decomposition can separate the second plethysmograph waveform into two (or more) components, wherein the components include at least a pulse plethysmograph waveform, a respiration rate plethysmograph waveform, and a time series of motion artifacts or undesired noise.

At block 2310, the method 2300 can include calculating an oxygen absorption value using the first pulse plethysmograph waveform and the second pulse plethysmograph waveform. In some examples, the oxygen absorption value can be calculated using any suitable technique, such as ratio of the normalized red intensity to the normalized infrared intensity.

For example, an oxygen absorption value or an oxygen saturation value can be computed as a function of $(\text{Red Image}_{AC}/\text{Red Image}_{DC})/(\text{Infrared}_{AC}/\text{Infrared}_{DC})$, where AC represents an amplitude of pulsations (valley to peak) in a plethysmograph waveform and DC represents a baseline offset level of the plethysmograph trend of the plethysmograph waveform, such as an average of an input signal for a period of time. The first ratio of AC to DC value can be used for normalization for each of the Red and Infrared signals for their variable amplitude component representing the pulsatile part over their baseline offset level representing the overall light absorption intensity values. The division of Red to Infrared ratios allows relative absorption of intensity computation since Oxygenated Hemoglobin (which tends to be brighter red in color) absorbs Infrared more than Deoxygenated hemoglobin (which tends to be darker red in color).

In some examples, the method 2300 can analyze the light absorption of two wavelengths, such as red and infrared, from a pulsatile component of oxygenated arterial blood normalized by the averaged trend value (AC/DC). The averaged trend value can be used to estimate the absorption ratio (402) using a reference calibration curve. The red video image stream channel can be used to construct the red plethysmograph, and the infrared video image stream channel can be used to construct the infrared plethysmograph. The ratio of the normalized (AC/DC) value for both red and infrared constructed plethysmographs can be obtained and related to 402 values using a reference calibration curve.

In some examples, a measurement of pulse oximetry can be determined by comparing the red pixel stream from red-green-blue (RGB) video and a corresponding infrared image pixel stream from an infrared video stream for the same localized feature in the image field showing exposed skin for a patient or neonate. In some examples, the exposed skin can include a portion of a forehead, among other areas. The two images, RGB and infrared, each provide a sensing source for a pulse plethysmograph waveform, which can be constructed from the dynamic variation over time for these pixel values. The total, average or median intensity value for a small skin region of interest (ROI), for example on the forehead, can be computed and tracked over time to construct the plethysmograph from each video stream. In some examples, a signal can be used to compute a heart rate.

At block 2312, the method 2300 can include determining the oxygen saturation value for the patient using a reference calibration curve and the absorption value. The reference calibration curve can be obtained or detected from a remote pulse oximetry device with an accuracy above a predetermined threshold. The absorption values of the camera of an infant care station can be compared to the reference values from the remote pulse oximetry device and a reference calibration curve can be generated or calculated as an offset for the absorption values of the cameras of the infant care station as compared to the absorption values of the remote pulse oximetry device. The resulting oxygen saturation level is the output of the absorption values adjusted using the reference calibration curve, which results in oxygen saturation values that have an accuracy above a predetermined threshold.

In some examples, a constant illuminating light source can be included in an infant care station to enable SpO2 measurement, similar to the infrared LED light source. The red LED light source can provide light for the red images regardless of ambient light conditions. In some examples, detection of occlusion in circulation of a patient can be enabled by performing pulse oximetry over multiple areas of the body of the patient. Poor peripheral circulation can be detected by comparing 402 values detected with a forehead of a patient and legs or arms of a patient. Poorer blood circulation can be detected as a result of a significant pulse oximetry delta or differential between a target tissue, such as a leg, among others, and a reference tissue, such as a forehead, among others. In some examples, poor circulation can be the result of a partially occluded blood vessel or a weaker cardiac muscle. In some examples, the techniques herein can detect congenital cardiac diseases that affect the circulatory pathways of the heart, such as patent ductus arteriosis (PDA) that can affect blood circulation efficiency. In an example, a pulse plethysmograph signal can be measured at a high frame rate of the camera to provide for high resolution timing of pulsation peaks. This high-resolution plethysmography signal or transit plethysmography signal when measured in two locations (stereo) such as centrally on the chest, abdomen, or face, and peripherally such as on an arm, hand, leg, or foot, can provide for differential measurement of pulse transit time between the central location and the peripheral location. The pulse transit time variability is valuable as it provides a correlating indication to relative blood pressure changes. Blood pressure is difficult to obtain in neonates and newborns due to their small size and fragility against using blood pressure cuffs. This camera based derivation of pulse transit time can therefore serve as a proxy for direct for blood pressure measurement.

In some examples, the method 2300 can include obtaining the first red plethysmograph waveform from the red image and the second IR plethysmograph waveform from the IR image, wherein the red image and the IR image are captured from one or more regions of the patient. Additionally, the method 2300 can include calculating separate oxygen saturation values for each of the different regions using the first red plethysmograph waveform and the second IR plethysmograph waveform and generating a relative value representing a difference between the oxygen saturation values for each of the different regions. In some examples, both red images and infrared images can be a source of pulse plethysmographs.

In some examples, the method 2300 can include obtaining the first plethysmograph waveform from the red image and the second plethysmograph waveform from the IR image, wherein the red image and the IR image are captured from one or more regions of the patient. Additionally, the method 2300 can include calculating separate heart rate values for each of the different regions using the first plethysmograph waveform and the second plethysmograph waveform and generating a relative value representing a difference between the heart rate values for each of the different regions.

In some examples, the method 2300 can include obtaining the first plethysmograph waveform from the red image and the second plethysmograph waveform from the IR image, wherein the red image and the IR image are captured from one or more regions of the patient. Additionally, the method 2300 can include calculating separate respiration rate values for each of the different regions using the first plethysmograph waveform and the second plethysmograph waveform and generating a relative value representing a difference between the respiration rate values for each of the different regions.

The process flow diagram of method 2300 of FIG. 23 is not intended to indicate that all of the operations of blocks 2302-2312 of the method 2300 are to be included in every example. Additionally, the process flow diagram of method 2300 of FIG. 23 describes a possible order of executing operations. However, it is to be understood that the operations of the method 2300 can be implemented in various orders or sequences. In addition, in some examples, the method 2300 can also include fewer or additional operations. For example, the method 2300 can include processing a first pulse plethysmograph waveform to obtain a peak to peak interval indicating a first heart rate (HR) value and processing a second pulse plethysmograph waveform to obtain a peak to peak interval indicating a second heart rate (HR) value. In some examples, the method 2300 can include combining the first HR value and the second HR value to form an average heart rate value.

In some examples, the method 2300 can include determining the oxygen saturation value from the abdomen of the patient and determine a second oxygen saturation value from the forehead of the patient, comparing the oxygen saturation value and the second oxygen saturation value, and determining a relative difference between the oxygen saturation value from the abdomen and the second oxygen saturation value from the forehead, wherein the relative difference indicates a disease state.

Figure 24:
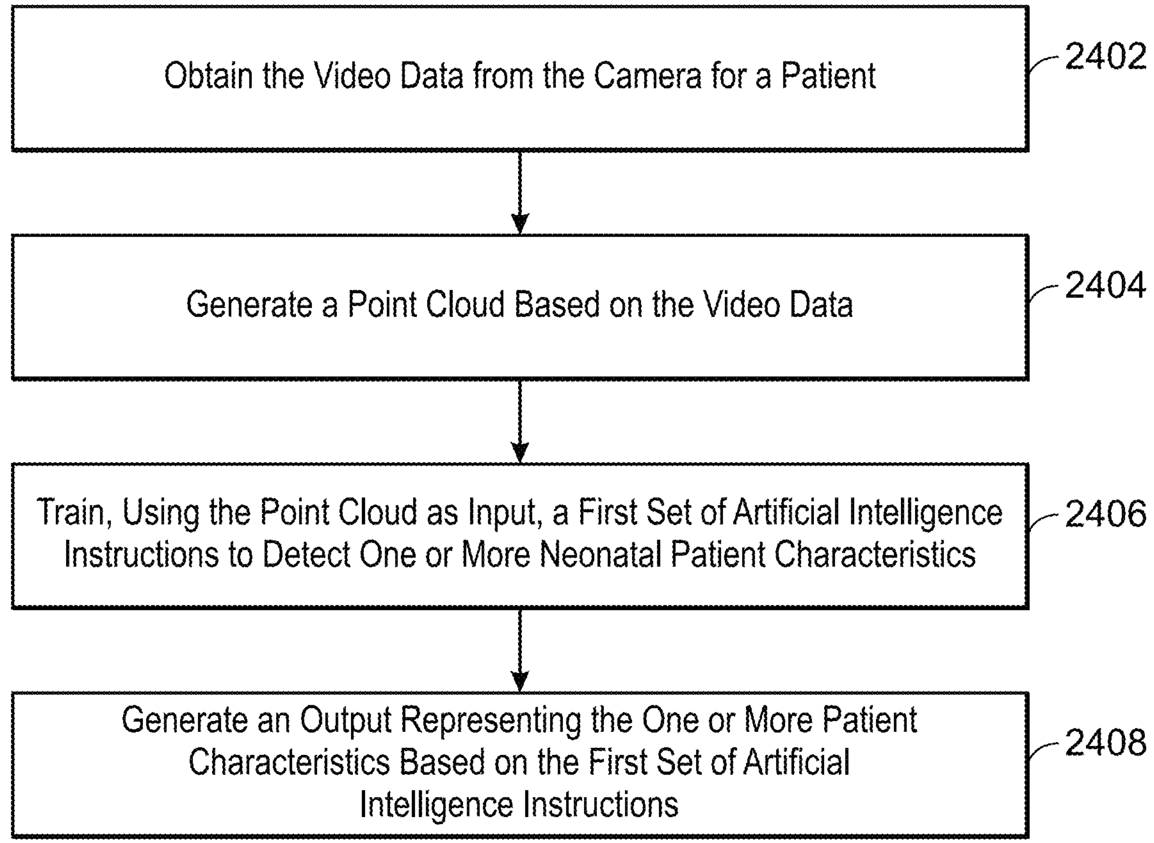
FIG. 24 depicts a process flow diagram of an example method for detecting a patient characteristic.

FIG. 24 depicts a process flow diagram of an example method for detecting a patient characteristic. In some examples, the method 2400 can be implemented with any suitable device, such as the infant care station 200 of FIG. 2, among others.

At block 2402, the method 2400 can include obtaining the video data from the camera for a patient. In some examples, the video data can include an image stream of an enclosure of an infant care station. For example, the video data can include any number of images captured or obtained over a period of time of a mattress of an infant care station. In some examples, a patient located on the mattress can be captured in the video data.

At block 2404, the method 2400 can include generating a point cloud based on the video data. In some examples, the video data can include red-green-blue images, infrared images, depth data from depth cameras, or the like. The video data can be used to generate a point cloud in two dimensional or three dimensional space. For example, a patient in an enclosure of an infant care station can be identified and a point cloud can be generated for the patient. In some examples, the point cloud can enable detecting or determining a distance between areas of a patient, features of a patient, face identification of the patient, or the like.

At block 2406, the method 2400 can include training, using the point cloud as input, a first set of artificial intelligence instructions to detect one or more neonatal patient characteristics. In some examples, the first set of artificial instructions is trained using the point cloud representing one or more physical movements of the patient, one or more motor actions of the patient, an image series, an audio time series, a physiologic measurement time series, or a combination thereof. In some examples, training a set of artificial intelligence instructions can include computing a mesh point cloud for the patient based on the video data and training the first set of artificial intelligence instructions using the mesh point cloud.

In some examples, training a set of artificial intelligence instructions can include computing a segment mapping for the patient based on the video data, a point cloud, or a combination thereof. Training the first set of artificial intelligence instructions can be performed using the segment mapping.

At block 2408, the method 2400 can include generating an output representing the one or more patient characteristics based on the first set of artificial intelligence instructions. In some examples, the one or more patient characteristics comprises a sleep wellness score for the patient. In some examples, the one or more patient characteristics comprises a pose or a sleep position for the patient. In some examples, the one or more patient characteristics comprises a stress assessment, pain assessment, a stress assessment, or a seizure assessment for the patient, the pain assessment, physical measurements, and the seizure assessment based on physiologic measurements including heart rate, heart rate variability, respiration rate, respiration rate variability, physical patient movements, audio, or video data. In some examples, the patient characteristics can include a patient body length, a patient head circumference, a patient body joint segment length, a body volume, a body surface area, or a body density.

The process flow diagram of method 2400 of FIG. 24 is not intended to indicate that all of the operations of blocks 2402-2408 of the method 2400 are to be included in every example. Additionally, the process flow diagram of method 2400 of FIG. 24 describes a possible order of executing operations. However, it is to be understood that the operations of the method 2400 can be implemented in various orders or sequences. In addition, in some examples, the method 2400 can also include fewer or additional operations. For example, the method 2400 can include combining the first set of artificial intelligence instructions with one or more supplemental sets of artificial intelligence instructions trained to classify input based on the image series, the audio time series, the physiologic measurement time series, or the combination thereof. In some examples, the physiologic measurement time series includes one or more electrocardiogram (ECG) data values.

In some examples, the method 2400 can include providing a positive stimulus to the patient in response to detecting a negative stimulus, the positive stimulus comprising an audio clip, a visual image to be displayed, or a combination thereof. In some examples, the negative stimulus can be sounds emitted by the infant care station, images or lights displayed by the infant care station, medications or medical testing performed on the patient, among others. In some examples, the positive stimulus can be provided in response to an output representing one or more patient characteristics such as stress assessment, pain assessment provided by block 2408 or respiratory rate, heart rate, patient movement provided by block 2508 or a combination thereof. The positive stimulus can include changing the brightness of lights in an infant care station by either increasing or decreasing the brightness of the lights. The positive stimulus can also include auditory stimuli such as playing any suitable sounds or audio clips determined to soothe the patient. The positive stimulus can also include vestibular, somatosensory, tactile stimuli including, but not limited to, rocking, and other rhythmic movements. The positive stimuli can also include a combination of the above. In some examples, the infant care station can monitor the heart rate of a patient using a pulse plethysmograph signal obtained using techniques herein as a sound is provided to a patient. The infant care station can identify and store any sounds that lower a heart rate, respiration rate, or the like for a patient. In some examples, the response to the intended positive stimuli can be studied using methods 2400 and 2500 to ascertain if the stimuli had the intended effect or if a different positive stimulus needs to be provided.

In some examples, the method 2400 can include generating a growth chart based on the one or more patient characteristics, wherein the one or more patient characteristics comprise a head circumference, a body length, or a combination thereof.

Figure 25:
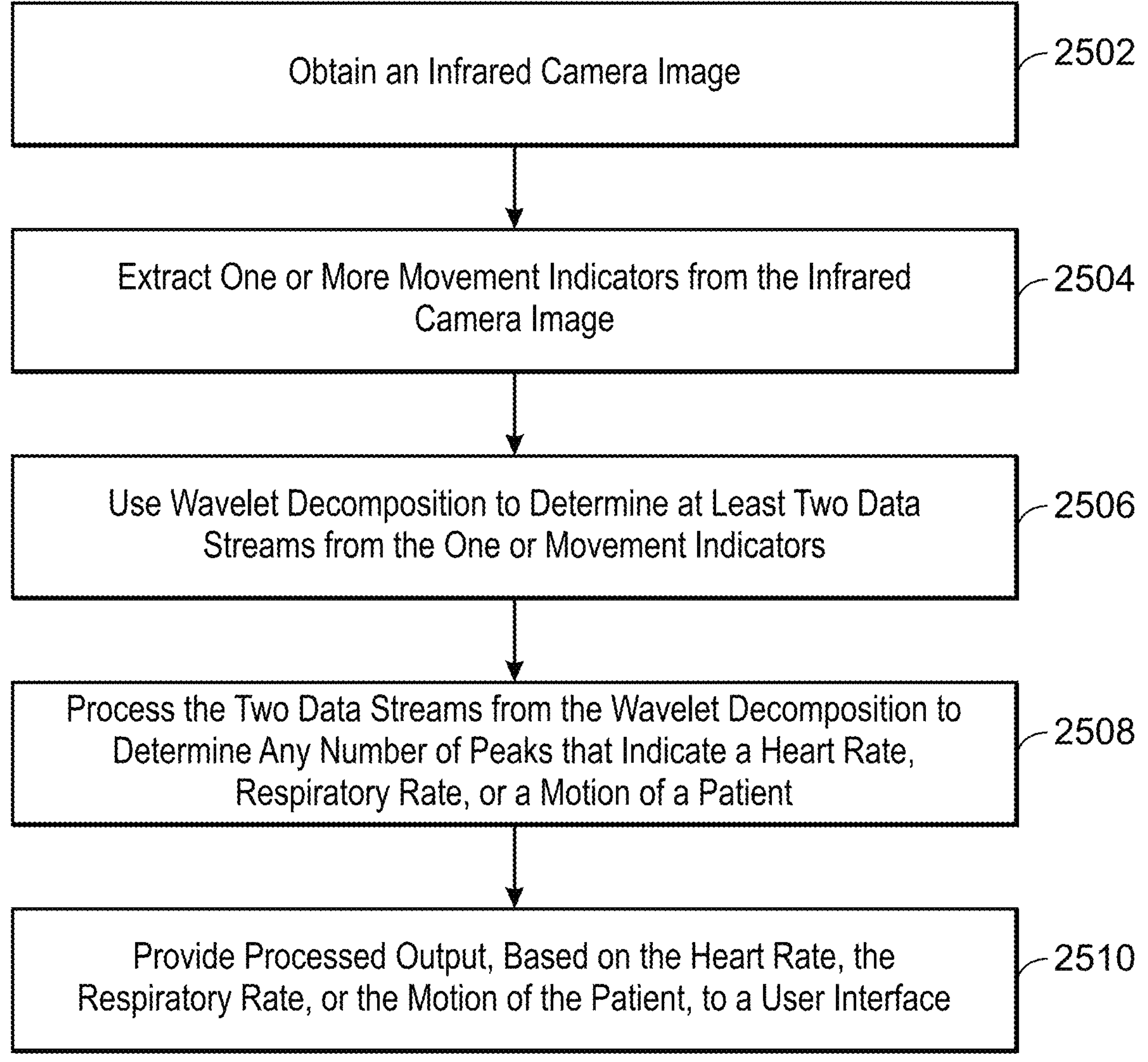
FIG. 25 depicts a process flow diagram of an example method for using wavelet decomposition to detect a heart rate, respiratory rate, and motion artifacts from a signal.

FIG. 25 depicts a process flow diagram of an example method for using wavelet decomposition to detect a heart rate, respiratory rate, and motion artifacts from a signal. In some examples, the method 2500 can be implemented with any suitable device, such as the infant care station 200 of FIG. 2, among others.

At block 2502, the method 2500 can include obtaining an infrared camera image. In some examples, the infrared camera image is obtained from any suitable camera mounted in an infant care station or proximate to an infant care station. The camera can be in a fixed position or the camera may be movable to obtain infrared camera images over time of objects residing on a mattress of an infant care station.

At block 2504, the method 2500 can include extracting one or more movement indicators from the infrared camera image. In some examples, the movement indicators are captured as red pixels or areas in infrared images, wherein the red pixels or areas indicate movement within an image.

At block 2506, the method 2500 can include using wavelet decomposition to determine at least two data streams from the one or movement indicators. The data streams can indicate movement of a patient due to a heart rate, respiratory rate, or motion artifacts related to other movements of the patient. For example, motion artifacts can indicate a patient has moved an arm, a leg, changed the position of the patient's torso, or the like. In some examples, the wavelet decomposition includes transforming a plurality of pixel values to a frequency domain to obtain a spectrum of frequencies for each of the two or more data streams. The wavelet decomposition can also be used to reconstruct an input signal based on the data streams. In some examples, wavelet decomposition can include generating a data structure based on a sum of components of the two or more data streams as described above in relation to FIG. 9.

At block 2508, the method 2500 can include processing the two data streams from the wavelet decomposition to determine any number of peaks that indicate a heart rate, respiratory rate, or a motion of a patient. In some examples, the peaks indicate an intensity value representing a movement of a patient.

At block 2510, the method 2500 can include providing the processed output to a user interface. The processed output can include a pulse plethysmograph or time series, a respiration rate plethysmograph or time series, a time series of motion artifacts, a noise signal, and the like. In some examples, the method 2500 can include providing the processed output to a display device coupled to an infant care station, transmitting the processed output to a remote device, generating alerts based on the processed output, or the like.

The process flow diagram of method 2500 of FIG. 25 is not intended to indicate that all of the operations of blocks 2502-2510 of the method 2500 are to be included in every example. Additionally, the process flow diagram of method 2500 of FIG. 25 describes a possible order of executing operations. However, it is to be understood that the operations of the method 2500 can be implemented in various orders or sequences. In addition, in some examples, the method 2500 can also include fewer or additional operations. For example, the method 2500 can also include providing a heart rate variability based on the wavelet decomposition. In some examples, the method 2500 can also include processing at least three data streams from a wavelet decomposition to determine any number of peaks that indicate the heart rate, the respiratory rate, or the motion of the patient.

In some examples, the method 2500 can include video conferencing of neonate with parents for maintaining parental bonding, visual, and voice communication for comfort and emotional support.

Figure 26:
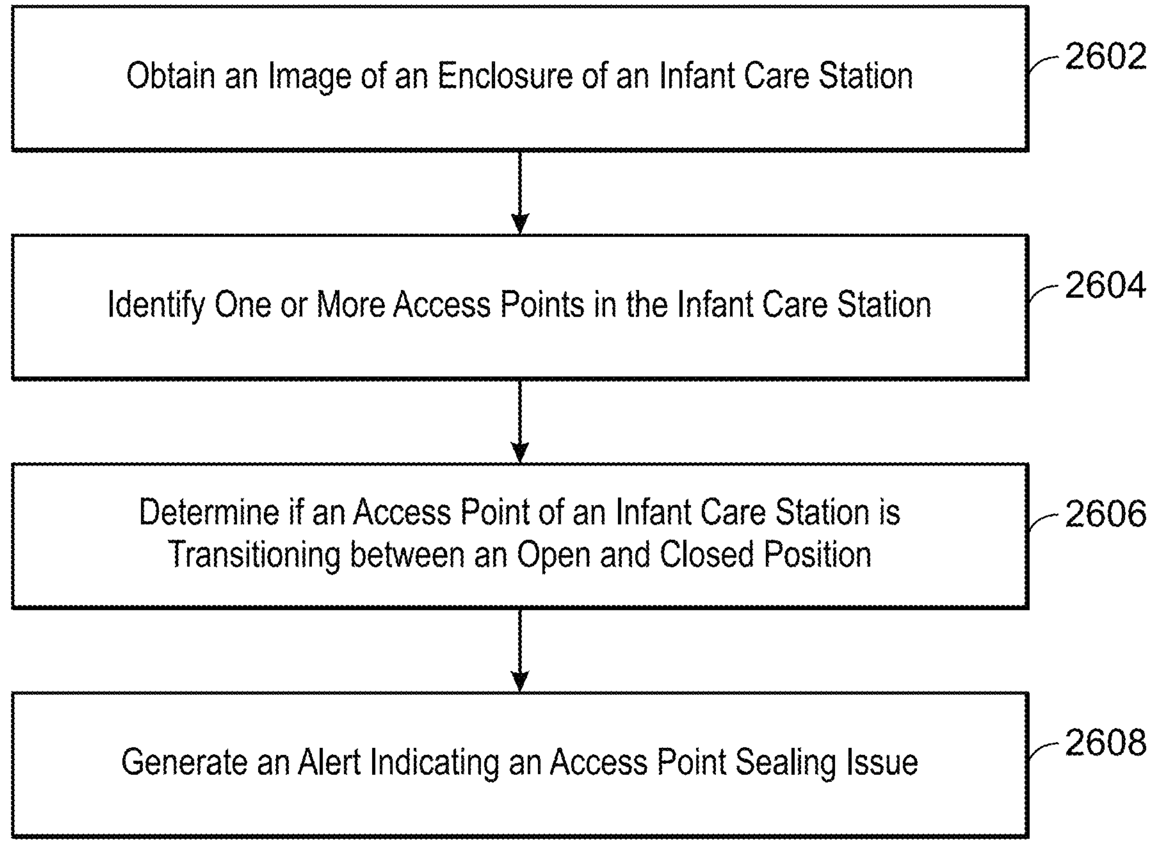
FIG. 26 depicts a process flow diagram of an example method for detecting an open access point in an infant care station.

FIG. 26 depicts a process flow diagram of an example method for detecting an open access point in an infant care station. The method 2600 can be implemented with any suitable infant care station, such as the incubator system 100 of FIG. 1 or the infant care station 200 of FIG. 2, among others.

At block 2602, the method 2600 can include obtaining an image of an enclosure of an infant care station. In some examples, the image can include any portion of an infant care station that includes access points such as porthole doors, sealable openings, canopy opening, or the like. In some examples, the depth measurements of a camera mounted on top of the canopy can be used to determine canopy height level. In some examples, the method 2600 can include obtaining multiple images of the enclosure of the infant care station. The images can be obtained or received from one or more cameras mounted in the infant care station or proximate to the infant care station. In some examples, a camera may be in a fixed position or the camera may be movable to monitor multiple portions of an infant care station.

At block 2604, the method 2600 can include identifying one or more access points in the infant care station. For example, the method 2600 can include applying any suitable artificial intelligence technique to detect, classify, or identify one or more access points in an enclosure of an infant care station. In some examples, a neural network can be trained using a set of training data to classify features in images of an infant care station enclosure that are associated with access points.

At block 2606, the method 2600 can include determining if an access point of an infant care station is transitioning between an open and closed position. For example, the method 2600 can include monitoring a series of images of the enclosure over a period of time and determining if an access point has transitioned from a sealed or closed state or position to an open or unsealed state or position.

At block 2608, the method 2600 can include generating an alert indicating an access point sealing issue. The access point sealing issue, as referred to herein, can indicate an unexpected open or unsealed access point or an unexpected, sealed access point. For example, the access point sealing issue can indicate an open porthole door or a closed canopy, among others. In some examples, the alert can indicate an amount of time any number of access points have been open, whether the amount of time an access point has been open exceeds a predetermined threshold.

In some examples, the alert can indicate a particular access point that is experiencing an access point sealing issue corresponding to one or two unsealed porthole doors, an unsealed canopy, or any other access points. The method 2600 can include generating an alert that indicates the specific access points that are likely unsealed. For example, the method 2600 can include determining if one porthole door is unsealed with a sealed canopy, two porthole doors are unsealed with a sealed canopy, two porthole doors are sealed with an unsealed canopy, or any combination thereof.

The process flow diagram of method 2600 of FIG. 26 is not intended to indicate that all of the operations of blocks 2602-2608 of the method 2600 are to be included in every example. Additionally, the process flow diagram of method 2600 of FIG. 26 describes a possible order of executing operations. However, it is to be understood that the operations of the method 2600 can be implemented in various orders or sequences. In addition, in some examples, the method 2600 can also include fewer or additional operations. For example, the method 2600 can also include detecting, obtaining, or otherwise receiving one or more red-green-blue images, infrared images, or a combination thereof. The method 2600 can include processing or analyzing the received images to detect any anomalies in an air curtain of a microenvironment of an infant care station. The air curtain, as referred to herein, can include any amount of air forced at a higher rate of speed along an edge of a microenvironment of an infant care station so that the microenvironment maintains a different humidity, temperature, or the like. In some examples, when a fan of an infant care station is malfunctioning or there is some other obstruction for the air flow, the air curtain may not maintain a separate temperature or humidity level. The microenvironment may then be altered based on the temperature or humidity level of the ambient air outside of the microenvironment of the infant care station.

The method 2600 can include generating an alert to a remote device, clinician, or the like in response to detecting an anomaly in the air curtain of a microenvironment of an infant care station. The alert can provide preventative maintenance requests, information about the anomaly in the air curtain, and the like.

Figure 27:
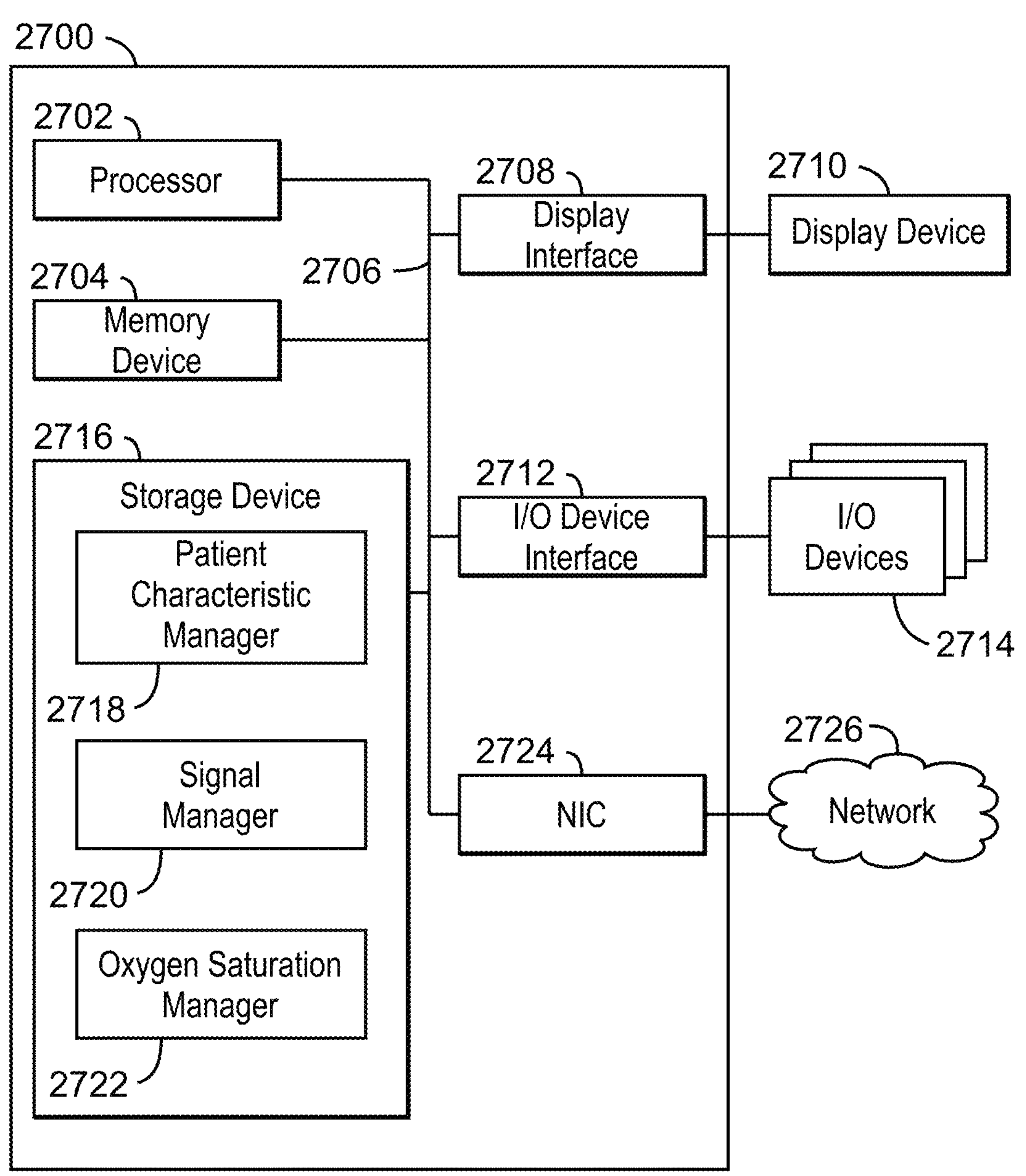
FIG. 27 is a block diagram of an example of a computing device that can detect a patient characteristic from an infant care station.

FIG. 27 is a block diagram of an example of a computing device that can detect a patient characteristic from an infant care station. The computing device 2700 may be, for example, an infant care station device, such as an incubator, a warmer, or a device that provides features of both an incubator and a warmer, a laptop computer, a desktop computer, a tablet computer, or a mobile phone, among others. The computing device 2700 may include a processor 2702 that is adapted to execute stored instructions, as well as a memory device 2704 that stores instructions that are executable by the processor 2702. The processor 2702 can be a single core processor, a multi-core processor, a computing cluster, or any number of other configurations. The memory device 2704 can include random access memory, read only memory, flash memory, or any other suitable memory systems. The instructions that are executed by the processor 2702 may be used to implement a method that can detect a patient characteristic from an infant care station, as described in greater detail above in relation to FIGS. 1-26.

The processor 2702 may also be linked through the system interconnect 2706 (e.g., PCI, PCI-Express, NuBus, etc.) to a display interface 2708 adapted to connect the computing device 2700 to a display device 2710. The display device 2710 may include a display screen that is a built-in component of the computing device 2700. The display device 2710 may also include a computer monitor, television, or projector, among others, that is externally connected to the computing device 2700. The display device 2710 can include light emitting diodes (LEDs), and micro-LEDs, among others.

The processor 2702 may be connected through a system interconnect 2706 to an input/output (I/O) device interface 2712 adapted to connect the computing device 2700 to one or more I/O devices 2714. The I/O devices 2714 may include, for example, a keyboard and a pointing device, wherein the pointing device may include a touchpad or a touchscreen, among others. The I/O devices 2714 may be built-in components of the computing device 2700, or may be devices that are externally connected to the computing device 2700.

In some embodiments, the processor 2702 may also be linked through the system interconnect 2706 to a storage device 2716 that can include a hard drive, an optical drive, a USB flash drive, an array of drives, or any combinations thereof. In some embodiments, the storage device 2716 can include any suitable applications. In some embodiments, the storage device 2716 can include a patient characteristic manager 2718 to obtain the video data from the camera for a patient, generate a point cloud based on the video data, train, using the point cloud as input, a first set of artificial intelligence instructions to detect one or more neonatal patient characteristics, and generate an output representing the one or more patient characteristics based on the first set of artificial intelligence instructions. The storage device 2716 can also include a signal manager 2720 to obtain an infrared camera image, extract one or more movement indicators from the infrared camera image, use wavelet decomposition to determine at least two data streams from the one or movement indicators, process the two data streams from the wavelet decomposition to determine any number of peaks that indicate a heart rate, respiratory rate, or a motion of a patient, provide the processed output to a user interface. The storage device 2716 can also include an oxygen saturation manager 2722 to create a first plethysmograph waveform from a red image, create a second plethysmograph waveform from an infrared (IR) image, process the first plethysmograph waveform using wavelet decomposition to obtain a first HR plethysmograph waveform, process the second plethysmograph waveform using wavelet decomposition to obtain a second HR plethysmograph waveform, calculate an absorption value using the first HR plethysmograph waveform and the second HR plethysmograph waveform, and determine the oxygen saturation value for the patient using a reference calibration curve and the absorption value.

In some examples, the display device 2710 can provide a user interface that indicates data from an alert based on output from the patient characteristic manager 2718, signal manager 2720, or the oxygen saturation manager 2722.

In some examples, a network interface controller (also referred to herein as a NIC) 2724 may be adapted to connect the computing device 2700 through the system interconnect 2706 to a network 2726. The network 2726 may be a cellular network, a radio network, a wide area network (WAN), a local area network (LAN), or the Internet, among others. The network 2726 can enable data, such as alerts, among other data, to be transmitted from the computing device 2700 to remote computing devices, remote display devices, remote user interfaces, and the like.

It is to be understood that the block diagram of FIG. 27 is not intended to indicate that the computing device 2700 is to include all of the components shown in FIG. 27. Rather, the computing device 2700 can include fewer or additional components not illustrated in FIG. 27 (e.g., additional memory components, embedded controllers, additional modules, additional network interfaces, etc.). Furthermore, any of the functionalities of the patient characteristic manager 2718, signal manager 2720, or the oxygen saturation manager 2722 may be partially, or entirely, implemented in hardware and/or in the processor 2702. For example, the functionality may be implemented with an application specific integrated circuit, logic implemented in an embedded controller, or in logic implemented in the processor 2702, among others. In some embodiments, the functionalities of the patient characteristic manager 2718, signal manager 2720, or the oxygen saturation manager 2722 can be implemented with logic, wherein the logic, as referred to herein, can include any suitable hardware (e.g., a processor, among others), software (e.g., an application, among others), firmware, or any suitable combination of hardware, software, and firmware.

Figure 28:
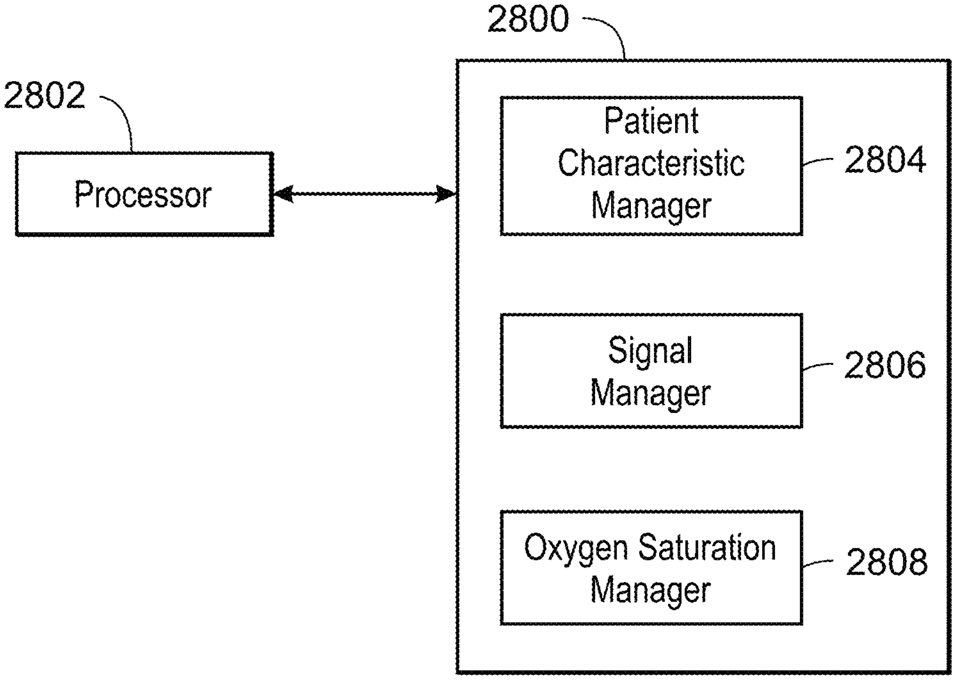
FIG. 28 depicts a non-transitory machine-executable medium with instructions that can detect a patient characteristic from an infant care station.

FIG. 28 depicts a non-transitory machine-executable medium with instructions that can detect a patient characteristic from an infant care station. The non-transitory, machine-readable medium 2800 can cause a processor 2802 to implement the functionalities of methods 2300, 2400, 2500, or 2600. For example, a processor of an infant care station, a host device, a computing device (such as processor (s) 2702 of computing device 2700 of FIG. 27), or any other suitable device, can access the non-transitory, machine-readable media 2800.

In some examples, the non-transitory, machine-readable medium 2800 can include instructions that cause the processor 2802 to perform the instructions of the patient characteristic manager 2804. For example, the instructions can cause the processor 2802 to obtain the video data from the camera for a patient, generate a point cloud based on the video data, train, using the point cloud as input, a first set of artificial intelligence instructions to detect one or more neonatal patient characteristics, and generate an output representing the one or more patient characteristics based on the first set of artificial intelligence instructions. The non-transitory, machine-readable medium 2800 can also include instructions that cause the processor 2802 to perform the instructions of the signal manager 2806. For example, the instructions can cause the processor 2802 to obtain an infrared camera image, extract one or more movement indicators from the infrared camera image, use wavelet decomposition to determine at least two data streams from the one or movement indicators, process the two data streams from the wavelet decomposition to determine any number of peaks that indicate a heart rate, respiratory rate, or a motion of a patient, provide the processed output to a user interface. The non-transitory, machine-readable medium 2800 can also include instructions that cause the processor 2802 to perform the instructions of the oxygen saturation manager 2808. For example, the instructions can cause the processor 2802 to create a first plethysmograph waveform from a red image, create a second plethysmograph waveform from an infrared (IR) image, process the first plethysmograph waveform using wavelet decomposition to obtain a first HR plethysmograph waveform, process the second plethysmograph waveform using wavelet decomposition to obtain a second HR plethysmograph waveform, calculate an absorption value using the first HR plethysmograph waveform and the second HR plethysmograph waveform, and determine the oxygen saturation value for the patient using a reference calibration curve and the absorption value.

In some examples, the non-transitory, machine-readable medium 2800 can include instructions to implement any combination of the techniques of the methods 2300, 2400, 2500, or 2600 described above.

Example Deep Learning and Other Machine Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, identification of lesions in image data, computer-aided diagnosis (CAD), etc.

High quality medical image data can be acquired using one or more imaging modalities, such as infrared cameras, red-green-blue camera images, x-ray, computed tomography (CT), molecular imaging and computed tomography (MICT), magnetic resonance imaging (MRI), etc. Medical image quality is often not affected by the machines producing the image but the patient.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for analysis.

Example Learning Network Systems

Figure 29:
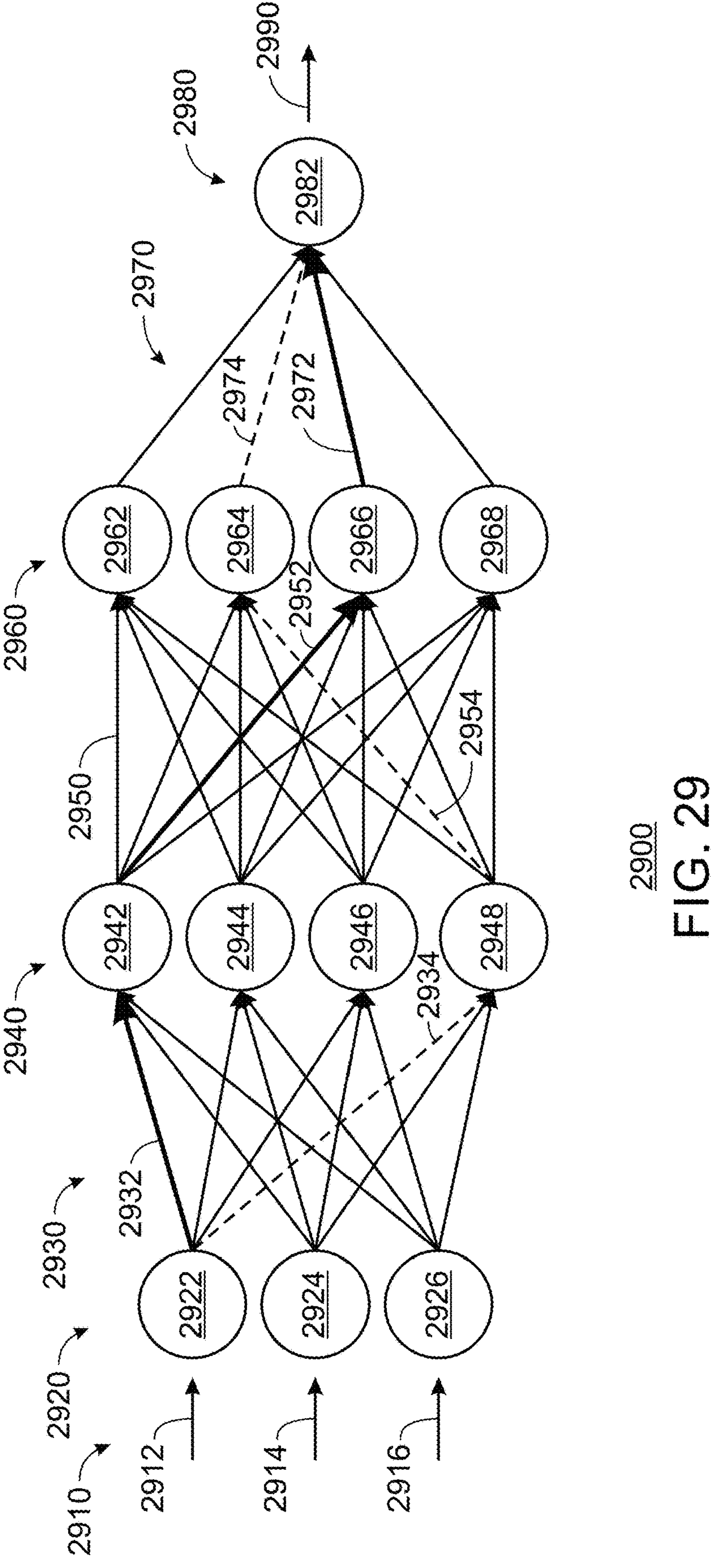
FIG. 29 is a representation of an example learning neural network.

FIG. 29 is a representation of an example learning neural network 2900. The example neural network 2900 includes layers 2920, 2940, 2960, and 2980. The layers 2920 and 2940 are connected with neural connections 2930. The layers 2940 and 2960 are connected with neural connections 2950. The layers 2960 and 2980 are connected with neural connections 2970. Data flows forward via inputs 2912, 2914, 2916 from the input layer 2920 to the output layer 2980 and to an output 2990.

The layer 2920 is an input layer that, in the example of FIG. 29, includes a plurality of nodes 2922, 2924, 2926. The layers 2940 and 2960 are hidden layers and include, the example of FIG. 29, nodes 2942, 2944, 2946, 2948, 2962, 2964, 2966, 2968. The neural network 2900 may include more or less hidden layers 2940 and 2960 than shown. The layer 2980 is an output layer and includes, in the example of FIG. 29, a node 2982 with an output 2990. Each input 2912-2916 corresponds to a node 2922-2926 of the input layer 2920, and each node 2922-2926 of the input layer 2920 has a connection 2930 to each node 2942-2948 of the hidden layer 2940. Each node 2942-2948 of the hidden layer 2940 has a connection 2950 to each node 2962-2968 of the hidden layer 2960. Each node 2962-2968 of the hidden layer 2960 has a connection 2970 to the output layer 2980. The output layer 2980 has an output 2990 to provide an output from the example neural network 2900.

Of connections 2930, 2950, and 2970 certain example connections 2932, 2952, 2972 may be given added weight while other example connections 2934, 2954, 2974 may be given less weight in the neural network 2900. Input nodes 2922-2926 are activated through receipt of input data via inputs 2912-2916, for example. Nodes 2942-2948 and 2962-2968 of hidden layers 2940 and 2960 are activated through the forward flow of data through the network 2900 via the connections 2930 and 2950, respectively. Node 2982 of the output layer 2980 is activated after data processed in hidden layers 2940 and 2960 is sent via connections 2970. When the output node 2982 of the output layer 2980 is activated, the node 2982 outputs an appropriate value based on processing accomplished in hidden layers 2940 and 2960 of the neural network 2900.

Figure 30:
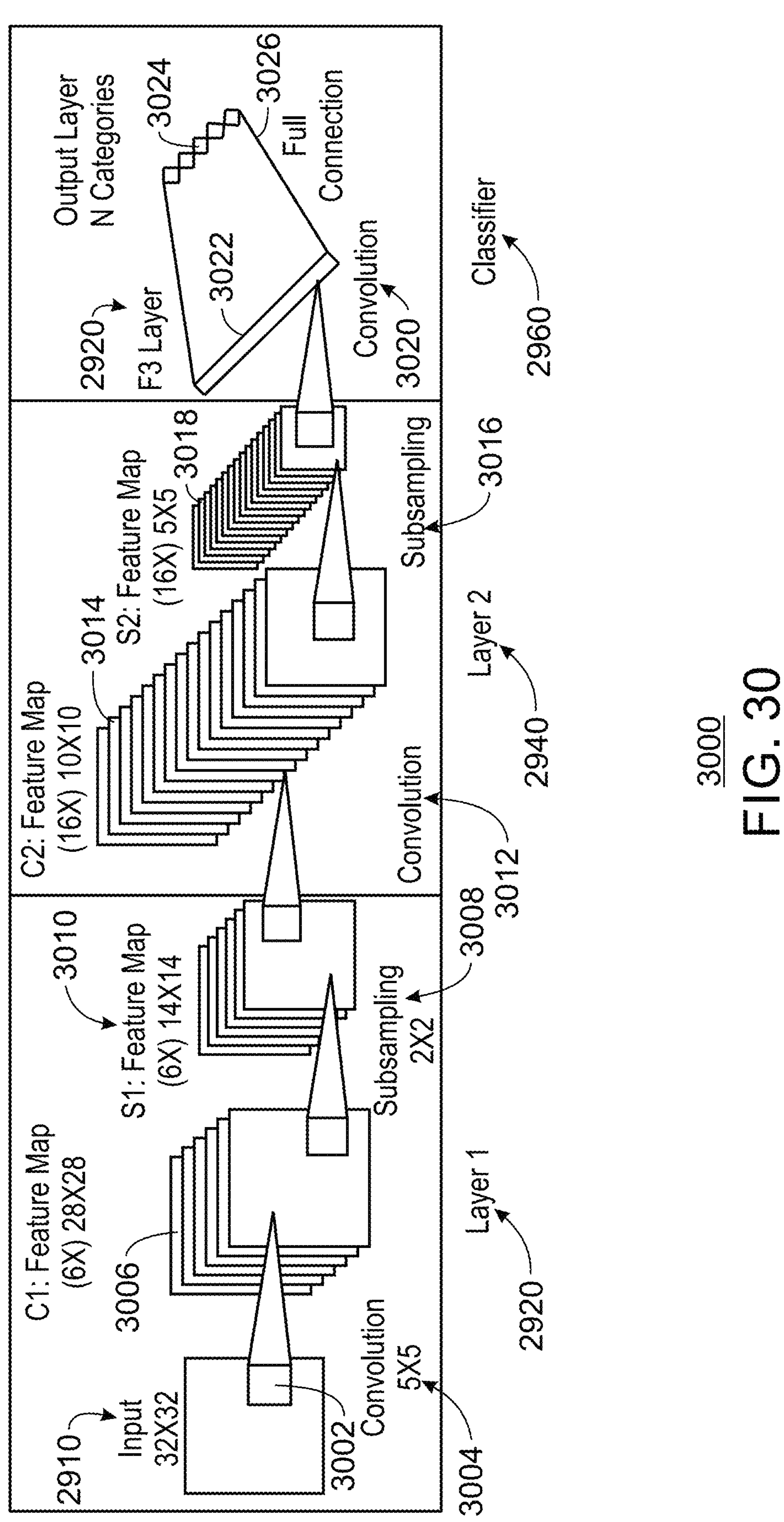
FIG. 30 illustrates a particular implementation of the example neural network as a convolutional neural network.

FIG. 30 illustrates a particular implementation of the example neural network 2900 as a convolutional neural network 3000. As shown in the example of FIG. 30, an input 2910 is provided to the first layer 2920 which processes and propagates the input 2910 to the second layer 2940. The input 2910 is further processed in the second layer 2940 and propagated to the third layer 2960. The third layer 2960 categorizes data to be provided to the output layer e80. More specifically, as shown in the example of FIG. 30, a convolution 3004 (e.g., a 5×5 convolution, etc.) is applied to a portion or window (also referred to as a "receptive field") 3002 of the input 2910 (e.g., a 32×32 data input, etc.) in the first layer 2920 to provide a feature map 3006 (e.g., a (6×) 28×28 feature map, etc.). The convolution 3004 maps the elements from the input 2910 to the feature map 3006. The first layer 2920 also provides subsampling (e.g., 2×2 subsampling, etc.) to generate a reduced feature map 3010 (e.g., a (6×) 14×14 feature map, etc.). The feature map 3010 undergoes a convolution 3012 and is propagated from the first layer 2920 to the second layer 2940, where the feature map 3010 becomes an expanded feature map 3014 (e.g., a (16×) 10×10 feature map, etc.). After subsampling 3016 in the second layer 2940, the feature map 3014 becomes a reduced feature map 3018 (e.g., a (16×) 4×5 feature map, etc.). The feature map 3018 undergoes a convolution 3020 and is propagated to the third layer 2960, where the feature map 3018 becomes a classification layer 3022 forming an output layer of N categories 3024 with connection 3026 to the convoluted layer 3022, for example.

Figure 31:
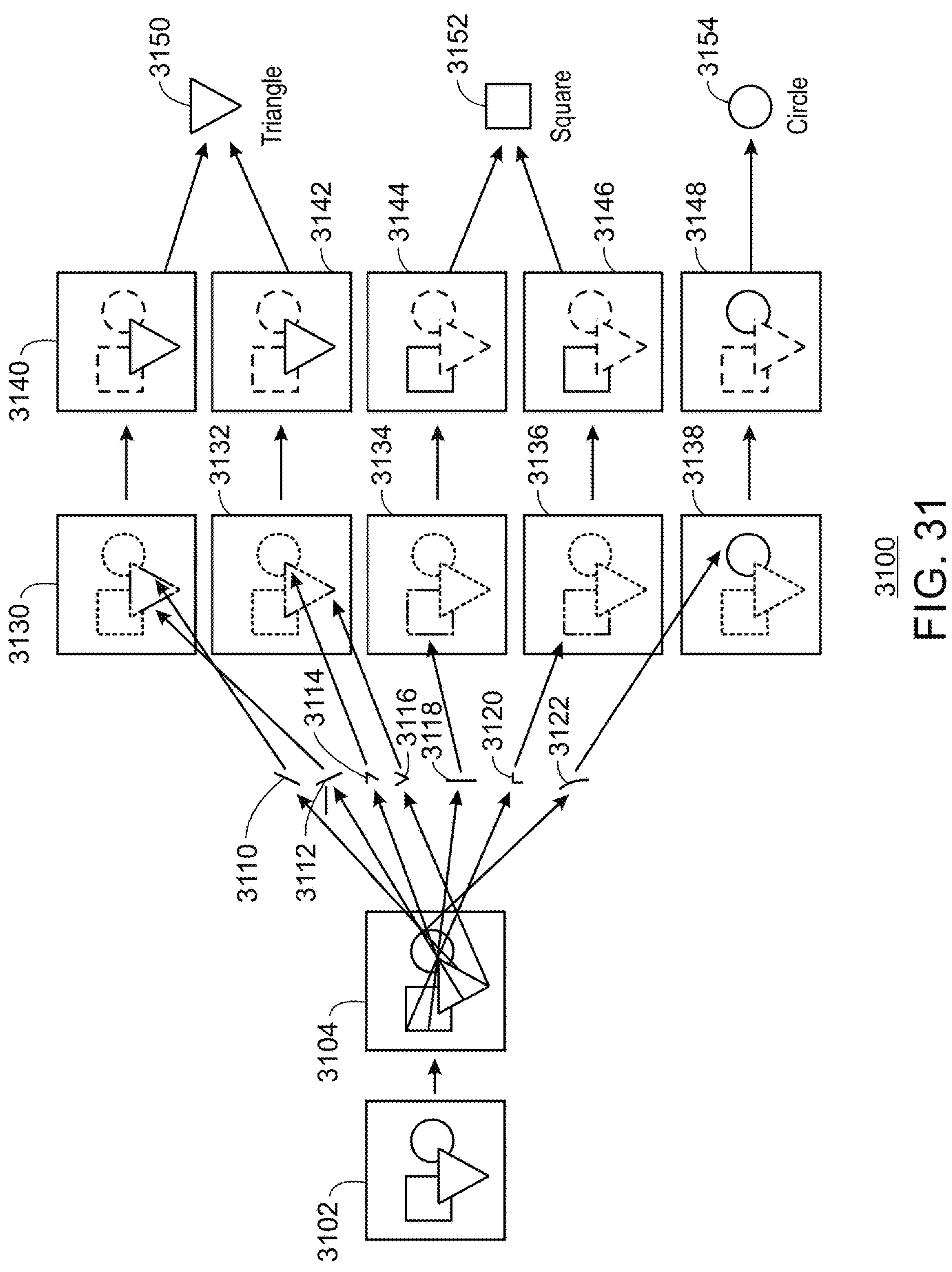
FIG. 31 is a representation of an example implementation of an image analysis convolutional neural network.

FIG. 31 is a representation of an example implementation of an image analysis convolutional neural network 3100. The convolutional neural network 3100 receives an input image 3102 and abstracts the image in a convolution layer 3104 to identify learned features 3110-3122. In a second convolution layer 3130, the image is transformed into a plurality of images 3130-3138 in which the learned features 3110-3122 are each accentuated in a respective sub-image 3130-3138. The images 3130-3138 are further processed to focus on the features of interest 3110-3122 in images 3140-3148. The resulting images 3140-3148 are then processed through a pooling layer which reduces the size of the images 3140-3148 to isolate portions 3150-3154 of the images 3140-3148 including the features of interest 3110-3122. Outputs 3150-3154 of the convolutional neural network 3100 receive values from the last non-output layer and classify the image based on the data received from the last non-output layer. In certain examples, the convolutional neural network 3100 may contain many different variations of convolution layers, pooling layers, learned features, and outputs, etc.

Figures 32A, 32B:
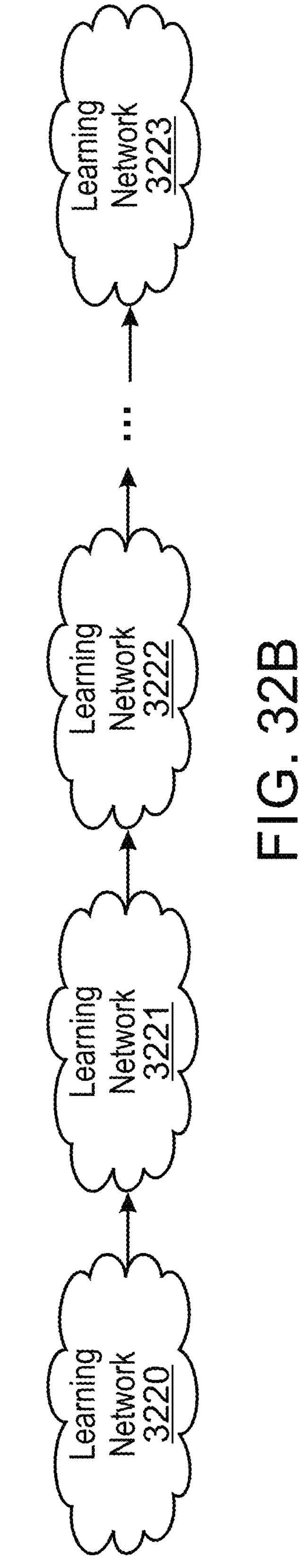
FIG. 32A illustrates an example configuration to apply a learning network to process and/or otherwise evaluate an image.
FIG. 32B illustrates a combination of a plurality of learning networks.

FIG. 32A illustrates an example configuration 3200 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 3200 of FIG. 32A, raw data 3210 (e.g., raw data 3210 such as sonogram raw data, etc., obtained from an imaging scanner such as an x-ray, computed tomography, ultrasound, magnetic resonance, etc., scanner) is fed into a learning network 3220. The learning network 3220 processes the data 3210 to correlate and/or otherwise combine the raw image data 3220 into a resulting image 3230 (e.g., a "good quality" image and/or other image providing sufficient quality for diagnosis, etc.). The learning network 3220 includes nodes and connections (e.g., pathways) to associate raw data 3210 with a finished image 3230. The learning network 3220 can be a training network that learns the connections and processes feedback to establish connections and identify patterns, for example. The learning network 3220 can be a deployed network that is generated from a training network and leverages the connections and patterns established in the training network to take the input raw data 3210 and generate the resulting image 3230, for example.

Once the learning 3220 is trained and produces good images 3230 from the raw image data 3210, the network 3220 can continue the "self-learning" process and refine its performance as it operates. For example, there is "redundancy" in the input data (raw data) 3210 and redundancy in the network 3220, and the redundancy can be exploited.

If weights assigned to nodes in the learning network 3220 are examined, there are likely many connections and nodes with very low weights. The low weights indicate that these connections and nodes contribute little to the overall performance of the learning network 3220. Thus, these connections and nodes are redundant. Such redundancy can be evaluated to reduce redundancy in the inputs (raw data) 3210. Reducing input 3210 redundancy can result in savings in scanner hardware, reduced demands on components, and also reduced exposure dose to the patient, for example.

In deployment, the configuration 3200 forms a package 3200 including an input definition 3210, a trained network 3220, and an output definition 3230. The package 3200 can be deployed and installed with respect to another system, such as an imaging system, analysis engine, etc.

As shown in the example of FIG. 32B, the learning network 3220 can be chained and/or otherwise combined with a plurality of learning networks 3221-3223 to form a larger learning network. The combination of networks 3220-3223 can be used to further refine responses to inputs and/or allocate networks 3220-3223 to various aspects of a system, for example.

In some examples, in operation, "weak" connections and nodes can initially be set to zero. The learning network 3220 then processes its nodes in a retaining process. In certain examples, the nodes and connections that were set to zero are not allowed to change during the retraining. Given the redundancy present in the network 3220, it is highly likely that equally good images will be generated. As illustrated in FIG. 32B, after retraining, the learning network 3220 becomes DLN 3221. The learning network 3221 is also examined to identify weak connections and nodes and set them to zero. This further retrained network is learning network 3222. The example learning network 3222 includes the "zeros" in learning network 3221 and the new set of nodes and connections. The learning network 3222 continues to repeat the processing until a good image quality is reached at a learning network 3223, which is referred to as a "minimum viable net (MVN)". The learning network 3223 is an MVN because if additional connections or nodes are attempted to be set to zero in learning network 3223, image quality can suffer.

Once the MVN has been obtained with the learning network 3223, "zero" regions (e.g., dark irregular regions in a graph) are mapped to the input 3210. Each dark zone is likely to map to one or a set of parameters in the input space. For example, one of the zero regions may be linked to the number of views and number of channels in the raw data. Since redundancy in the network 3223 corresponding to these parameters can be reduced, there is a highly likelihood that the input data can be reduced and generate equally good output. To reduce input data, new sets of raw data that correspond to the reduced parameters are obtained and run through the learning network 3221. The network 3220-3223 may or may not be simplified, but one or more of the learning networks 3220-3223 is processed until a "minimum viable input (MVI)" of raw data input 3210 is reached. At the MVI, a further reduction in the input raw data 3210 may result in reduced image 3230 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 3220-3223 to zero, the network 3220-3223 to build "collaterals" to compensate. In the process, insight into the topology of the learning network 3220-3223 is obtained. Note that network 3221 and network 3222, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 33:
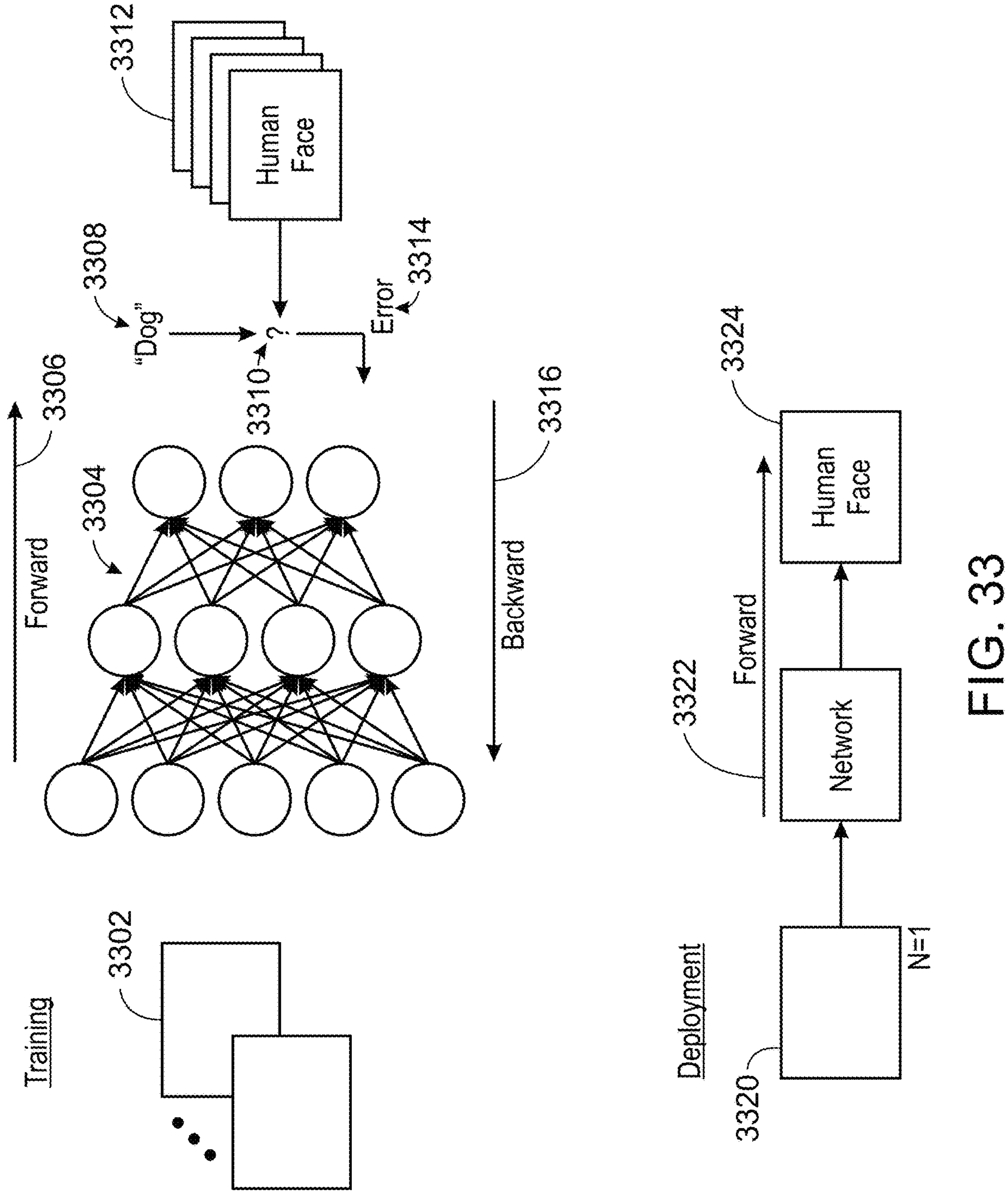
FIG. 33 illustrates example training and deployment phases of a learning network.

FIG. 33 illustrates example training and deployment phases of a learning network, such as a deep learning or other machine learning network. As shown in the example of FIG. 33, in the training phase, a set of inputs 3302 is provided to a network 3304 for processing. In this example, the set of inputs 3302 can include facial features of an image to be identified. The network 3304 processes the input 3302 in a forward direction 3306 to associate data elements and identify patterns. The network 3304 determines that the input 3302 represents a dog 3308. In training, the network result 3308 is compared 3310 to a known outcome 3312. In this example, the known outcome 3312 is a human face (e.g., the input data set 3302 represents a human face, not a dog face). Since the determination 3308 of the network 3304 does not match 3310 the known outcome 3312, an error 3314 is generated. The error 3314 triggers an analysis of the known outcome 3312 and associated data 3302 in reverse along a backward pass 3316 through the network 3304.

Thus, the training network 3304 learns from forward 3306 and backward 3316 passes with data 3302, 3312 through the network 3304.

Once the comparison of network output 3308 to known output 3312 matches 3310 according to a certain criterion or threshold (e.g., matches n times, matches greater than x percent, etc.), the training network 3304 can be used to generate a network for deployment with an external system. Once deployed, a single input 3320 is provided to a deployed learning network 3322 to generate an output 3324. In this case, based on the training network 3304, the deployed network 3322 determines that the input 3320 is an image of a human face 3324.

Figure 34:
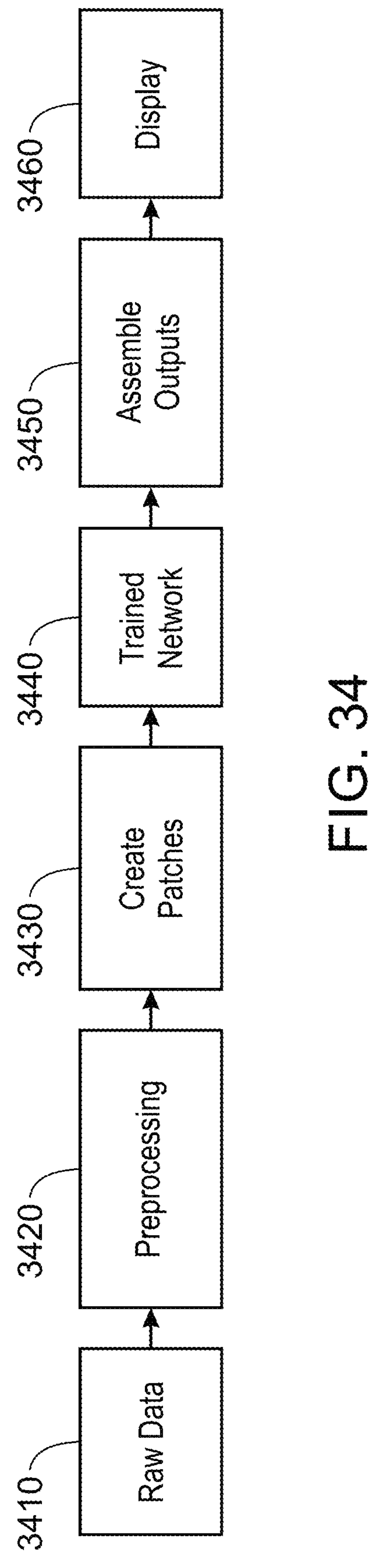
FIG. 34 illustrates an example product leveraging a trained network package to provide a deep learning product offering.

FIG. 34 illustrates an example product leveraging a trained network package to provide a deep and/or other machine learning product offering. As shown in the example of FIG. 34, an input 3410 (e.g., raw data) is provided for preprocessing 3420. For example, the raw input data 3410 is preprocessed 3420 to check format, completeness, etc. Once the data 3410 has been preprocessed 3420, patches are created 3430 of the data. For example, patches or portions or "chunks" of data are created 3430 with a certain size and format for processing. The patches are then fed into a trained network 3440 for processing. Based on learned patterns, nodes, and connections, the trained network 3440 determines outputs based on the input patches. The outputs are assembled 3450 (e.g., combined and/or otherwise grouped together to generate a usable output, etc.). The output is then displayed 3460 and/or otherwise output to a user (e.g., a human user, a clinical system, an imaging modality, a data storage (e.g., cloud storage, local storage, edge device, etc.), etc.).

Figure 35A:
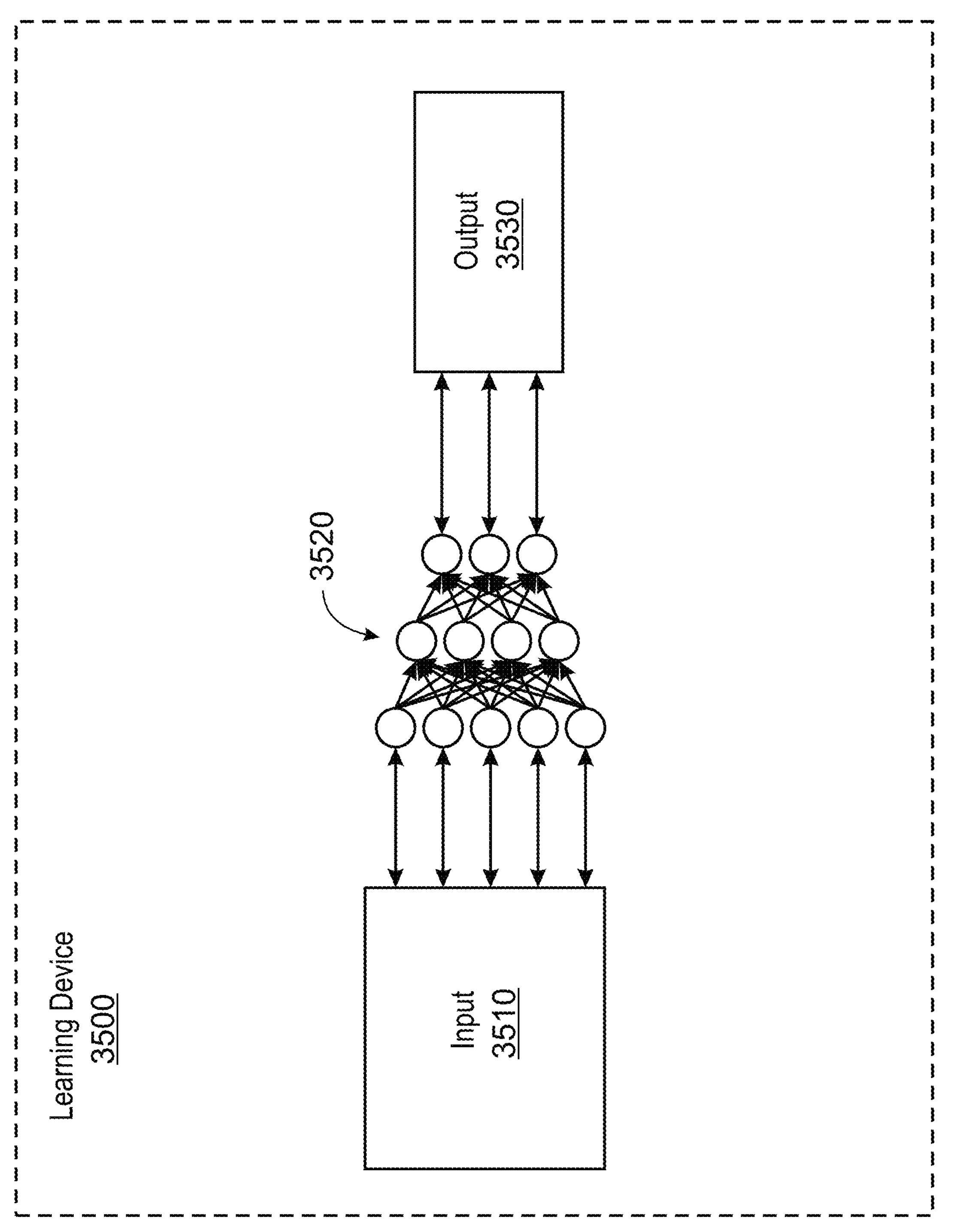
FIGS. 35A-35C illustrate various deep learning device configurations.
Figure 35B:
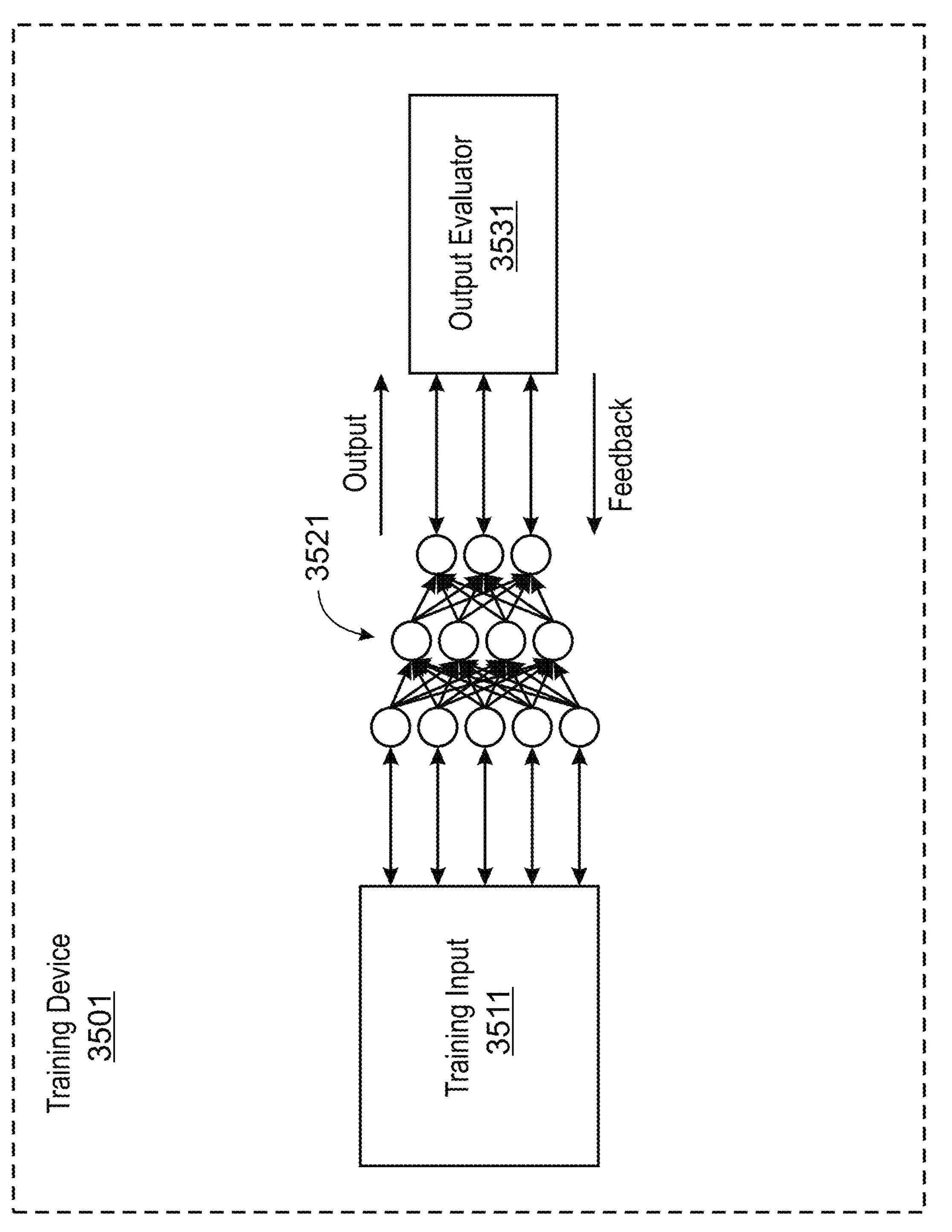
Figure 35C:
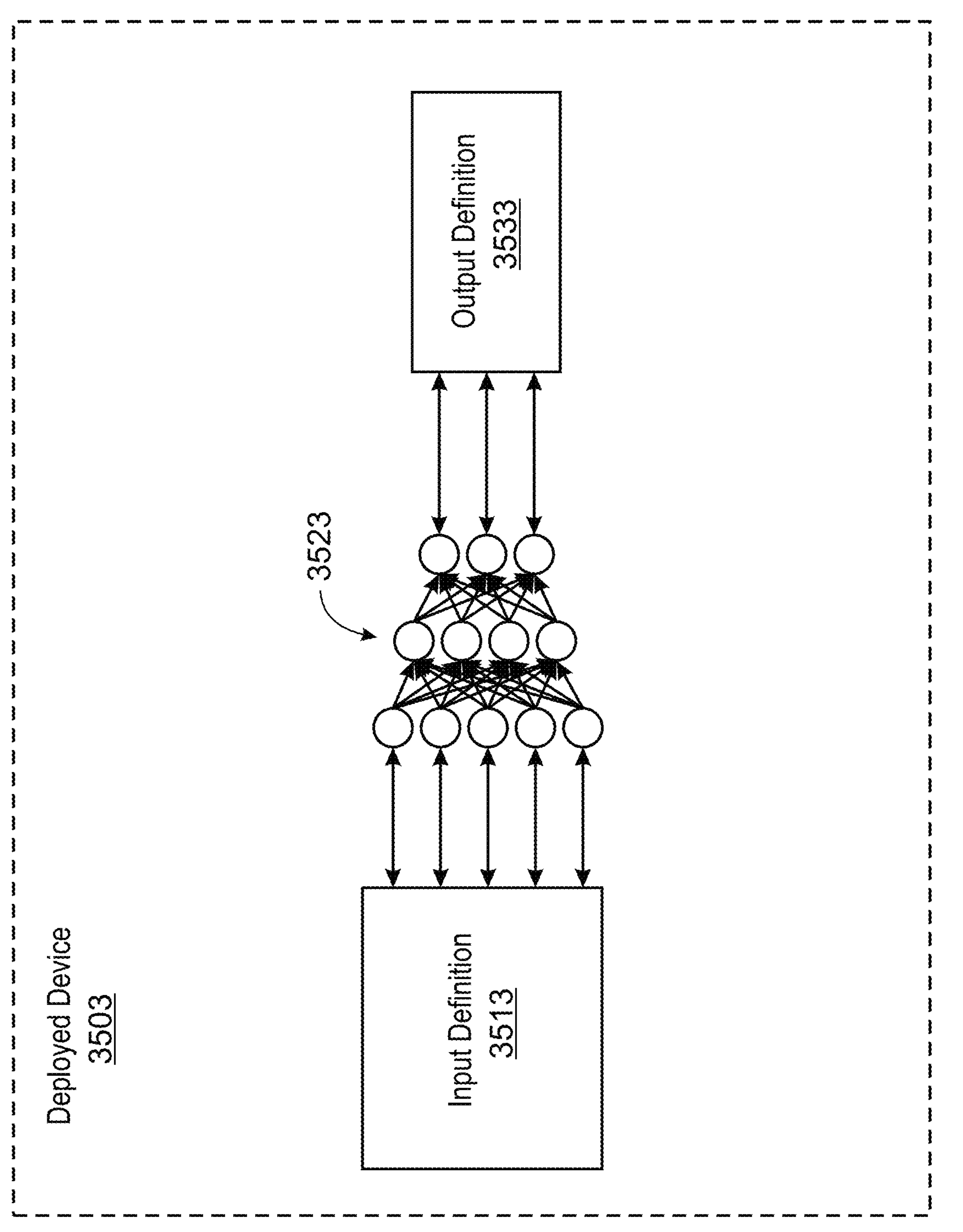

As discussed above, learning networks can be packaged as devices for training, deployment, and application to a variety of systems. FIGS. 35A-35C illustrate various learning device configurations. For example, FIG. 35A shows a general learning device 3500. The example device 3500 includes an input definition 3510, a learning network model 3520, and output definitions 3530. The input definition 3510 can include one or more inputs translating into one or more outputs 3530 via the network 3520.

FIG. 35B shows an example training device 3501. That is, the training device 3501 is an example of the device 3500 configured as a training learning network device. In the example of FIG. 35B, a plurality of training inputs 3511 are provided to a network 3521 to develop connections in the network 3521 and provide an output to be evaluated by an output evaluator 3531. Feedback is then provided by the output evaluator 3531 into the network 3521 to further develop (e.g., train) the network 3521. Additional input 3511 can be provided to the network 3521 until the output evaluator 3531 determines that the network 3521 is trained (e.g., the output has satisfied a known correlation of input to output according to a certain threshold, margin of error, etc.).

FIG. 35C depicts an example deployed device 3503. Once the training device 3501 has learned to a requisite level, the training device 3501 can be deployed for use. While the training device 3501 processes multiple inputs to learn, the deployed device 3503 processes a single input to determine an output, for example. As shown in the example of FIG. 35C, the deployed device 3503 includes an input definition 3513, a trained network 3523, and an output definition 3533. The trained network 3523 can be generated from the network 3521 once the network 3521 has been sufficiently trained, for example. The deployed device 3503 receives a system input 3513 and processes the input 3513 via the network 3523 to generate an output 3533, which can then be used by a system with which the deployed device 3503 has been associated, for example.

EXAMPLES

In one example, an infant care station can include a camera for capturing video data and a processor configured to execute instructions that can obtain the video data from the camera for a patient. The processor can also generate a point cloud based on the video data and train, using the point cloud as input, a first set of artificial intelligence instructions to detect one or more patient characteristics. Additionally, the processor can generate an output representing the one or more patient characteristics based on the first set of artificial intelligence instructions.

Alternatively, or in addition, the first set of artificial instructions can be trained using the point cloud representing one or more physical movements of the patient, one or more motor actions of the patient, or a combination thereof. Alternatively, or in addition, the one or more patient characteristics comprises a sleep wellness score for the patient. Alternatively, or in addition, the one or more patient characteristics comprises a pose or a sleep position for the patient. Alternatively, or in addition, the one or more patient characteristics comprises a pain assessment, a stress assessment, or a seizure assessment for the patient, the pain assessment and the seizure assessment based on physiologic measurements, physical measurements, audio, or video data.

Alternatively, or in addition, the processor is configured to provide a positive stimulus to the patient in response to detecting a negative stimulus based at least in part on the one or more patient characteristics, the positive stimulus comprising vestibular, somatosensory, tactile, or auditory stimuli. Alternatively, or in addition, the positive stimulus comprises an audio clip, a visual image to be displayed, a rocking movement applied to the patient, a rhythmic movement applied to the patient, or a combination thereof.

Alternatively, or in addition, the processor is configured to compute a mesh point cloud for the patient based on the video data, and train the first set of artificial intelligence instructions using the mesh point cloud. Alternatively, or in addition, the processor is configured to compute a segment mapping for the patient based on the video data, a point cloud, or a combination thereof, and train the first set of artificial intelligence instructions using the segment mapping.

Alternatively, or in addition, the one or more patient characteristics comprise one or more facial features or facial expressions of the neonatal patient. Alternatively, or in addition, the processor is to use the point cloud to determine at least one distance between two features of the neonatal patient.

Alternatively, or in addition, the processor is further configured to generate a growth chart based on the one or more physical characteristics, wherein the one or more physical characteristics comprise a head circumference, a body length, or a combination thereof.

Alternatively, or in addition, the training the first set of artificial intelligence instructions to detect the one or more patient characteristics further comprises training the first set of artificial intelligence instructions based at least in part on an image series, an audio time series, a physiologic measurement time series, or a combination thereof. Alternatively, or in addition, the processor is further configured to combine the first set of artificial intelligence instructions with one or more supplemental sets of artificial intelligence instructions trained to classify input based on the image series, the audio time series, the physiologic measurement time series, or the combination thereof.

Alternatively, or in addition, the physiologic measurement time series comprises one or more electrocardiogram (ECG) data values. Alternatively, or in addition, one or more patient characteristics comprises a patient body length, a patient head circumference, a patient body joint segment length, a body volume, a body surface area, or a body density.

In some examples, a method includes obtaining video data from a camera for a patient in an infant care station, generating a point cloud based on the video data, and training, using the point cloud as input, a first set of artificial intelligence instructions to detect one or more patient characteristics, wherein one or more patient characteristics comprises a patient body length, a patient head circumference, a patient body joint segment length, a body volume, a body surface area, or a body density. The method also includes generating an output representing the one or more patient characteristics based on the first set of artificial intelligence instructions.

Alternatively, or in addition, the method includes computing a mesh point cloud for the patient based on the video data, and training the first set of artificial intelligence instructions using the mesh point cloud.

Alternatively, or in addition, the training the first set of artificial intelligence instructions to detect the one or more patient characteristics further comprises training the first set of artificial intelligence instructions based at least in part on an image series, an audio time series, a physiologic measurement time series, or a combination thereof.

In some examples, non-transitory computer-readable media include a plurality of instructions that, in response to execution by a processor, cause the processor to obtain the video data from the camera for a patient and generate a point cloud based on the video data. The plurality of instructions also cause the processor to train, using the point cloud as input, a first set of artificial intelligence instructions to detect one or more patient characteristics, generate an output representing the one or more patient characteristics based on the first set of artificial intelligence instructions, and provide a positive stimulus to the patient in response to detecting a negative stimulus based at least in part on the one or more patient characteristics, the positive stimulus comprising vestibular, somatosensory, tactile, or auditory stimuli.

In some examples, a system for processing images can include a processor configured to obtain an infrared camera image and extract one or more movement indicators from the infrared camera image. The processor can also use wavelet decomposition to determine at least two data streams from the one or movement indicators and process the at least two data streams from the wavelet decomposition to determine any number of peaks that indicate a heart rate, respiratory rate, or a motion of a patient. The processor can also provide processed output to a user interface.

Alternatively, or in addition, the processor can calculate a plurality of pixel values for each of the at least two data streams, the plurality of pixel values comprising intensity values and perform a computation based on the plurality of pixel values. Alternatively, or in addition, the computation can include transforming the plurality of pixel values to a frequency domain to obtain a spectrum of frequencies for each of the at least two data streams.

Alternatively, or in addition, using the wavelet decomposition can include reconstructing an input signal based on the at least two data streams. Alternatively, or in addition, the wavelet decomposition can include generating a data structure based on a sum of components of the at least two data streams. Alternatively, or in addition, the processor can be further configured to provide a heart rate variability based on the wavelet decomposition.

Alternatively, or in addition, the processor can be configured to process at least three data streams from the wavelet decomposition to determine any number of peaks that indicate the heart rate, the respiratory rate, or the motion of the patient.

In some examples, a method can include obtaining an infrared camera image, extracting one or more movement indicators from the infrared camera image, and using wavelet decomposition to determine at least two data streams from the one or movement indicators. The method can also include processing the at least two data streams from the wavelet decomposition to determine any number of peaks that indicate a heart rate, respiratory rate, or a motion of a patient and providing processed output, based at least in part on the heart rate, the respiratory rate, or the motion of the patient, to a user interface.

Alternatively, or in addition, the method can include calculating a plurality of pixel values for each of the at least two data streams, the plurality of pixel values comprising intensity values, and performing a computation based on the plurality of pixel values. Alternatively, or in addition, the computation can include transforming the plurality of pixel values to a frequency domain to obtain a spectrum of frequencies for each of the at least two data streams. Alternatively, or in addition, using the wavelet decomposition includes reconstructing an input signal based on the at least two data streams. Alternatively, or in addition, the wavelet decomposition includes generating a data structure based on a sum of components of the at least two data streams.

Alternatively, or in addition, the method includes providing a heart rate variability based on the wavelet decomposition. Alternatively, or in addition, the method includes processing at least three data streams from the wavelet decomposition to determine any number of peaks that indicate the heart rate, the respiratory rate, or the motion of the patient.

In some examples, a non-transitory machine-executable media includes a plurality of instructions that, in response to execution by a processor, cause the processor to obtain an infrared camera image and extract one or more movement indicators from the infrared camera image. The plurality of instructions can also cause the processor to use wavelet decomposition to determine at least two data streams from the one or movement indicators and process the at least two data streams from the wavelet decomposition to determine any number of peaks that indicate a heart rate, respiratory rate, or a motion of a patient. In some examples, the processing includes calculating a plurality of pixel values for each of the at least two data streams, the plurality of pixel values comprising intensity values; and performing a computation based on the plurality of pixel values. The plurality of instructions can also cause the processor to provide processed output, based at least in part on the heart rate, the respiratory rate, or the motion of the patient, to a user interface.

Alternatively, or in addition, the computation can includes transforming the plurality of pixel values to a frequency domain to obtain a spectrum of frequencies for each of the at least two data streams. Alternatively, or in addition, the using the wavelet decomposition includes reconstructing an input signal based on the at least two data streams. Alternatively, or in addition, the wavelet decomposition includes generating a data structure based on a sum of components of the at least two data streams. Alternatively, or in addition, the plurality of instructions cause the processor to further provide a heart rate variability based on the wavelet decomposition. Alternatively, or in addition, the plurality of instructions cause the processor to process at least three data streams from the wavelet decomposition to determine any number of peaks that indicate the heart rate, the respiratory rate, or the motion of the patient.

In some examples, a system for detecting an oxygen saturation level of a patient includes a processor configured to create a first red plethysmograph waveform from a red image and create a second infrared (IR) plethysmograph waveform from an infrared (IR) image. The processor can also process the first red plethysmograph waveform using wavelet decomposition to obtain a first pulse plethysmograph waveform and process the second IR plethysmograph waveform using wavelet decomposition to obtain a second pulse plethysmograph waveform. Additionally, the processor can calculate an oxygen absorption value using the first pulse plethysmograph waveform and the second pulse plethysmograph waveform and determine the oxygen saturation value for the patient using a reference calibration curve and the oxygen absorption value.

Alternatively, or in addition, the red image is obtained from a red-green-blue (RGB) image of the patient in an infant care station. Alternatively, or in addition, the reference calibration curve calibrates the system to a second device with an accuracy above a predetermined threshold. Alternatively, or in addition, the processor can generate an alert in response to detecting the oxygen saturation value is below or above a predetermined range. Alternatively, or in addition, the processor can transmit the alert to a remote device.

Alternatively, or in addition, calculating the oxygen absorption value includes calculating a first amplitude of pulsations in the first pulse plethysmograph waveform and a second amplitude of pulsations in the second pulse plethysmograph waveform, calculating a first baseline offset in pulsations in the first pulse plethysmograph waveform and a second baseline offset in pulsations in the second pulse plethysmograph waveform, and combining the first amplitude, the second amplitude, the first baseline offset, and the second baseline offset to determine the oxygen absorption value.

Alternatively, or in addition, the wavelet decomposition used to obtain the first pulse plethysmograph waveform and the pulse plethysmograph waveform includes removing a respiratory rate or a motion artifact from the red image or the IR image. Alternatively, or in addition, the red image and the IR image include imaging data obtained from one or more regions of skin of the patient. Alternatively, or in addition, the one or more regions of skin of the patient include at least a peripheral limb and a forehead. Alternatively, or in addition, the one or more regions of skin of the patient include at least a peripheral limb and an abdomen. Alternatively, or in addition, the one or more regions include at least an abdomen and a forehead of the patient.

Alternatively, or in addition, the processor can determine the oxygen saturation value from the abdomen of the patient and determine a second oxygen saturation value from the forehead of the patient, compare the oxygen saturation value and the second oxygen saturation value, and determine a relative difference between the oxygen saturation value from the abdomen and the second oxygen saturation value from the forehead, wherein the relative difference indicates a disease state.

Alternatively, or in addition, the processor is further configured to obtain a transit plethysmography signal from a central location of a patient and a peripheral location of the patient, and determine a differential measurement representing a pulse transit time using the transit plethysmography signal from the central location and the peripheral location.

Alternatively, or in addition, the processor is further configured to obtain the first red plethysmograph waveform from the red image and the second IR plethysmograph waveform from the IR image, wherein the red image and the IR image are captured from one or more regions of the patient, calculate separate oxygen saturation values for each of the one or more regions using the first red plethysmograph waveform and the second IR plethysmograph waveform, and generate a relative value representing a difference between the oxygen saturation values for each of the one or more regions.

Alternatively, or in addition, the processor is further configured to obtain the first red plethysmograph waveform from the red image and the second IR plethysmograph waveform from the IR image, wherein the red image and the IR image are captured from one or more regions of the patient, calculate separate heart rate values for each of the one or more regions using the first plethysmograph waveform and the second plethysmograph waveform, and generate a relative value representing a difference between the heart rate values for each of the one or more regions.

Alternatively, or in addition, the processor is further configured to obtain the first red plethysmograph waveform from the red image and the second IR plethysmograph waveform from the IR image, wherein the red image and the IR image are captured from one or more regions of the patient, calculate separate respiration rate values for each of the one or more regions using the first plethysmograph waveform and the second plethysmograph waveform, and generate a relative value representing a difference between the respiration rate values for each of the one or more regions.

Alternatively, or in addition, the processor is further configured to process said first pulse plethysmograph waveform to obtain a peak to peak interval indicating a first heart rate (HR) value and process said second pulse plethysmograph waveform to obtain a peak to peak interval indicating a second heart rate (HR) value. Alternatively, or in addition, the processor is further configured to combine the first HR value and the second HR value to form an average heart rate value.

In some examples, a method for detecting an oxygen saturation level of a patient includes creating a first red plethysmograph waveform from a red image, creating a second infrared (IR) plethysmograph waveform from an infrared (IR) image, and processing the first red plethysmograph waveform using wavelet decomposition to obtain a first pulse plethysmograph waveform. The method also includes processing the second IR plethysmograph waveform using wavelet decomposition to obtain a second pulse plethysmograph waveform, calculating an oxygen absorption value using the first pulse plethysmograph waveform and the second pulse plethysmograph waveform, and determining the oxygen saturation value for the patient using a reference calibration curve and the oxygen absorption value. The method also includes generating an alert in response to detecting the oxygen saturation value is below or above a predetermined range.

In some examples, non-transitory machine-executable media include a plurality of instructions that, in response to execution by a processor, cause the processor to create a first red plethysmograph waveform from a red image and create a second infrared (IR) plethysmograph waveform from an infrared (IR) image. The plurality of instructions also cause the processor to process the first red plethysmograph waveform using wavelet decomposition to obtain a first pulse plethysmograph waveform, process the second IR plethysmograph waveform using wavelet decomposition to obtain a second pulse plethysmograph waveform, calculate an oxygen absorption value using the first pulse plethysmograph waveform and the second pulse plethysmograph waveform, and determine the oxygen saturation value for the patient using a reference calibration curve and the oxygen absorption value, wherein the reference calibration curve calibrates the system to a second device with an accuracy above a predetermined threshold. Additionally, the plurality of instructions cause the processor to generate an alert in response to detecting the oxygen saturation value is below or above a predetermined range.

As used herein, an element or step recited in the singular and proceeded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property. The terms “including” and “in which” are used as the plain-language equivalents of the respective terms “comprising” and “wherein.” Moreover, the terms “first,” “second,” and “third,” etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An infant care station comprising:

a camera for capturing video data; and a processor configured to execute instructions to:

obtain the video data from the camera for a patient;

generate a point cloud based on the video data, the point cloud defines discrete data points in XYZ vertices that are usable as a finite element model to estimate a body volume and a body surface area of the patient;

train, using the point cloud as input, a first set of artificial intelligence instructions to detect one or more patient characteristics; and generate an output representing the one or more patient characteristics based on the first set of artificial intelligence instructions.

2. The infant care station of claim 1, wherein the first set of artificial instructions is trained using the point cloud representing one or more physical movements of the patient, one or more motor actions of the patient, or a combination thereof.

3. The infant care station of claim 1, wherein the one or more patient characteristics comprises a sleep wellness score for the patient.

4. The infant care station of claim 1, wherein the one or more patient characteristics comprises a pose or a sleep position for the patient.

5. The infant care station of claim 1, wherein the one or more patient characteristics comprises a pain assessment, a stress assessment, or a seizure assessment for the patient, the pain assessment and the seizure assessment based on physiologic measurements, physical measurements, audio, or video data.

6. The infant care station of claim 1, wherein the processor is configured to provide a positive stimulus to the patient in response to detecting a negative stimulus based at least in part on the one or more patient characteristics, the positive stimulus comprising vestibular, somatosensory, tactile, or auditory stimuli.

7. The infant care station of claim 6, wherein the positive stimulus comprises an audio clip, a visual image to be displayed, a rocking movement applied to the patient, a rhythmic movement applied to the patient, or a combination thereof.

8. The infant care station of claim 1, wherein the processor is configured to:

compute a mesh point cloud for the patient based on the video data; and train the first set of artificial intelligence instructions using the mesh point cloud.

9. The infant care station of claim 1, wherein the processor is configured to:

compute a segment mapping for the patient based on the video data, the point cloud, or a combination thereof; and train the first set of artificial intelligence instructions using the segment mapping.

10. The infant care station of claim 1, wherein the one or more patient characteristics comprise one or more facial features or facial expressions of the patient.

11. The infant care station of claim 1, wherein the processor is to use the point cloud to determine at least one distance between two features of the patient.

12. The infant care station of claim 1, wherein the processor is further configured to generate a growth chart based on the one or more patient characteristics, wherein the one or more patient characteristics comprise a head circumference, a body length, or a combination thereof.

13. The infant care station of claim 1, wherein the training the first set of artificial intelligence instructions to detect the one or more patient characteristics further comprises training the first set of artificial intelligence instructions based at least in part on an image series, an audio time series, a physiologic measurement time series, or a combination thereof.

14. The infant care station of claim 13, wherein the processor is further configured to combine the first set of artificial intelligence instructions with one or more supplemental sets of artificial intelligence instructions trained to classify input based on the image series, the audio time series, the physiologic measurement time series, or the combination thereof.

15. The infant care station of claim 13, wherein the physiologic measurement time series comprises one or more electrocardiogram (ECG) data values.

16. The infant care station of claim 1, wherein one or more patient characteristics comprises a patient body length, a patient head circumference, a patient body joint segment length, a body volume, a body surface area, or a body density.

17. A method comprising:

obtaining video data from a camera for a patient in an infant care station;

generating a point cloud based on the video data, the point cloud defines discrete data points in XYZ vertices that are usable as a finite element model to estimate a body volume and a body surface area of the patient;

training, using the point cloud as input, a first set of artificial intelligence instructions to detect one or more patient characteristics, wherein the one or more patient characteristics comprises a body length, a head circumference, a body joint segment length, a body volume, a body surface area, or a body density of the patient; and generating an output representing the one or more patient characteristics based on the first set of artificial intelligence instructions.

18. The method of claim 17, further comprising:

computing a mesh point cloud for the patient based on the video data; and training the first set of artificial intelligence instructions using the mesh point cloud.

19. The method of claim 17, wherein the training the first set of artificial intelligence instructions to detect the one or more patient characteristics further comprises training the first set of artificial intelligence instructions based at least in part on an image series, an audio time series, a physiologic measurement time series, or a combination thereof.

20. A non-transitory computer-readable media comprising a plurality of instructions that, in response to execution by a processor, cause the processor to:

obtain video data from a camera for a patient;

generate a point cloud based on the video data, the point cloud defines discrete data points in XYZ vertices that are usable as a finite element model to estimate a body volume and a body surface area of the patient;

train, using the point cloud as input, a first set of artificial intelligence instructions to detect one or more patient characteristics;

generate an output representing the one or more patient characteristics based on the first set of artificial intelligence instructions; and provide a positive stimulus to the patient in response to detecting a negative stimulus based at least in part on the one or more patient characteristics, the positive stimulus comprising vestibular, somatosensory, tactile, or auditory stimuli.

* * * * *